(12) United States Patent
Wakita et al.

(10) Patent No.: US 8,592,559 B2
(45) Date of Patent: Nov. 26, 2013

(54) ANTIBODY HAVING ACTIVITY OF INHIBITING HEPATITIS C VIRUS (HCV) INFECTION AND USE THEREOF

(75) Inventors: Takaji Wakita, Tokyo (JP); Kazumi Nishimura, Kanagawa (JP); Noriko Nakamura, Kanagawa (JP); Daisuke Akazawa, Kanagawa (JP)

(73) Assignees: Toray Industries, Inc., Tokyo (JP); Japan as Represented by Director-General of National Institute of Infectious Diseases, Tokyo (JP)

( * ) Notice: Subject to any disclaimer, the term of this patent is extended or adjusted under 35 U.S.C. 154(b) by 0 days.

(21) Appl. No.: 13/504,765

(22) PCT Filed: Oct. 29, 2010

(86) PCT No.: PCT/JP2010/069323
§ 371 (c)(1),
(2), (4) Date: Apr. 27, 2012

(87) PCT Pub. No.: WO2011/052735
PCT Pub. Date: May 5, 2011

(65) Prior Publication Data
US 2012/0220758 A1 Aug. 30, 2012

(30) Foreign Application Priority Data

Oct. 30, 2009 (JP) ................................ 2009-251165
Oct. 30, 2009 (JP) ................................ 2009-251341

(51) Int. Cl.
*C07K 16/08* (2006.01)

(52) U.S. Cl.
USPC .................. 530/387.1; 530/388.1; 530/388.3; 530/808

(58) Field of Classification Search
None
See application file for complete search history.

(56) References Cited

U.S. PATENT DOCUMENTS

| | | |
|---|---|---|
| 2009/0110685 A1 | 4/2009 | Patel et al. |
| 2010/0035345 A1 | 2/2010 | Tanabe et al. |
| 2010/0291545 A1 | 11/2010 | Wakita et al. |

FOREIGN PATENT DOCUMENTS

| | | |
|---|---|---|
| JP | 2008-532559 A | 8/2008 |
| WO | WO 00/05266 A1 | 2/2000 |
| WO | WO 2004/087760 A1 | 10/2004 |
| WO | WO 2006/041866 A2 | 4/2006 |
| WO | WO 2007/037428 A1 | 4/2007 |
| WO | WO 2009/014216 A1 | 1/2009 |
| WO | WO 2010/039154 A1 | 4/2010 |

OTHER PUBLICATIONS

Ania M. Owsianka et al. Broadly neutralizing human monoclonal antibodies to the hepatitis C virus E2 glycoprotein J Gen Virol. Mar. 2008; 89(Pt 3): 653-659.*
Owsianka AM et al. Broadly neutralizing human monoclonal antibodies to the hepatitis C virus E2 glycoprotein. J Gen Virol. Mar. 2008;89(Pt 3):653-9.*
Perotti M et al. Identification of a broadly cross-reacting and neutralizing human monoclonal antibody directed against the hepatitis C virus E2 protein. J Virol. Jan. 2008;82(2):1047-52.*
International Search Report issued in PCT/JP2010/069323, dated Jan. 18, 2011.
Written Opinion of the International Searching Authority issued in PCT/JP2010/069323, dated Jan. 18, 2011.
European Search Report for European Application No. 10826865.7 dated Aug. 22, 2013.
Law et al., "Broadly Neutralizing Antibodies Protect Against Hepatitis C Virus Quasispecies Challenge", Nature Medicine, vol. 14, No. 1, pp. 25-27, Jan. 1, 2008.
Petit et al., "Mapping of a Conformational Epitope Shared Between E1 and E2 on the Serum-derived Human . . . ", Journal of Biological Chemistry, vol. 278, No. 45, pp. 44385-44392, Nov. 7, 2003.
Schofield et al., "Human Monoclonal Antibodies That React With the E2 Glycoprotein of Hepatitis C Virus and Possess Neutralizing Activity", Hepatology, vol. 42, No. 5, pp. 1055-1062, Nov. 1, 2005.
Triyatni et al., "Structural Features of Envelope Proteins on Hepatitis C Virus-like Particles as Determined by Anti-envelope Monoclonal Antibodies and CD81 Binding", Virology, Elsevier, Amsterdam, NL, vol. 298, No. 1, pp. 124-132, Jun. 20, 2002.

* cited by examiner

*Primary Examiner* — Zachariah Lucas
*Assistant Examiner* — Nick Zou
(74) *Attorney, Agent, or Firm* — Birch, Stewart, Kolasch & Birch, LLP

(57) ABSTRACT

An object of the present invention is to provide an antibody inhibiting infection with hepatitis C virus (HCV). The present invention provides an anti-hepatitis C virus antibody that recognizes a whole or a part of the conformation of a hepatitis C virus particle as an epitope and binds thereto, so as to be able to inhibit the binding of hepatitis C virus to the surface of a host cell and to inhibit HCV infection, a humanized antibody thereof, and an inhibitory agent for infection with hepatitis C virus.

5 Claims, 8 Drawing Sheets

```
                           SEQUENCE LISTING

<160> NUMBER OF SEQ ID NOS: 44

<210> SEQ ID NO 1
<211> LENGTH: 9678
<212> TYPE: DNA
<213> ORGANISM: Artificial
<220> FEATURE:
<223> OTHER INFORMATION: Cloned HCV genomic cDNA in pJFH-1

<400> SEQUENCE: 1
acctgcccct aatagggcg acactccgcc atgaatcact cccctgtgag gaactactgt      60
```

```
cttcacgcag aaagcgccta gccatggcgt tagtatgagt gtcgtacagc ctccaggccc    120 cccctcccg ggagagccat agtggtctgc ggaaccggtg agtacaccgg aattgccggg    180
aagactgggt cctttcttgg ataaacccac tctatgcccg ccatttggg cgtgcccccg     240 caagactgct agccgagtag cgttgggttg cgaaaggcct tgtggtactg cctgataggg    300
cgcttgcgag tgcccggga ggtctcgtag accgtgcacc atgagcacaa atcctaaacc     360
tcaaagaaaa accaaagaa acaccaaccg tcgcccagaa gacgttaagt tcccgggcgg     420
cggccagatc gttggcggag tatacttgtt gccgcgcagg ggcccaggt tgggtgtgcg     480 cacgacaagg aaaacttcgg agcggtccca gccacgtggg agacgccagc ccatcccaa     540 agatcggcgc tccactggca aggcctgggg aaaaccaggt cgccctggc ccctatatgg    600 gaatgaggga ctcggctggg caggatggct cctgtccccc cgaggctctc gcccctcctg    660 gggcccccact gaccccggc ataggtcgcg caacgtgggt aaagtcatcg acaccctaac    720
gtgtggcttt gccgacctca tggggtacat ccccgtcgta ggcgcccgc ttagtggcgc    780 cgccagagct gtcgcgcacg gcgtgagagt cctggaggac ggggttaatt atgcaacagg    840
gaacctaccc ggtttcccct tttctatctt cttgctggcc ctgttgtcct gcatcaccgt    900
tccggtctct gctgcccagg tgaagaatac cagtagcagc tacatggtga ccaatgactg    960
ctccaatgac agcatcactt ggcagctcga ggctgcggtt ctccacgtcc ccgggtgcgt   1020
cccgtgcgag agagtgggga atacgtcacg gtgttgggtg ccagtctcgc caaacatggc   1080
tgtgcggcag cccggtgccc tcacgcaggg tctgcggacg cacatcgata tggttgtgat   1140
gtccgccacc ttctgctctg ctctctacgt gggggacctc tgtggcgggg tgatgctcgc   1200
ggcccaggtg ttcatcgtct cgccgcagta ccactggttt gtgcaagaat gcaattgctc   1260
catctaccct ggcaccatca ctggacaccg catggcatgg gacatgatga tgaactggtc   1320
gcccacggcc accatgatcc tggcgtacgt gatgcgcgtc cccgaggtca tcatagacat   1380
cgttagcggg gctcactggg gcgtcatgtt cggcttggcc tacttctcta tgcagggagc   1440
gtgggcgaag gtcattgtca tccttctgct ggccgctggg gtggacgcgg gcaccaccac   1500
cgttggaggc gctgttgcac gttccaccaa cgtgattgcc ggcgtgttca gccatggccc   1560
tcagcagaac attcagctca ttaacaccaa cggcagttgg cacatcaacc gtactgcctt   1620
gaattgcaat gactccttga acaccggctt tctcgcggcc ttgttctaca ccaaccgctt   1680
taactcgtca gggtgtccag ggcgcctgtc cgcctgccgc aacatcgagg ctttccggat   1740
agggtggggc accctacagt acgaggataa tgtcaccaat ccagaggata tgaggccgta   1800
ctgctggcac tacccccaa agccgtgtgg cgtagtcccc gcgaggtctg tgtgtggccc    1860
agtgtactgt ttcaccccca gcccggtagt agtgggcacg accgacagac gtggagtgcc   1920
cacctacaca tggggagaga atgagacaga tgtcttccta ctgaacagca cccgaccgcc   1980
gcagggctca tggttcggct gcacgtggat gaactccact ggtttcacca agacttgtgg   2040
cgcgccacct tgccgcacca gagctgactt caacgccagc acggacttgt tgtgccctac   2100
ggattgtttt aggaagcatc ctgatgccac ttatattaag tgtggttctg ggcctggct    2160 cacaccaaag tgcctggtcc actaccctta cagactctgg cattacccct gcacagtcaa   2220
ttttaccatc ttcaagataa gaatgtatgt aggggggtt gagcacaggc tcacggccgc   2280
atgcaacttc actcgtgggg atcgctgcga cttggaggac agggacagga gtcagctgtc   2340
tcctctgttg cactctacca cggaatgggc catcctgccc tgcacctact cagacttacc   2400
cgctttgtca actggtcttc tccaccttca ccagaacatc gtggacgtac aatacatgta   2460
```

```
tggcctctca cctgctatca caaaatacgt cgttcgatgg gagtgggtgg tactcttatt   2520
cctgctctta gcggacgcca gagtctgcgc ctgcttgtgg atgctcatct tgttgggcca   2580
ggccgaagca gcattggaga agttggtcgt cttgcacgct gcgagtgcgg ctaactgcca   2640
tggcctccta tattttgcca tcttcttcgt ggcagcttgg cacatcaggg gtcgggtggt   2700 cccccttgacc acctattgcc tcactggcct atggcccttc tgcctactgc tcatggcact   2760
gccccggcag gcttatgcct atgacgcacc tgtgcacgga cagataggcg tgggtttgtt   2820
gatattgatc accctcttca cactcacccc ggggtataag accctcctcg gccagtgtct   2880
gtggtggttg tgctatctcc tgaccctggg ggaagccatg attcaggagt gggtaccacc   2940
catgcaggtg cgcggcggcc gcgatggcat cgcgtgggcc gtcactatat tctgcccggg   3000
tgtggtgttt gacattacca aatggctttt ggcgttgctt gggcctgctt acctcttaag   3060
ggccgctttg acacatgtgc cgtacttcgt cagagctcac gctctgataa gggtatgcgc   3120
tttggtgaag cagctcgcgg ggggtaggta tgttcaggtg gcgctattgg cccttggcag   3180
gtggactggc acctacatct atgaccacct cacacctatg tcggactggg ccgctagcgg   3240
cctgcgcgac ttagcggtcg ccgtggaacc catcatcttc agtccgatgg agaagaaggt   3300
catcgtctgg ggagcggaga cggctgcatg tggggacatt ctacatggac ttcccgtgtc   3360
cgcccgactc ggccaggaga tcctcctcgg cccagctgat ggctacacct caaggggtg    3420 gaagctcctt gctcccatca ctgcttatgc ccagcaaaca cgaggcctcc tgggcgccat   3480
agtggtgagt atgacgggc gtgacaggac agaacaggcc ggggaagtcc aaatcctgtc    3540
cacagtctct cagtccttcc tcggaacaac catctcgggg gttttgtgga ctgtttacca   3600
cggagctggc aacaagactc tagccggctt acggggtccg gtcacgcaga tgtactcgag   3660
tgctgagggg gacttggtag gctggcccag ccccctggg accaagtctt tggagccgtg    3720
caagtgtgga gccgtcgacc tatatctggt cacgcggaac gctgatgtca tcccggctcg   3780
gagacgcggg gacaagcggg gagcattgct ctccccgaga cccatttcga ccttgaaggg   3840
gtcctcgggg gggccggtgc tctgccctag gggccacgtc gttgggctct tccgagcagc   3900
tgtgtgctct cggggcgtgg ccaaatccat cgatttcatc cccgttgaga cactcgacgt   3960
tgttacaagg tctcccactt tcagtgacaa cagcacgcca ccggctgtgc cccagaccta   4020
tcaggtcggg tacttgcatg ctccaactgg cagtggaaag agcaccaagg tccctgtcgc   4080
gtatgccgcc caggggtaca agtactagt gcttaacccc tcggtagctg ccaccctggg   4140
gtttggggcg tacctatcca aggcacatgg catcaatccc aacattagga ctggagtcag   4200
gaccgtgatg accggggagg ccatcacgta ctccacatat ggcaaatttc tcgccgatgg   4260
gggctgcgct agcggcgcct atgacatcat catatgcgat gaatgccacg ctgtggatgc   4320
tacctccatt ctcggcatcg gaacggtcct tgatcaagca gagacagccg gggtcagact   4380
aactgtgctg gctacggcca cacccccgg gtcagtgaca accccccatc ccgatatag    4440 agaggtaggc ctcgggcggg agggtgagat cccttctat gggagggcga ttccccctatc    4500 ctgcatcaag ggagggagac acctgatttt ctgccactca aagaaaaagt gtgacgagct   4560
cgcggcggcc cttcggggca tgggcttgaa tgccgtggca tactatagag ggttggacgt   4620
ctccataata ccagctcagg gagatgtggt ggtcgtcgcc accgacgccc tcatgacggg   4680
gtacactgga gactttgact ccgtgatcga ctgcaatgta gcggtcaccc aagctgtcga   4740
cttcagcctg gaccccacct tcactataac cacacagact gtcccacaag acgctgtctc   4800
acgcagtcag cgccgcgggc gcacaggtag aggaagacag ggcactttata ggtatgtttc   4860
```

```
cactggtgaa cgagcctcag gaatgtttga cagtgtagtg ctttgtgagt gctacgacgc   4920 agggggctgcg tggtacgatc tcacaccagc ggagaccacc gtcaggctta gagcgtattt   4980
caacacgccc ggcctacccg tgtgtcaaga ccatcttgaa ttttgggagg cagttttcac   5040
cggcctcaca cacatagacg cccacttcct ctcccaaaca aagcaagcgg gggagaactt   5100
cgcgtaccta gtagcctacc aagctacggt gtgcgccaga gccaaggccc ctccccgtc    5160 ctgggacgcc atgtggaagt gcctggcccg actcaagcct acgcttgcgg ccccacacc    5220 tctcctgtac cgtttgggcc ctattaccaa tgaggtcacc ctcacacacc ctgggacgaa   5280
gtacatcgcc acatgcatgc aagctgacct tgaggtcatg accagcacgt gggtcctagc   5340
tggaggagtc ctggcagccg tcgccgcata ttgcctggcg actggatgcg tttccatcat   5400
cggccgcttg cacgtcaacc agcgagtcgt cgttgcgccg gataaggagg tcctgtatga   5460
ggcttttgat gagatggagg aatgcgcctc tagggcggct ctcatcgaag aggggcagcg   5520
gatagccgag atgttgaagt ccaagatcca aggcttgctg cagcaggcct ctaagcaggc   5580
ccaggacata caacccgcta tgcaggcttc atggcccaaa gtggaacaat tttgggccag   5640
acacatgtgg aacttcatta gcggcatcca atacctcgca ggattgtcaa cactgccagg   5700
gaaccccgcg gtggcttcca tgatggcatt cagtgccgcc ctcaccagtc gttgtcgac    5760 cagtaccacc atccttctca acatcatggg aggctggtta gcgtcccaga tcgcaccacc   5820
cgcgggggcc accggctttg tcgtcagtgg cctggtgggg gctgccgtgg gcagcatagg   5880
cctgggtaag gtgctggtgg acatcctggc aggatatggt gcgggcattt cgggggccct   5940
cgtcgcattc aagatcatgt ctggcgagaa gccctctatg gaagatgtca tcaatctact   6000
gcctgggatc ctgtctccgg gagccctggt ggtgggggtc atctgcgcgg ccattctgcg   6060
ccgccacgtg gaccgggggg agggcgcggt ccaatggatg aacaggctta ttgcctttgc   6120
ttccagagga aaccacgtcg cccctactca ctacgtgacg gagtcggatg cgtcgcagcg   6180
tgtgacccaa ctacttggct ctcttactat aaccagccta ctcagaagac tccacaattg   6240
gataactgag gactgcccca tcccatgctc cggatcctgg ctccgcgacg tgtgggactg   6300
ggtttgcacc atcttgacag acttcaaaaa ttggctgacc tctaaattgt tccccaagct   6360
gcccggcctc cccttcatct cttgtcaaaa ggggtacaag ggtgtgtggg ccggcactgg   6420
catcatgacc acgcgctgcc cttgcggcgc caacatctct ggcaatgtcc gcctgggctc   6480
tatgaggatc acagggccta aaacctgcat gaacacctgg caggggacct ttcctatcaa   6540
ttgctacacg gagggccagt gcgcgccgaa acccccacg aactacaaga ccgccatctg    6600
gagggtggcg gcctcggagt acgcggaggt gacgcagcat gggtcgtact cctatgtaac   6660
aggactgacc actgacaatc tgaaaattcc ttgccaacta ccttctccag agtttttctc   6720
ctgggtggac ggtgtgcaga tccataggtt tgcacccaca ccaaagccgt ttttccggga   6780
tgaggtctcg ttctgcgttg gcttaattc ctatgctgtc gggtcccagc ttccctgtga    6840
acctgagccc gacgcagacg tattgaggtc catgctaaca gatccgcccc acatcacggc   6900
ggagactgcg gcgcggcgct tggcacgggg atcacctcca tctgaggcga gctcctcagt   6960
gagccagcta tcagcaccgt cgctgcgggc cacctgcacc acccacagca cacctatga    7020 cgtggacatg gtcgatgcca acctgctcat ggagggcggt gtggctcaga cagagcctga   7080
gtccagggtg cccgttctgg actttctcga gccaatggcc gaggaagaga gcgaccttga   7140
gccctcaata ccatcggagt gcatgctccc caggagcggg tttccacggg ccttaccggc   7200
ttgggcacgg cctgactaca acccgccgct cgtggaatcg tggaggaggc cagattacca   7260
```

```
accgcccacc gttgctggtt gtgctctccc ccccccaag aaggcccga cgcctccccc    7320 aaggagacgc cggacagtgg gtctgagcga gagcaccata tcagaagccc tccagcaact    7380
ggccatcaag acctttggcc agccccctc gagcggtgat gcaggctcgt ccacggggc     7440 gggcgccgcc gaatccggcg gtccgacgtc ccctggtgag ccggcccct cagagacagg    7500 ttccgcctcc tctatgcccc ccctcgaggg ggagcctgga gatccggacc tggagtctga    7560
tcaggtagag cttcaacctc cccccaggg ggggggggta gctcccggtt cgggctcggg    7620
gtcttggtct acttgctccg aggaggacga taccaccgtg tgctgctcca tgtcatactc    7680
ctggaccggg gctctaataa ctccctgtag ccccgaagag gaaaagttgc caatcaaccc    7740
tttgagtaac tcgctgttgc gataccataa caaggtgtac tgtacaacat caaagagcgc    7800
ctcacagagg gctaaaaagg taacttttga caggacgcaa gtgctcgacg cccattatga    7860
ctcagtctta aaggacatca agctagcggc ttccaaggtc agcgcaaggc tcctcacctt    7920
ggaggaggcg tgccagttga ctccacccca ttctgcaaga tccaagtatg gattcggggc    7980
caaggaggtc cgcagcttgt cgggagggc cgttaaccac atcaagtccg tgtggaagga    8040
cctcctggaa gacccacaaa caccaattcc cacaaccatc atggccaaaa atgaggtgtt    8100
ctgcgtggac cccgccaagg ggggtaagaa accagctcgc ctcatcgttt accctgacct    8160
cggcgtccgg gtctgcgaga aaatggccct ctatgacatt acacaaaagc ttcctcaggc    8220
ggtaatggga gcttcctatg gcttccagta ctcccctgcc caacgggtgg agtatctctt    8280
gaaagcatgg gcgaaaaga aggacccat gggtttttcg tatgataccc gatgcttcga    8340
ctcaaccgtc actgagagag acatcaggac cgaggagtcc atataccagg cctgctccct    8400
gcccgaggag gcccgcactg ccatacactc gctgactgag agactttacg taggagggcc    8460
catgttcaac agcaagggtc aaacctgcgg ttacagacgt tgccgcgcca gcggggtgct    8520
aaccactagc atgggtaaca ccatcacatg ctatgtgaaa gccctagcgg cctgcaaggc    8580
tgcggggata gttgcgccca caatgctggt atgcggcgat gacctagtag tcatctcaga    8640
aagccagggg actgaggagg acgagcggaa cctgagagcc ttcacggagg ccatgaccag    8700
gtactctgcc cctcctggtg atccccccag accggaatat gacctggagc taataacatc    8760
ctgttcctca aatgtgtctg tggcgttggg cccgcgggc cgccgcagat actacctgac    8820
cagagaccca accactccac tcgcccgggc tgcctgggaa acagttagac actcccctat    8880
caattcatgg ctgggaaaca tcatccagta tgctccaacc atatgggttc gcatggtcct    8940
aatgacacac ttcttctcca ttctcatggt ccaagacacc ctggaccaga acctcaactt    9000
tgagatgtat ggatcagtat actccgtgaa tccttttggac cttccagcca taattgagag    9060
gttacacggg cttgacgcct tttctatgca cacatactct caccacgaac tgacgcgggt    9120
ggcttcagcc ctcagaaaac ttggggcgcc acccctcagg gtgtggaaga gtcgggctcg    9180
cgcagtcagg gcgtccctca tctcccgtgg agggaaagcg gccgtttgcg gccgatatct    9240
cttcaattgg gcggtgaaga ccaagctcaa actcactcca ttgccggagg gcgcgcctact    9300 ggacttatcc agttggttca ccgtcggcgc cggcggggc gacattttc acagcgtgtc    9360 gcgcgcccga ccccgctcat tactcttcgg cctactccta cttttcgtag gggtaggcct    9420
cttcctactc cccgctcggt agagcggcac acactaggta cactccatag ctaactgttc    9480 ctttttttt tttttttttt tttttttttt tttttttttt tttctttttt ttttttttc    9540 cctctttctt cccttctcat cttattctac tttcttcttt ggtggctcca tcttagccct    9600
agtcacggct agctgtgaaa ggtccgtgag ccgcatgact gcagagagtg ccgtaactgg    9660
```

-continued tctctctgca gatcatgt 9678

<210> SEQ ID NO 2
<211> LENGTH: 9683
<212> TYPE: DNA
<213> ORGANISM: Artificial
<220> FEATURE:
<223> OTHER INFORMATION: Cloned HCV genomic cDNA in pJ6/JFH-1

<400> SEQUENCE: 2

```
acccgcccct aatagggggcg acactccgcc atgaatcact ccctgtgag gaactactgt      60
cttcacgcag aaagcgtcta gccatggcgt tagtatgagt gtcgtacagc ctccaggccc     120
cccctcccg ggagagccat agtggtctgc ggaaccggtg agtacaccgg aattgccggg     180
aagactgggt cctttcttgg ataaacccac tctatgcccg gccatttggg cgtgccccg      240
caagactgct agccgagtag cgttgggttg cgaaaggcct tgtggtactg cctgataggg     300
tgcttgcgag tgccccggga ggtctcgtag accgtgcacc atgagcacaa atcctaaacc     360
tcaaagaaaa accaaaagaa acaccaaccg tcgcccacaa gacgttaagt tccgggcgg      420
cggccagatc gttggcggag tatacttgtt gccgcgcagg ggcccaggt tgggtgtgcg     480
cgcgacaagg aagacttcgg agcggtccca gccacgtgga aggcgccagc ccatccctaa     540
agatcggcgc tccactggca aatcctgggg aaaaccagga taccctggc cctatacgg      600
gaatgaggga ctcggctggg caggatggct cctgtcccc cgaggttccc gtccctcttg     660
gggcccaat gacccccggc ataggtcgcg caacgtgggt aaggtcatcg ataccctaac     720
gtgcggcttt gccgacctca tggggtacat ccctgtcgtg ggcgccccgc tcggcggcgt     780
cgccagagct ctcgcgcatg gcgtgagagt cctggaggac gggggttaatt ttgcaacagg     840
gaacttaccc ggttgctcct tttctatctt cttgctggcc ctgctgtcct gcatcaccac     900
cccggtctcc gctgccgaag tgaagaacat cagtaccggc tacatggtga ctaacgactg     960
caccaatgac agcattacct ggcagctcca ggctgctgtc ctccacgtcc ccgggtgcgt    1020
cccgtgcgag aaagtgggga atgcatctca gtgctggata ccggtctcac cgaatgtggc    1080
cgtgcagcgg cccggcgccc tcacgcaggg cttgcggacg cacatcgaca tggttgtgat    1140
gtccgccacg ctctgctctg ccctctacgt ggggggacctc tgcggtgggg tgatgctcgc    1200
agcccaaatg ttcattgtct cgccgcagca ccactggttt gtccaagact gcaattgctc    1260
catctaccct ggtaccatca ctggacaccg catggcatgg gacatgatga tgaactggtc    1320
gcccacggct accatgatct tggcgtacgc gatgcgtgtc cccgaggtca ttatagacat    1380
cattagcggg gctcattggg gcgtcatgtt cggcttggcc tacttctcta tgcagggagc    1440
gtgggcgaaa gtcgttgtca tccttctgtt ggccgccggg gtggacgcgc gcacccatac    1500
tgttgggggt tctgccgcgc agaccaccgg gcgcctcacc agcttattg acatgggccc    1560
caggcagaaa atccagctcg ttaacaccaa tggcagctgg cacatcaacc gcaccgccct    1620
gaactgcaat gactccttgc acaccggctt tatcgcgtct ctgttctaca cccacagctt    1680
caactcgtca ggatgtcccg aacgcatgtc cgcctgccgc agtatcgagg ccttccgggt    1740
gggatgggc gccttgcaat atgaggataa tgtcaccaat ccagaggata tgagaccca    1800
ttgctggcac tacccaccaa ggcagtgtgg cgtggtctcc gcgaagactg tgtgtggccc    1860
agtgtactgt ttcacccca gcccagtggg tagtgggcacg accgacaggc ttggagcgcc    1920
cacttacacg tggggggaga atgagacaga tgtcttccta ttgaacagca ctcgaccacc    1980
gctggggtca tggttcggct gcacgtggat gaactcttct ggctacacca agacttgcgg    2040
```

```
cgcaccaccc tgccgtacta gagctgactt caacgccagc acggacctgt tgtgccccac    2100
ggactgtttt aggaagcatc ctgataccac ttacctcaaa tgcggctctg ggccctggct    2160
cacgccaagg tgcctgatcg actaccccta caggctctgg cattacccct gcacagttaa    2220
ctataccatc ttcaaaataa ggatgtatgt gggagggggtt gagcacaggc tcacggctgc    2280
atgcaatttc actcgtgggg atcgttgcaa cttggaggac agagacagaa gtcaactgtc    2340
tcctttgttg cactccacca cggaatgggc cattttacct tgctcttact cggacctgcc    2400
cgccttgtcg actggtcttc tccacctcca ccaaaacatc gtggacgtac aattcatgta    2460
tggcctatca cctgccctca caaaatacat cgtccgatgg gagtgggtaa tactcttatt    2520
cctgctctta gcggacgcca gggtttgcgc ctgcttatgg atgctcatct tgttgggcca    2580
ggccgaagca gcactagaga agctggtcat cttgcacgct gcgagcgcag ctagctgcaa    2640
tggcttccta tattttgtca tcttttttcgt ggctgcttgg tacatcaagg gtcgggtagt    2700 cccccttagct acctattccc tcactggcct gtggtccttt agcctactgc tcctagcatt    2760
gccccaacag gcttatgctt atgacgcatc tgtgcatggc cagataggag cggctctgct    2820
ggtaatgatc accctcttca cactcacccc ggggtataag accctcctcg gccagtgtct    2880
gtggtggttg tgctatctcc tgaccctggg ggaagccatg attcaggagt gggtaccacc    2940
catgcaggtg cgcggcggcc gcgatggcat cgcgtgggcc gtcactatat tctgcccggg    3000
tgtggtgttt gacattacca aatggctttt ggcgttgctt gggcctgctt acctcttaag    3060
ggccgctttg acacatgtgc cgtacttcgt cagagctcac gctctgataa gggtatgcgc    3120
tttggtgaag cagctcgcgg ggggtaggta tgttcaggtg gcgctattgg cccttggcag    3180
gtggactggc acctacatct atgaccacct cacacctatg tcggactggg ccgctagcgg    3240
cctgcgcgac ttagcggtcg ccgtggaacc catcatcttc agtccgatgg agaagaaggt    3300
catcgtctgg ggagcggaga cggctgcatg tggggacatt ctacatggac ttcccgtgtc    3360
cgcccgactc ggccaggaga tcctcctcgg cccagctgat ggctacacct ccaaggggtg    3420
gaagctcctt gctcccatca ctgcttatgc ccagcaaaca cgaggcctcc tgggcgccat    3480
agtggtgagt atgacggggc gtgacaggac agaacaggcc ggggaagtcc aaatcctgtc    3540
cacagtctct cagtccttcc tcggaacaac catctcgggg gttttgtgga ctgtttacca    3600
cggagctggc aacaagactc tagccggctt acggggtccg gtcacgcaga tgtactcgag    3660
tgctgagggg gacttggtag gctggcccag ccccccctggg accaagtctt tggagccgtg    3720
caagtgtgga gccgtcgacc tatatctggt cacgcggaac gctgatgtca tcccggctcg    3780
gagacgcggg gacaagcggg gagcattgct ctccccgaga cccatttcga ccttgaaggg    3840
gtcctcgggg gggccggtgc tctgccctag gggccacgtc gttgggctct tccgagcagc    3900
tgtgtgctct cggggcgtgg ccaaatccat cgatttcatc cccgttgaga cactcgacgt    3960
tgttacaagg tctcccactt tcagtgacaa cagcacgcca ccggctgtgc cccagaccta    4020
tcaggtcggg tacttgcatg ctccaactgg cagtggaaag agcaccaagg tccctgtcgc    4080
gtatgccgcc caggggtaca agtactagt gcttaacccc tcggtagctg ccaccctggg    4140
gtttggggcg tacctatcca aggcacatgg catcaatccc aacattagga ctggagtcag    4200
gaccgtgatg accggggagg ccatcacgta ctccacatat ggcaaatttc tcgccgatgg    4260
gggctgcgct agcggcgcct atgacatcat catatgcgat gaatgccacg ctgtggatgc    4320
tacctccatt ctcggcatcg gaacggtcct tgatcaagca gagacagccg gggtcagact    4380
aactgtgctg gctacggcca caccccccgg gtcagtgaca accccccatc ccgatataga    4440
```

```
agaggtaggc ctcgggcggg agggtgagat cccttctat gggagggcga ttcccctatc   4500
ctgcatcaag ggagggagac acctgatttt ctgccactca agaaaaagt gtgacgagct   4560 cgcggcggcc cttcggggca tgggcttgaa tgccgtggca tactatagag ggttggacgt   4620
ctccataata ccagctcagg gagatgtggt ggtcgtcgcc accgacgccc tcatgacggg   4680
gtacactgga gactttgact ccgtgatcga ctgcaatgta gcggtcaccc aagctgtcga   4740
cttcagcctg gaccccacct tcactataac cacacagact gtcccacaag acgctgtctc   4800
acgcagtcag cgccgcgggc gcacaggtag aggaagacag ggcacttata ggtatgtttc   4860
cactggtgaa cgagcctcag gaatgtttga cagtgtagtg ctttgtgagt gctacgacgc   4920
aggggctgcg tggtacgatc tcacaccagc ggagaccacc gtcaggctta gagcgtattt   4980
caacacgccc ggcctacccg tgtgtcaaga ccatcttgaa ttttgggagg cagttttcac   5040
cggcctcaca cacatagacg cccacttcct ctcccaaaca aagcaagcgg gggagaactt   5100
cgcgtaccta gtagcctacc aagctacggt gtgcgccaga gccaaggccc ctccccgtc   5160 ctggacgcc atgtggaagt gcctggcccg actcaagcct acgcttgcgg gccccacacc   5220
tctcctgtac cgtttgggcc ctattaccaa tgaggtcacc ctcacacacc ctgggacgaa   5280
gtacatcgcc acatgcatgc aagctgacct tgaggtcatg accagcacgt gggtcctagc   5340
tggaggagtc ctggcagccg tcgccgcata ttgcctggcg actggatgcg tttccatcat   5400
cggccgcttg cacgtcaacc agcgagtcgt cgttgcgccg gataaggagg tcctgtatga   5460
ggcttttgat gagatggagg aatgcgcctc tagggcggct ctcatcgaag aggggcagcg   5520
gatagccgag atgttgaagt ccaagatcca aggcttgctg cagcaggcct ctaagcaggc   5580
ccaggacata caacccgcta tgcaggcttc atggcccaaa gtggaacaat tttgggccag   5640
acacatgtgg aacttcatta gcggcatcca ataccctcgca ggattgtcaa cactgccagg   5700
gaaccccgcg gtggcttcca tgatggcatt cagtgccgcc ctcaccagtc cgttgtcgac   5760
cagtaccacc atccttctca acatcatggg aggctggtta gcgtcccaga tcgcaccacc   5820
cgcgggggcc accggctttg tcgtcagtgg cctggtgggg gctgccgtgg gcagcatagg   5880
cctgggtaag gtgctggtgg acatcctggc aggatatggt gcgggcattt cggggcccct   5940
cgtcgcattc aagatcatgt ctggcgagaa gcctctatg gaagatgtca tcaatctact   6000
gcctgggatc ctgtctccgg gagccctggt ggtgggggtc atctgcgcgg ccattctgcg   6060
ccgccacgtg ggaccggggg agggcgcggt ccaatggatg aacaggctta ttgcctttgc   6120
ttccagagga aaccacgtcg ccctactca ctacgtgacg gagtcggatg cgtcgcagcg   6180
tgtgacccaa ctacttggct ctcttactat aaccagccta ctcagaagac tccacaattg   6240
gataactgag gactgcccca tcccatgctc cggatcctgg ctccgcgacg tgtgggactg   6300
ggtttgcacc atcttgacag acttcaaaaa ttggctgacc tctaaattgt tccccaagct   6360
gcccggcctc cccttcatct cttgtcaaaa ggggtacaag ggtgtgtggg ccggcactgg   6420
catcatgacc acgcgctgcc cttgcggcgc aacatctct ggcaatgtcc gcctgggctc   6480
tatgaggatc acagggccta aaacctgcat gaacacctgg cagggacct ttcctatcaa   6540 ttgctacacg gagggccagt gcgcgccgaa accccccacg aactacaaga ccgccatctg   6600
gagggtggcg cctcggagt acgcggaggt gacgcagcat gggtcgtact cctatgtaac   6660
aggactgacc actgacaatc tgaaaattcc ttgccaacta ccttctccag agttttctc   6720 ctgggtggac ggtgtgcaga tccataggtt tgcacccaca ccaaagccgt ttttccggga   6780
tgaggtctcg ttctgcgttg ggcttaattc ctatgctgtc gggtcccagc ttccctgtga   6840
```

```
acctgagccc gacgcagacg tattgaggtc catgctaaca gatccgcccc acatcacggc    6900
ggagactgcg gcgcggcgct tggcacgggg atcacctcca tctgaggcga gctcctcagt    6960
gagccagcta tcagcaccgt cgctgcgggc cacctgcacc acccacagca acacctatga    7020
cgtggacatg gtcgatgcca acctgctcat ggagggcggt gtggctcaga cagagcctga    7080
gtccagggtg cccgttctgg actttctcga gccaatggcc gaggaagaga gcgaccttga    7140
gccctcaata ccatcggagt gcatgctccc caggagcggg tttccacggg ccttaccggc    7200
ttgggcacgg cctgactaca acccgccgct cgtggaatcg tggaggaggc cagattacca    7260 accgccacc gttgctggtt gtgctctccc cccccccaag aaggcccga cgcctccccc    7320 aaggagacgc cggacagtgg gtctgagcga gagcaccata tcagaagccc tccagcaact    7380
ggccatcaag acctttggcc agccccctc gagcggtgat gcaggctcgt ccacggggc    7440 gggcgccgcc gaatccggcg gtccgacgtc cctggtgag ccggcccct cagagacagg    7500 ttccgcctcc tctatgcccc ccctcgaggg ggagcctgga gatccggacc tggagtctga    7560
tcaggtagag cttcaacctc cccccaggg ggggggggta gctcccggtt cgggctcggg    7620
gtcttggtct acttgctccg aggaggacga taccaccgtg tgctgctcca tgtcatactc    7680
ctggaccggg gctctaataa ctccctgtag ccccgaagag gaaaagttgc caatcaaccc    7740
tttgagtaac tcgctgttgc gataccataa caaggtgtac tgtacaacat caagagcgc    7800 ctcacagagg gctaaaaagg taacttttga caggacgcaa gtgctcgacg cccattatga    7860
ctcagtctta aaggacatca agctagcggc ttcaaggtc agcgcaaggc tcctcacctt    7920
ggaggaggcg tgccagttga ctccacccca ttctgcaaga tccaagtatg gattcggggc    7980
caaggaggtc cgcagcttgt ccgggaggc cgttaaccac atcaagtccg tgtggaagga    8040
cctcctggaa gacccacaaa caccaattcc cacaaccatc atggccaaaa atgaggtgtt    8100
ctgcgtggac cccgccaagg ggggtaagaa accagctcgc ctcatcgttt accctgacct    8160
cggcgtccgg gtctgcgaga aaatggccct ctatgacatt acacaaaagc ttcctcaggc    8220
ggtaatggga gcttcctatg gcttccagta ctccctgcc caacgggtgg agtatctctt    8280
gaaagcatgg gcggaaaaga aggaccccat gggttttcg tatgataccc gatgcttcga    8340
ctcaaccgtc actgagagag acatcaggac cgaggagtcc atataccagg cctgctccct    8400
gcccgaggag gcccgcactg ccatacactc gctgactgag agactttacg taggagggcc    8460
catgttcaac agcaagggtc aaacctgcgg ttacagacgt tgccgcgcca gcgggtgct    8520 aaccactagc atgggtaaca ccatcacatg ctatgtgaaa gccctagcgg cctgcaaggc    8580
tgcggggata gttgcgccca caatgctggt atgcggcgat gacctagtag tcatctcaga    8640
aagccagggg actgaggagg acgagcggaa cctgagagcc ttcacggagg ccatgaccag    8700
gtactctgcc cctcctggtg atcccccag accggaatat gacctggagc taataacatc    8760
ctgttcctca aatgtgtctg tggcgttggg cccgcgggc cgccgcagat actacctgac    8820
cagagaccca accactccac tcgcccgggc tgcctgggaa acagttagac actcccctat    8880
caattcatgg ctgggaaaca tcatccagta tgctccaacc atatgggttc gcatggtcct    8940
aatgacacac ttcttctcca ttctcatggt ccaagacacc ctggaccaga acctcaactt    9000
tgagatgtat ggatcagtat actccgtgaa tcctttggac cttccagcca taattgagag    9060
gttacacggg cttgacgcct tttctatgca cacatactct caccacgaac tgacgcgggt    9120
ggcttcagcc ctcagaaaac ttgggcgcc accctcagg gtgtgaaga gtcgggctcg    9180 cgcagtcagg gcgtccctca tctcccgtgg agggaaagcg gccgtttgcg gccgatatct    9240
```

-continued

```
cttcaattgg gcggtgaaga ccaagctcaa actcactcca ttgccggagg cgcgcctact    9300
ggacttatcc agttggttca ccgtcggcgc cggcggggc gacattttc acagcgtgtc      9360 gcgcgcccga ccccgctcat tactcttcgg cctactccta cttttcgtag gggtaggcct    9420
cttcctactc cccgctcggt agagcggcac acactaggta cactccatag ctaactgttc    9480
cttttttttt tttttttttt tttttttttt tttttttttt ttttcttttt ttttttttc    9540 cctctttctt cccttctcat cttattctac tttctttctt ggtggctcca tcttagccct    9600
agtcacggct agctgtgaaa ggtccgtgag ccgcatgact gcagagagtg ccgtaactgg    9660
tctctctgca gatcatgtct aga                                             9683
```

<210> SEQ ID NO 3
<211> LENGTH: 30
<212> TYPE: DNA
<213> ORGANISM: Artificial
<220> FEATURE:
<223> OTHER INFORMATION: primer

<400> SEQUENCE: 3
cacaagcttg ccgaagtgaa gaacatcagt                                       30

<210> SEQ ID NO 4
<211> LENGTH: 32
<212> TYPE: DNA
<213> ORGANISM: Artificial
<220> FEATURE:
<223> OTHER INFORMATION: primer

<400> SEQUENCE: 4
gctctagatt aatgagcccc gctaatgatg tc                                    32

<210> SEQ ID NO 5
<211> LENGTH: 28
<212> TYPE: DNA
<213> ORGANISM: Artificial
<220> FEATURE:
<223> OTHER INFORMATION: primer

<400> SEQUENCE: 5
cacaagcttc gcacccatac tgttggggg                                        28

<210> SEQ ID NO 6
<211> LENGTH: 32
<212> TYPE: DNA
<213> ORGANISM: Artificial
<220> FEATURE:
<223> OTHER INFORMATION: primer

<400> SEQUENCE: 6
gctctagatt accatcggac gatgtatttt gt                                    32

<210> SEQ ID NO 7
<211> LENGTH: 162
<212> TYPE: PRT
<213> ORGANISM: Hepatitis C virus strain J6CF
<220> FEATURE:
<223> OTHER INFORMATION: E1(1-162)

<400> SEQUENCE: 7

Ala Glu Val Lys Asn Ile Ser Thr Gly Tyr Met Val Thr Asn Asp Cys
1               5                   10                  15

Thr Asn Asp Ser Ile Thr Trp Gln Leu Gln Ala Ala Val Leu His Val
            20                  25                  30

```
Pro Gly Cys Val Pro Cys Glu Lys Val Gly Asn Ala Ser Gln Cys Trp
            35                  40                  45
Ile Pro Val Ser Pro Asn Val Ala Val Gln Arg Pro Gly Ala Leu Thr
 50                  55                  60
Gln Gly Leu Arg Thr His Ile Asp Met Val Met Ser Ala Thr Leu
 65                  70                  75                  80
Cys Ser Ala Leu Tyr Val Gly Asp Leu Cys Gly Gly Val Met Leu Ala
                85                  90                  95
Ala Gln Met Phe Ile Val Ser Pro Gln His His Trp Phe Val Gln Asp
            100                 105                 110
Cys Asn Cys Ser Ile Tyr Pro Gly Thr Ile Thr Gly His Arg Met Ala
            115                 120                 125
Trp Asp Met Met Met Asn Trp Ser Pro Thr Ala Thr Met Ile Leu Ala
            130                 135                 140
Tyr Ala Met Arg Val Pro Glu Val Ile Ile Asp Ile Ile Ser Gly Ala
145                 150                 155                 160
His Trp

<210> SEQ ID NO 8
<211> LENGTH: 337
<212> TYPE: PRT
<213> ORGANISM: Hepatitis C virus strain J6CF
<220> FEATURE:
<223> OTHER INFORMATION: E2(1-337)

<400> SEQUENCE: 8

Arg Thr His Thr Val Gly Gly Ser Ala Ala Gln Thr Thr Gly Arg Leu
 1                   5                  10                  15
Thr Ser Leu Phe Asp Met Gly Pro Arg Gln Lys Ile Gln Leu Val Asn
                20                  25                  30
Thr Asn Gly Ser Trp His Ile Asn Arg Thr Ala Leu Asn Cys Asn Asp
            35                  40                  45
Ser Leu His Thr Gly Phe Ile Ala Ser Leu Phe Tyr Thr His Ser Phe
 50                  55                  60
Asn Ser Ser Gly Cys Pro Glu Arg Met Ser Ala Cys Arg Ser Ile Glu
 65                  70                  75                  80
Ala Phe Arg Val Gly Trp Gly Ala Leu Gln Tyr Glu Asp Asn Val Thr
                85                  90                  95
Asn Pro Glu Asp Met Arg Pro Tyr Cys Trp His Tyr Pro Pro Arg Gln
            100                 105                 110
Cys Gly Val Val Ser Ala Lys Thr Val Cys Gly Pro Val Tyr Cys Phe
            115                 120                 125
Thr Pro Ser Pro Val Val Gly Thr Thr Asp Arg Leu Gly Ala Pro
            130                 135                 140
Thr Tyr Thr Trp Gly Glu Asn Glu Thr Asp Val Phe Leu Leu Asn Ser
145                 150                 155                 160
Thr Arg Pro Pro Leu Gly Ser Trp Phe Gly Cys Thr Trp Met Asn Ser
                165                 170                 175
Ser Gly Tyr Thr Lys Thr Cys Gly Ala Pro Pro Cys Arg Thr Arg Ala
            180                 185                 190
Asp Phe Asn Ala Ser Thr Asp Leu Leu Cys Pro Thr Asp Cys Phe Arg
            195                 200                 205
Lys His Pro Asp Thr Thr Tyr Leu Lys Cys Gly Ser Gly Pro Trp Leu
            210                 215                 220
Thr Pro Arg Cys Leu Ile Asp Tyr Pro Tyr Arg Leu Trp His Tyr Pro
```

```
                    225                 230                 235                 240
Cys Thr Val Asn Tyr Thr Ile Phe Lys Ile Arg Met Tyr Val Gly Gly
                245                 250                 255
Val Glu His Arg Leu Thr Ala Ala Cys Asn Phe Thr Arg Gly Asp Arg
            260                 265                 270
Cys Asn Leu Glu Asp Arg Asp Arg Ser Gln Leu Ser Pro Leu Leu His
        275                 280                 285
Ser Thr Thr Glu Trp Ala Ile Leu Pro Cys Ser Tyr Ser Asp Leu Pro
    290                 295                 300
Ala Leu Ser Thr Gly Leu Leu His Leu His Gln Asn Ile Val Asp Val
305                 310                 315                 320
Gln Phe Met Tyr Gly Leu Ser Pro Ala Leu Thr Lys Tyr Ile Val Arg
                325                 330                 335
Trp

<210> SEQ ID NO 9
<211> LENGTH: 473
<212> TYPE: DNA
<213> ORGANISM: Mus musculus
<220> FEATURE:
<223> OTHER INFORMATION: P18-9E immunoglobulin gamma 2b chain variable
      region

<400> SEQUENCE: 9
atggaatgga gctgggttat cctcttcctc ctgtcattaa ctgcaggtgt cgatgcccag      60
ggtcagatgc agcaatctgg acctgagctg gtgaagcctg ggcttcagt gaagctgtcc     120 tgcaagacta ctgacttcac cttcaacagg aactacataa gttggttgag caaaagcct     180 ggacagagcc ttgagtggat tgcatggatt tatgctggaa ctggtggtac taagtataat     240
cagaaattca caggcaaggc ccaaatgact gtagacacat catcccacac agcctacatg     300
caattcagca acctgacaac tgaggactct gccgtctatt actgtgcacg atatctcttt     360
gatggttact acattcccct cttttgactac tggggtcaag gcaccactct cacagtctcc     420
tcagccaaaa caacaccccc acccgtctat ccctggccc ctggaagctt ggg              473

<210> SEQ ID NO 10
<211> LENGTH: 477
<212> TYPE: DNA
<213> ORGANISM: Mus musculus
<220> FEATURE:
<223> OTHER INFORMATION: P18-9E immunoglobulin kappa chain variable
      region

<400> SEQUENCE: 10
atgaggtccc cggctcagct tctgccagga cacagtttag atatgaggtt ccaggttcag      60
gttctggggc tccttctgct ctggatatca ggtgcccagt gtgatgtcca gataacccag     120
tctccatctt atcttgctgc atctcctgga gaaaccattt ctattaattg cagggcaaat     180
aagagcattg acaaatattt agcctggtat caagagaaac ctgggaaaac taataaactt     240
cttatctact ctggatccac tttacaatct ggagttccat caaagttcag tggcagtgga     300
tctggtacag atttcactct caccatcagt agcctggagc tgaagatttt gcaatgtat     360 tattgtcaac aacataatga ataccgctc acgttcggtg ctgggaccaa gctggacctg     420
agacgggctg atgctgcacc aactgtatcc atcttccac catccagtaa gcttggg         477

<210> SEQ ID NO 11
<211> LENGTH: 457
<212> TYPE: DNA
```

<213> ORGANISM: Mus musculus
<220> FEATURE:
<223> OTHER INFORMATION: P19-7D immunoglobulin gamma 1 chain variable
      region

<400> SEQUENCE: 11
atggctgtct tagggctgtt cttctgcctg gtgacattcc caagctgtgt cctgtcccag      60
gtgcagctga agcagtcagg acctggccta gtgcagccct cacagagcct gtccataacc     120
tgcacagtct ctggtttctc attaactacc tatggtgtac actgggttcg ccagtctcca     180
ggaaagggtc tggagtggct gggagtgata tggagaggtg aagcacaga ctacaatgca      240 gctttcttgt ccagactgag catcaccaag gacaattcca agagccaagt tttctttaaa     300
atgaacagtc tgcaacctga tgacactgcc atatactact gtgccaaaaa ttcctgggac     360
ggggcttact ggggccaagg gactctggtc actgtctctg cagccaaaac gacacccca      420 cccgtttatc ccctggcccc tggaagcttg gaaggg                                457

<210> SEQ ID NO 12
<211> LENGTH: 447
<212> TYPE: DNA
<213> ORGANISM: Mus musculus
<220> FEATURE:
<223> OTHER INFORMATION: P19-7D immunoglobulin kappa chain variable
      region

<400> SEQUENCE: 12
atgaagttgc ctgttaggct gttggtgctg atgttctgga ttcctgcttc cagcagtgat      60
gttgtgatga cccaaactcc actctccctg cctgtcagtc ttggagatca agcctccatc     120
tcttgcagat ctagtcagag cctttttaca gtaatggaa acaccttatt acattggtac      180
ctgcagaagc caggccagtc tccaaagctc ctgatctaca agtttccaa ccgatttttct     240 ggggtcccag acaggttcag tgcagtggga tcagggacag atttcacact caagatcagc     300
agagtggagg ctgaggatct gggactatat ttctgctctc aaaatacaca ttttccgtgg     360
acgttcggtg aggcaccga gctggaaatc agtcgggctg atgctgcacc aactgtatcc      420
atcttcccac catccagtaa gcttggg                                          447

<210> SEQ ID NO 13
<211> LENGTH: 157
<212> TYPE: PRT
<213> ORGANISM: Mus musculus
<220> FEATURE:
<223> OTHER INFORMATION: P18-9E immunoglobulin gamma 2b chain variable
      region

<400> SEQUENCE: 13

Met Glu Trp Ser Trp Val Ile Leu Phe Leu Leu Ser Leu Thr Ala Gly
1               5                   10                  15

Val Asp Ala Gln Gly Gln Met Gln Gln Ser Gly Pro Glu Leu Val Lys
            20                  25                  30

Pro Gly Ala Ser Val Lys Leu Ser Cys Lys Thr Thr Asp Phe Thr Phe
        35                  40                  45

Asn Arg Asn Tyr Ile Ser Trp Leu Arg Gln Lys Pro Gly Gln Ser Leu
    50                  55                  60

Glu Trp Ile Ala Trp Ile Tyr Ala Gly Thr Gly Gly Thr Lys Tyr Asn
65                  70                  75                  80

Gln Lys Phe Thr Gly Lys Ala Gln Met Thr Val Asp Thr Ser Ser His
                85                  90                  95

Thr Ala Tyr Met Gln Phe Ser Asn Leu Thr Thr Glu Asp Ser Ala Val

```
                    100                 105                 110
Tyr Tyr Cys Ala Arg Tyr Leu Phe Asp Gly Tyr Ile Pro Leu Phe
        115                 120                 125

Asp Tyr Trp Gly Gln Gly Thr Thr Leu Thr Val Ser Ser Ala Lys Thr
        130                 135                 140

Thr Pro Pro Val Tyr Pro Leu Ala Pro Gly Ser Leu
145                 150                 155

<210> SEQ ID NO 14
<211> LENGTH: 159
<212> TYPE: PRT
<213> ORGANISM: Mus musculus
<220> FEATURE:
<223> OTHER INFORMATION: P18-9E immunoglobulin kappa chain variable
      region

<400> SEQUENCE: 14

Met Arg Ser Pro Ala Gln Leu Leu Pro Gly His Ser Leu Asp Met Arg
1               5                   10                  15

Phe Gln Val Gln Val Leu Gly Leu Leu Leu Trp Ile Ser Gly Ala
            20                  25                  30

Gln Cys Asp Val Gln Ile Thr Gln Ser Pro Ser Tyr Leu Ala Ala Ser
        35                  40                  45

Pro Gly Glu Thr Ile Ser Ile Asn Cys Arg Ala Asn Lys Ser Ile Asp
50                  55                  60

Lys Tyr Leu Ala Trp Tyr Gln Glu Lys Pro Gly Lys Thr Asn Lys Leu
65                  70                  75                  80

Leu Ile Tyr Ser Gly Ser Thr Leu Gln Ser Gly Val Pro Ser Lys Phe
                85                  90                  95

Ser Gly Ser Gly Ser Gly Thr Asp Phe Thr Leu Thr Ile Ser Ser Leu
            100                 105                 110

Glu Pro Glu Asp Phe Ala Met Tyr Tyr Cys Gln Gln His Asn Glu Tyr
        115                 120                 125

Pro Leu Thr Phe Gly Ala Gly Thr Lys Leu Asp Leu Arg Arg Ala Asp
    130                 135                 140

Ala Ala Pro Thr Val Ser Ile Phe Pro Pro Ser Ser Lys Leu Gly
145                 150                 155

<210> SEQ ID NO 15
<211> LENGTH: 140
<212> TYPE: PRT
<213> ORGANISM: Mus musculus
<220> FEATURE:
<223> OTHER INFORMATION: P19-7D immunoglobulin gamma 1 chain variable
      region

<400> SEQUENCE: 15

Met Ala Val Leu Gly Leu Phe Phe Cys Leu Val Thr Phe Pro Ser Cys
1               5                   10                  15

Val Leu Ser Gln Pro Ser Gln Ser Leu Ser Ile Thr Cys Thr Val Ser
            20                  25                  30

Gly Phe Ser Leu Thr Thr Tyr Gly Val His Trp Val Arg Gln Ser Pro
        35                  40                  45

Gly Lys Gly Leu Glu Trp Leu Gly Val Ile Trp Arg Gly Gly Ser Thr
    50                  55                  60

Asp Tyr Asn Ala Ala Phe Leu Ser Arg Leu Ser Ile Thr Lys Asp Asn
65                  70                  75                  80

Ser Lys Ser Gln Val Phe Phe Lys Met Asn Ser Leu Gln Pro Asp Asp
            85                  90                  95
```

-continued

Thr Ala Ile Tyr Tyr Cys Ala Lys Asn Ser Trp Asp Gly Ala Tyr Trp
            100                 105                 110

Gly Gln Gly Thr Leu Val Thr Val Ser Ala Ala Lys Thr Thr Pro Pro
        115                 120                 125

Pro Val Tyr Pro Leu Ala Pro Gly Ser Leu Gly Arg
        130                 135                 140

<210> SEQ ID NO 16
<211> LENGTH: 149
<212> TYPE: PRT
<213> ORGANISM: Mus musculus
<220> FEATURE:
<223> OTHER INFORMATION: P19-7D kappa chain variable region

<400> SEQUENCE: 16

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Leu His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Leu Tyr Phe Cys
            100                 105                 110

Ser Gln Asn Thr His Phe Pro Trp Thr Phe Gly Gly Gly Thr Glu Leu
        115                 120                 125

Glu Ile Ser Arg Ala Asp Ala Ala Pro Thr Val Ser Ile Phe Pro Pro
    130                 135                 140

Ser Ser Lys Leu Gly
145

<210> SEQ ID NO 17
<211> LENGTH: 32
<212> TYPE: PRT
<213> ORGANISM: Homo sapiens
<220> FEATURE:
<223> OTHER INFORMATION: immunoglobulin gamma 2b chain variable region
      FR1

<400> SEQUENCE: 17

Asp Ala Gln Gly Gln Met Gln Gln Ser Gly Pro Glu Leu Val Lys Pro
1               5                   10                  15

Gly Ala Ser Val Lys Leu Ser Cys Lys Thr Thr Asp Phe Thr Phe Asn
            20                  25                  30

<210> SEQ ID NO 18
<211> LENGTH: 5
<212> TYPE: PRT
<213> ORGANISM: Mus musculus
<220> FEATURE:
<223> OTHER INFORMATION: P18-9E immunoglobulin gamma 2b chain variable
      region CDR1

<400> SEQUENCE: 18

Arg Asn Tyr Ile Ser
1               5

```
<210> SEQ ID NO 19
<211> LENGTH: 14
<212> TYPE: PRT
<213> ORGANISM: Homo sapiens
<220> FEATURE:
<223> OTHER INFORMATION: immunoglobulin gamma 2b chain variable region
      FR2

<400> SEQUENCE: 19

Trp Leu Arg Gln Lys Pro Gly Gln Ser Leu Glu Trp Ile Ala
1               5                   10

<210> SEQ ID NO 20
<211> LENGTH: 17
<212> TYPE: PRT
<213> ORGANISM: Mus musculus
<220> FEATURE:
<223> OTHER INFORMATION: P18-9E immunoglobulin gamma 2b chain variable
      region CDR2

<400> SEQUENCE: 20

Trp Ile Tyr Ala Gly Thr Gly Gly Thr Lys Tyr Asn Gln Lys Phe Thr
1               5                   10                  15

Gly

<210> SEQ ID NO 21
<211> LENGTH: 32
<212> TYPE: PRT
<213> ORGANISM: Homo sapiens
<220> FEATURE:
<223> OTHER INFORMATION: immunoglobulin gamma 2b chain variable region
      FR3

<400> SEQUENCE: 21

Lys Ala Gln Met Thr Val Asp Thr Ser Ser His Thr Ala Tyr Met Gln
1               5                   10                  15

Phe Ser Asn Leu Thr Thr Glu Asp Ser Ala Val Tyr Tyr Cys Ala Arg
            20                  25                  30

<210> SEQ ID NO 22
<211> LENGTH: 13
<212> TYPE: PRT
<213> ORGANISM: Mus musculus
<220> FEATURE:
<223> OTHER INFORMATION: P18-9E immunoglobulin gamma 2b chain variable
      region CDR3

<400> SEQUENCE: 22

Tyr Leu Phe Asp Gly Tyr Tyr Ile Pro Leu Phe Asp Tyr
1               5                   10

<210> SEQ ID NO 23
<211> LENGTH: 10
<212> TYPE: PRT
<213> ORGANISM: Homo sapiens
<220> FEATURE:
<223> OTHER INFORMATION: immunoglobulin gamma 2b chain variable region
      FR4

<400> SEQUENCE: 23

Trp Gly Gln Gly Thr Thr Leu Thr Val Ser
1               5                   10

<210> SEQ ID NO 24
<211> LENGTH: 26
<212> TYPE: PRT
```

-continued

```
<213> ORGANISM: Homo sapiens
<220> FEATURE:
<223> OTHER INFORMATION: immunoglobulin gamma kappa chain variable
      region FR1

<400> SEQUENCE: 24

Ala Gln Cys Asp Val Gln Ile Thr Gln Ser Pro Ser Tyr Leu Ala Ala
1               5                  10                  15

Ser Pro Gly Glu Thr Ile Ser Ile Asn Cys
            20                  25

<210> SEQ ID NO 25
<211> LENGTH: 11
<212> TYPE: PRT
<213> ORGANISM: Mus musculus
<220> FEATURE:
<223> OTHER INFORMATION: P18-9E immunoglobulin kappa chain CDR1 variable
      region CDR1

<400> SEQUENCE: 25

Arg Ala Asn Lys Ser Ile Asp Lys Tyr Leu Ala
1               5                  10

<210> SEQ ID NO 26
<211> LENGTH: 15
<212> TYPE: PRT
<213> ORGANISM: Homo sapiens
<220> FEATURE:
<223> OTHER INFORMATION: immunoglobulin gamma kappa chain variable
      region FR2

<400> SEQUENCE: 26

Trp Tyr Gln Glu Lys Pro Gly Lys Thr Asn Lys Leu Leu Ile Tyr
1               5                  10                  15

<210> SEQ ID NO 27
<211> LENGTH: 7
<212> TYPE: PRT
<213> ORGANISM: Mus musculus
<220> FEATURE:
<223> OTHER INFORMATION: P18-9E immunoglobulin kappa chain CDR1 variable
      region CDR2

<400> SEQUENCE: 27

Ser Gly Ser Thr Leu Gln Ser
1               5

<210> SEQ ID NO 28
<211> LENGTH: 32
<212> TYPE: PRT
<213> ORGANISM: Homo sapiens
<220> FEATURE:
<223> OTHER INFORMATION: immunoglobulin gamma kappa chain variable
      region FR3

<400> SEQUENCE: 28

Gly Val Pro Ser Lys Phe Ser Gly Ser Gly Ser Gly Thr Asp Phe Thr
1               5                  10                  15

Leu Thr Ile Ser Ser Leu Glu Pro Glu Asp Phe Ala Met Tyr Tyr Cys
            20                  25                  30

<210> SEQ ID NO 29
<211> LENGTH: 9
<212> TYPE: PRT
<213> ORGANISM: Mus musculus
```

```
<220> FEATURE:
<223> OTHER INFORMATION: P18-9E immunoglobulin kappa chain CDR1 variable
      region CDR3

<400> SEQUENCE: 29

Gln Gln His Asn Glu Tyr Pro Leu Thr
1               5

<210> SEQ ID NO 30
<211> LENGTH: 11
<212> TYPE: PRT
<213> ORGANISM: Homo sapiens
<220> FEATURE:
<223> OTHER INFORMATION: immunoglobulin gamma kappa chain variable
      region FR4

<400> SEQUENCE: 30

Phe Gly Ala Gly Thr Lys Leu Asp Leu Arg Arg
1               5                   10

<210> SEQ ID NO 31
<211> LENGTH: 20
<212> TYPE: PRT
<213> ORGANISM: Homo sapiens
<220> FEATURE:
<223> OTHER INFORMATION: immunoglobulin gamma 1 chain variable region
      FR1

<400> SEQUENCE: 31

Leu Ser Gln Pro Ser Gln Ser Leu Ser Ile Thr Cys Thr Val Ser Gly
1               5                   10                  15

Phe Ser Leu Thr
            20

<210> SEQ ID NO 32
<211> LENGTH: 5
<212> TYPE: PRT
<213> ORGANISM: Mus musculus
<220> FEATURE:
<223> OTHER INFORMATION: P19-7D immunoglobulin gamma 1 chain variable
      region CDR1

<400> SEQUENCE: 32

Thr Tyr Gly Val His
1               5

<210> SEQ ID NO 33
<211> LENGTH: 14
<212> TYPE: PRT
<213> ORGANISM: Homo sapiens
<220> FEATURE:
<223> OTHER INFORMATION: immunoglobulin gamma 1 chain variable region
      FR2

<400> SEQUENCE: 33

Trp Val Arg Gln Ser Pro Gly Lys Gly Leu Glu Trp Leu Gly
1               5                   10

<210> SEQ ID NO 34
<211> LENGTH: 16
<212> TYPE: PRT
<213> ORGANISM: Mus musculus
<220> FEATURE:
<223> OTHER INFORMATION: P19-7D immunoglobulin gamma 1 chain variable
      region CDR2

<400> SEQUENCE: 34
```

Val Ile Trp Arg Gly Gly Ser Thr Asp Tyr Asn Ala Ala Phe Leu Ser
1               5                   10                  15

<210> SEQ ID NO 35
<211> LENGTH: 33
<212> TYPE: PRT
<213> ORGANISM: Homo sapiens
<220> FEATURE:
<223> OTHER INFORMATION: immunoglobulin gamma 1 chain variable region
      FR3

<400> SEQUENCE: 35

Arg Leu Ser Ile Thr Lys Asp Asn Ser Lys Ser Gln Val Phe Phe Lys
1               5                   10                  15

Met Asn Ser Leu Gln Pro Asp Asp Thr Ala Ile Tyr Tyr Cys Ala Lys
            20                  25                  30

Asn

<210> SEQ ID NO 36
<211> LENGTH: 6
<212> TYPE: PRT
<213> ORGANISM: Mus musculus
<220> FEATURE:
<223> OTHER INFORMATION: P19-7D immunoglobulin gamma 1 chain variable
      region CDR3

<400> SEQUENCE: 36

Ser Trp Asp Gly Ala Tyr
1               5

<210> SEQ ID NO 37
<211> LENGTH: 10
<212> TYPE: PRT
<213> ORGANISM: Homo sapiens
<220> FEATURE:
<223> OTHER INFORMATION: immunoglobulin gamma 1 chain variable region
      FR4

<400> SEQUENCE: 37

Trp Gly Gln Gly Thr Leu Val Thr Val Ser
1               5                   10

<210> SEQ ID NO 38
<211> LENGTH: 26
<212> TYPE: PRT
<213> ORGANISM: Homo sapiens
<220> FEATURE:
<223> OTHER INFORMATION: immunoglobulin gamma 1 light chain variable
      region FR1

<400> SEQUENCE: 38

Ser Ser Ser Asp Val Val Met Thr Gln Thr Pro Leu Ser Leu Pro Val
1               5                   10                  15

Ser Leu Gly Asp Gln Ala Ser Ile Ser Cys
            20                  25

<210> SEQ ID NO 39
<211> LENGTH: 16
<212> TYPE: PRT
<213> ORGANISM: Mus musculus
<220> FEATURE:
<223> OTHER INFORMATION: P19-7D immunoglobulin gamma kappa chain
      variable region CDR1

<400> SEQUENCE: 39

Arg Ser Ser Gln Ser Leu Leu His Ser Asn Gly Asn Thr Tyr Leu His

```
<210> SEQ ID NO 40
<211> LENGTH: 15
<212> TYPE: PRT
<213> ORGANISM: Homo sapiens
<220> FEATURE:
<223> OTHER INFORMATION: immunoglobulin gamma 1 light chain variable
      region FR2

<400> SEQUENCE: 40

Trp Tyr Leu Gln Lys Pro Gly Gln Ser Pro Lys Leu Leu Ile Tyr
1               5                   10                  15

<210> SEQ ID NO 41
<211> LENGTH: 7
<212> TYPE: PRT
<213> ORGANISM: Mus musculus
<220> FEATURE:
<223> OTHER INFORMATION: P19-7D immunoglobulin gamma kappa chain
      variable region CDR2

<400> SEQUENCE: 41

Lys Val Ser Asn Arg Phe Ser
1               5

<210> SEQ ID NO 42
<211> LENGTH: 32
<212> TYPE: PRT
<213> ORGANISM: Homo sapiens
<220> FEATURE:
<223> OTHER INFORMATION: immunoglobulin gamma 1 light chain variable
      region FR3

<400> SEQUENCE: 42

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Leu Tyr Phe Cys
            20                  25                  30

<210> SEQ ID NO 43
<211> LENGTH: 9
<212> TYPE: PRT
<213> ORGANISM: Mus musculus
<220> FEATURE:
<223> OTHER INFORMATION: P19-7D immunoglobulin gamma kappa chain
      variable region CDR3

<400> SEQUENCE: 43

Ser Gln Asn Thr His Phe Pro Trp Thr
1               5

<210> SEQ ID NO 44
<211> LENGTH: 11
<212> TYPE: PRT
<213> ORGANISM: Homo sapiens
<220> FEATURE:
<223> OTHER INFORMATION: immunoglobulin gamma 1 light chain variable
      region FR4

<400> SEQUENCE: 44

Phe Gly Gly Gly Thr Glu Leu Glu Ile Ser Arg
1               5                   10
```

ANTIBODY HAVING ACTIVITY OF INHIBITING HEPATITIS C VIRUS (HCV) INFECTION AND USE THEREOF

TECHNICAL FIELD

The present invention relates to an antibody having activity of inhibiting hepatitis C virus (HCV) infection and use thereof.

BACKGROUND ART

The hepatitis C virus (which may be abbreviated as "HCV" hereinafter) is an RNA virus that is classified as a member of the genus *Hepacivirus* of the family Flaviviridae. It has been identified as a major causative virus of non-A and non-B hepatitis (non-patent document 1). The HCV genome encodes a precursor protein that is converted into 10 types of virus protein (i.e., Core, E1, E2, p7, NS2, NS3, NS4A, NS4B, NS5A, and NS5B) via post-translational cleavage by host-derived signal peptidase or HCV-derived proteases. Of these virus proteins, Core, E1, E2, and p7 proteins are classified as structural proteins, and NS2, NS3, NS4A, NS4B, NS5A, and NS5B proteins are classified as non-structural proteins.

HCV is mainly transmitted via blood transfusion. Highly sensitive methods for detecting HCV have been established today, and the number of new HCV patients because of blood transfusion has dramatically decreased. However, at present, the number of HCV carriers including so-called virus carriers who have not yet developed hepatitis symptoms is deduced to be over 2,000,000 in Japan, and is over 170,000,000 in the world. This is mainly because the rate of chronicity of hepatitis due to HCV infection is as high as 70% to 80% and there are no effective antiviral agents other than interferons at present. Further, chronic hepatitis C caused by HCV infection would become worse and lead to cirrhosis during the following some 20 years, finally resulting in liver cancer. Further, liver cancer is known to result in relapse for many patients due to inflammation that continuously occurs at noncancerous parts even if cancer is surgically excised.

Therefore, development of antiviral drugs and vaccines with beneficial effects has been desired for the purpose of preventing virus carriers from developing the disease and eliminating viruses. For this purpose, detailed information about the HCV life cycle should be clarified, such as regarding the ways in which HCV invades, replicates, grows in host cells, and HCV affects host cells.

The HCV life cycle involves the series of cycles described below. First, HCV binds to a specific protein (virus receptor) on the cell surface and is incorporated by endocytosis into the host cell. Next, HCV genomic RNA is released into the host cytoplasm from viral particles (uncoating). Subsequently, HCV protein precursors encoded by the released HCV genomic RNA are translated. After each virus protein has been generated by processing, the HCV genomic RNA is replicated by RNA polymerase, which is one of the generated virus proteins. The thus replicated HCV genomic RNA is packaged by the Core protein and envelope proteins (E1 protein and E2 protein), which are structural proteins, so that new viral particles are formed. Finally, viral particles break the host cell membranes and are then released from the cells.

Therefore, it is important to develop a method for inhibiting at least one of the above steps in the process of HCV infection, in order to prevent HCV carriers from developing the disease and to eliminate the virus.

HCV envelope proteins are considered to play a key role in the binding of HCV to cell surfaces. Thus, research has been conducted for preparation of antibodies against envelope proteins in blood serum samples of HCV patients. However, the percentage of HCV patients exhibiting positive reactions with either the C100 antibody (the NS4-NS-5 antibody) or the anti-core antibody, both of them or an anti-envelope protein antibody was found to be approximately 10%. Since only about 10% of HCV patients are naturally cured with a neutralizing antibody (non-patent document 2), it is thought that as few as 1% of all patients who are thought to be cured by the anti-envelope protein antibody. This is thought to be due to the presence of a mechanism that inhibits or suppresses the production of antibodies against HCV envelope proteins (non-patent document 3)

Meanwhile, non-patent document 4 discloses that when one of the HCV envelope proteins, the E2 protein, is expressed in a mammal, the E2 protein specifically binds to CD81 existing on human cell surfaces. Based on the experimental result, isolation of an antibody that exhibits NOB (neutralization of binding) activity that inhibits the binding between the E2 protein and CD81 from a hepatitis C patient has been attempted. For example, through construction of an antibody gene library from the bone-marrow lymphocytes of a chronic hepatitis C patient affected by HCV of genotype 1a, followed by employment of a phage display method, the above antibody has been isolated (patent document 1). Moreover, an antibody exhibiting NOB activity has also been isolated by a method for preparing hybridomas from peripheral B cells of a hepatitis C patient affected by HCV of genotype 1b (non-patent document 5 and patent document 2). However, with methods for preparing monoclonal antibodies from HCV patients, it is difficult to obtain a variety of repertoires of infection-inhibiting antibodies and to find antibodies useful as anti-HCV agents, since only the patients having HCV infection-inhibiting antibodies can be used herein. Also, it has been reported that an antibody exhibiting NOB activity does not always inhibit infection (non-patent document 8).

Furthermore, a method that involves inducing an antibody via administration of a recombinant envelope protein to a mouse (patent document 3) and a method that involves fusing lymphocytes to myeloma cells to prepare antibody-producing hybridomas (thus preparing an antibody against an envelope protein) have been attempted (patent document 4 and non-patent document 6). However, no effective antibody inhibiting HCV infection has been obtained to date. No antibody neutralizing HCV infection has been prepared by immunizing an animal with an envelope protein. One of the suggested reasons for this lack is that a recombinant envelope protein to be used for immunization has a structure differing from that of the virus's original envelope protein. It has also been reported that recombinant envelope proteins tend to aggregate so that they are unable to maintain their original conformations (non-patent document 7).

Therefore, in view of treatment and prevention using HCV antibodies, development of antibodies against envelope proteins that are capable of inhibiting viral infection and a new method for effectively inducing such antibodies have been desired.

Starting from the above background, technique for preparing infectious HCV particles with a cell culture system has been recently established (patent documents 5, 6, and 7). Unlike the above method, which involves causing the expression of a recombinant envelope protein by gene recombination techniques and using the resultant as an antigen, HCV particles prepared using such a cell culture system are infectious, and thus the conformation of the HCV antigen may be maintained.

The conformation of HCV is composed of an envelope comprising envelope proteins (E1 protein and E2 protein) and a lipid membrane. These E1 and E2 proteins are thought to bind to each other, forming a complex (non-patent document 7).

On the other hand, envelope proteins of an AIDS virus form a trimer. It has been revealed that an antibody recognizing the conformation of the trimer as an epitope (antigenic determinant) is effective against a wide range of AIDS viruses, compared with conventional anti-AIDS virus antibodies, and has high neutralization activity. This suggests that it is important for an antibody with such neutralization activity to be able to recognize the conformation of a viral antigen as an epitope (non-patent document 9).

PRIOR ART DOCUMENTS

Patent Documents

Patent document 1 JP Patent Publication (Kohyo) No. 2005-531286 A
Patent document 2 JP Patent Publication (Kohyo) No. 2006-504645A
Patent document 3 JP Patent Publication (Kohyo) No. 2004-500366 A
Patent document 4 JP Patent Publication (Kohyo) No. 6-505389 A (1994)
Patent document 5 WO05080575A1
Patent document 6 WO06022422A1
Patent document 7 WO06096459A2
Non-patent document 1 Choo et al., Science, 1989, Vol. 244, p. 359-362
Non-patent document 2 Matsuura et al., J. Virol., 1992, Vol. 66, p. 1425-1431
Non-patent document 3 Saito et al., Experimental Medicine (JIKKEN-IGAKU; Japanese), 1991, Vol. 9, p. 2075-2080
Non-patent document 4 Pileri et al., Science, 1998, Vol. 282, p. 938-941
Non-patent document 5 Hadlock et al., J. Virol., 2000, Vol. 74, p. 10407-10416
Non-patent document 6 Suzuki et al., SAISHIN IGAKU (Japanese), 2003, Vol. 58, p. 2017-2022
Non-patent document 7 Op de Beeck et al., J. Gen. Virol., 2001, Vol. 82, p. 2589-2595
Non-patent document 8 Burioni et al., J. Virol., 2002, Vol. 76, p. 11775-11779
Non-patent document 9 Laura M. Walker et al., Science, 2009, Vol. 326, p. 285

SUMMARY OF THE INVENTION

Problem to be Solved by the Invention

An object of the present invention is to provide an antibody inhibiting HCV infection.

Means for Solving the Problem

As a result of intensive studies, the present inventors have succeeded in obtaining a plurality of monoclonal antibodies having activity of inhibiting HCV infection from antibody-producing hybridomas prepared from mice to which infectious HCV particles have been administered. These monoclonal antibodies are anti-HCV antibodies that recognize the conformation of a complex consisting of the HCV E1 protein and E2 protein, as an epitope. Such antibodies capable of recognizing such a conformation as an epitope are predicted to be effective against a wide range of HCV and not to lose the infection-inhibiting capacity due to HCV mutation. The present invention has been completed based on these findings, encompassing the following (1) to (24).

(1) An anti-HCV antibody, which recognizes as an epitope the conformation of a complex consisting of an E1 protein and an E2 protein of HCV particles, and has activity of inhibiting infection with HCV.
(2) The anti-HCV antibody according to (1), wherein the amino acid sequences of the E1 protein and the E2 protein contain the amino acid sequences shown in SEQ ID NO: 7 and SEQ ID NO: 8, respectively, in the sequence listing.
(3) The anti-HCV antibody according to (1) or (2), wherein the HCV particles are produced from a chimeric HCV genome composed by connecting portions of the genome of the HCV J6CF strain and JFH-1 strain, and the chimeric HCV genome is the following (i) or (ii):
(i) a chimeric HCV genome, in which 5' untranslated region, core protein-coding sequence, E1 protein-coding sequence, E2 protein-coding sequence, and p7 protein-coding sequence derived from J6CF strain, NS2 protein-coding sequence, NS3 protein-coding sequence, NS4A protein-coding sequence, NS4B protein-coding sequence, NS5A protein-coding sequence, NS5B protein-coding sequence, and the 3' untranslated region derived from the JFH-1 strain are connected from the 5' side in this order; or
(ii) a chimeric HCV genome, in which 5' untranslated region, core protein-coding sequence, E1 protein-coding sequence, E2 protein-coding sequence, p7 protein-coding sequence, and the amino acid sequence encoding $16^{th}$ amino acid residues from the N-terminus of an NS2 protein-coding region derived from the J6CF strain, amino acid sequence following the $17^{th}$ amino acid residue from the N-terminus to the C-terminal amino acid residue of the NS2 protein-coding region, NS3 protein-coding sequence, NS4A protein-coding sequence, NS4B protein-coding sequence, NS5A protein-coding sequence, NS5B protein-coding sequence, and the 3'untranslated region derived from the JFH-1 strain are connected from the 5' side in this order.
(4) The anti-HCV antibody according to (3), wherein the chimeric HCV genome is a nucleic acid consisting of the nucleotide sequence shown in SEQ ID NO: 2 in the sequence listing (and when the nucleic acid is RNA, thymine (T) in the nucleotide sequence is read as uracil (U)).
(5) The anti-HCV antibody according to any one of (1) to (4) above, wherein the activity of inhibiting HCV infection is to inhibit the binding of an HCV particle to the surface of a host cell.
(6) The anti-HCV antibody according to any one of (1) to (5) above, which is produced by a hybridoma cell line deposited under Accession No. FERM BP-11263.
(7) The anti-HCV antibody according to any one of (1) to (5) above, which is produced by a hybridoma cell line deposited under Accession No. FERM BP-11264.
(8) The anti-HCV antibody according to any one of (1) to (5) above, which is a humanized antibody.
(9) A hybridoma cell line, the Accession No. of which is FERM BP-11263.
(10) A hybridoma cell line, the Accession No. of which is FERM BP-11264.
(11) An inhibitory agent for HCV infection, comprising the anti-HCV antibody according to any one of (1) to (8) above as an active ingredient.
(12) The anti-HCV antibody according to any one of (1) to (5) above, comprising a heavy chain variable region that contains a complementarity determining region containing the amino acid sequences shown in SEQ ID NOs: 18, 20, and 22 in the sequence listing.
(13) The anti-HCV antibody according to (12) above, comprising a heavy chain variable region that contains the amino acid sequence shown in SEQ ID NO: 13 in the sequence listing.
(14) The anti-HCV antibody according to (1), (2), (3), (4), (5), (12), or (13) above, comprising a light chain variable region that contains a complementarity determining region containing the amino acid sequences shown in SEQ ID NO: 25, 27, and 29 in the sequence listing.
(15) The anti-HCV antibody according to (14) above, comprising a light chain variable region that contains the amino acid sequence shown in SEQ ID NO: 14 in the sequence listing.
(16) The anti-HCV antibody according to any one of (1) to (5) above, comprising a heavy chain variable region that contains a complementarity determining region containing the amino acid sequences shown in SEQ ID NOs: 32, 34, and 36 in the sequence listing.
(17) The anti-HCV antibody according to (16) above, comprising a heavy chain variable region that contains the amino acid sequence shown in SEQ ID NO: 15 in the sequence listing.
(18) The anti-HCV antibody according to (1), (2), (3), (4), (5), (16), or (17) above, having a light chain variable region that contains a complementarity determining region containing the amino acid sequences shown in SEQ ID NO: 39, 41, and 43 in the sequence listing.
(19) The anti-HCV antibody according to (18) above, having a light chain variable region that contains the amino acid sequence shown in SEQ ID NO: 16 in the sequence listing.
(20) The antibody according to (12) to (19) above, 1 to 5 amino acids in a framework region are deleted, substituted, inserted, or added in the amino acid sequence of the above heavy chain variable region or light chain variable region.
(21) The anti-HCV antibody according to any one of (12) to (20) above, which is a humanized antibody.
(22) A fragment of the anti-HCV antibody according to (1), (2), (3), (4), (5), (6), (7), (8), (12), (13), (14), (15), (16), (17), (18), (19), (20), or (21) above, which recognizes as an epitope the conformation of a complex of the E1 protein and the E2 protein of HCV particles and has activity of inhibiting HCV infection.
(23) A polynucleotide, encoding the antibody according to (1), (2), (3), (4), (5), (6), (7), (8), (12), (13), (14), (15), (16), (17), (18), (19), (20), or (21) or a fragment of the antibody according to (22) above.
(24) A vector containing the polynucleotide according to (23) above.

This description includes the contents of the descriptions and/or drawings of Japanese Patent Application Nos. 2009-251165 and 2009-251341, which are priority documents of the present application.

Effects Of The Invention

The antibody having the activity of inhibiting HCV infection of the present invention and use thereof can be used for treating or preventing hepatitis C and studies for elucidation of the HCV infection mechanism.

EMBODIMENTS FOR CARRYING OUT THE INVENTION

Figure 1:
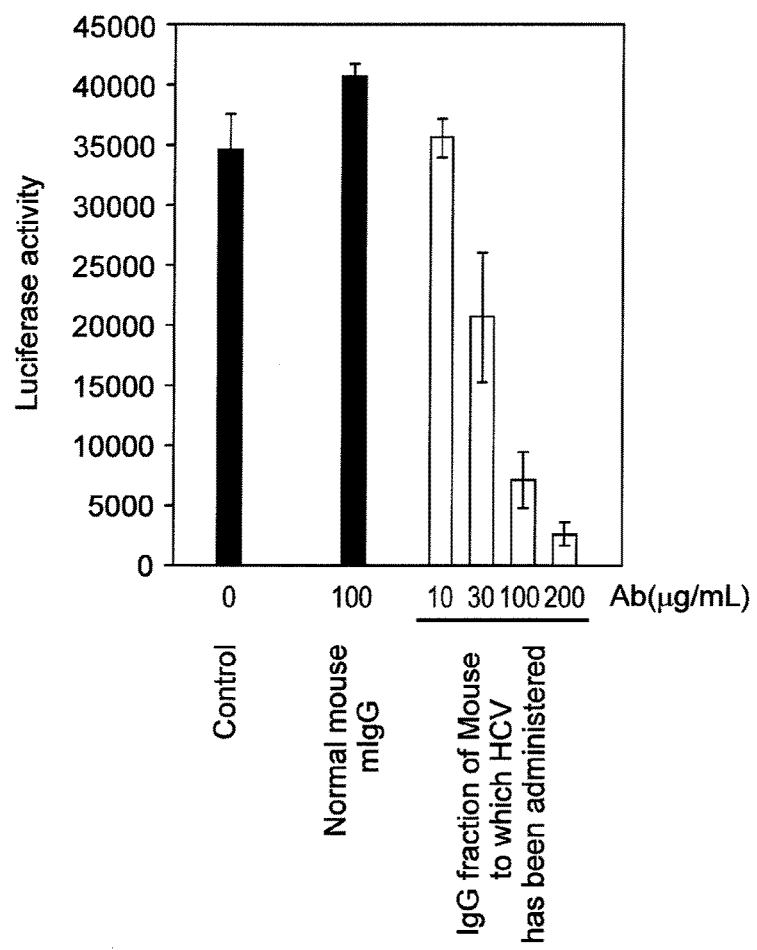
FIG. 1 shows the activity of inhibiting HCV infection of IgG fractions from the serum samples of mice to which J6/JFH-1-HCV particles were administered.

The embodiments of the present invention are as described in detail below. The present invention can be implemented via conventional molecular biological and immunological techniques within the technical scope in the art. Such techniques are thoroughly explained in, for example, Sambrook et al., Molecular Cloning: A Laboratory Manual, Cold Spring Harbor Laboratory (Third Edition, 2001) or Ed Harlow et al., Antibodies: A Laboratory Manual, Cold Spring Harbor Laboratory, 1988.

All publications, patents, and patent applications cited herein are incorporated herein by reference in their entirety.

1. Anti-HCV Antibody and Fragment Thereof

An embodiment of the present invention relates to an anti-HCV antibody or a fragment thereof, which reacts with an HCV particle as an antigen and has activity of inhibiting HCV infection.

1-1. Anti-HCV Antibody and Fragment Thereof

The term "anti-HCV antibody" in the present invention refers to an antibody that is induced using an HCV particle produced from a chimeric HCV genome (described later) as an antigen. Such an anti-HCV antibody is namely a neutralizing antibody that recognizes and binds to the conformation in HCV particles as an epitope, and has activity of inhibiting infection of host cells with HCV. Examples of the anti-HCV antibody of the present invention include polyclonal antibodies or monoclonal antibodies. The anti-HCV antibody is preferably a monoclonal antibody. The term "monoclonal antibody" as used herein refers to a polypeptide that contains a single immunoglobulin, or a framework region thereof (hereinafter, referred to as "FR"), and a complementarity determining region (hereinafter, referred to as "CDR"), and is capable of specifically binding to and recognizing an HCV particle as an antigen. Examples of the known antibody classes of the above immunoglobulin include IgG, IgM, IgA, IgE, and IgD. The antibody of the present invention may be of any class. An IgG antibody is preferable.

Specific examples of the anti-HCV antibody of the present invention include antibodies comprising CDRs that contain the amino acid sequences shown in SEQ ID NOs: 18, 20, and 22, or SEQ ID NOs: 32, 34, and 36 in a heavy chain variable region (H chain V region: hereinafter, referred to as "VH"). An example thereof is an antibody having VH that contains the amino acid sequence shown in SEQ ID NO: 13 or 15.

Also, specific examples of the anti-HCV antibody of the present invention include antibodies comprising CDRs that contain the amino acid sequences shown in SEQ ID NOs: 25, 27, and 29, or SEQ ID NO: 39, 41, and 43 in a light chain variable region (L chain V region: hereinafter, referred to as "VL"). An example thereof is an antibody having VL that contains the amino acid sequence shown in SEQ ID NO: 14 or 16.

The amino acid sequence of the antibody of the present invention, a variable region (hereinafter, referred to as "V region") of a fragment thereof (described later), or particularly FR contained in the region may contain a mutation as long as it can maintain the activity of specifically binding to HCV particles. Specifically, 1 to 5, preferably 1 to 4, more preferably 1 to 3, further preferably 1 or 2 amino acids in the amino acid sequence of FR may be deleted, substituted, inserted, or added. The reason for this is as follows. Since FR is the region composing the skeleton of a V region and thus is not directly involved in the antigen-binding specificity of the antibody, the activity of specifically binding to HCV particles is highly likely maintained even when the above mutation is introduced into the relevant region. On the other hand, introduction of a mutation into CDR highly likely causes a change in the antigen-specific binding activity, and thus is generally not preferable. However, there is a known example that introduction of a mutation into CDR may significantly enhance the binding activity of an antibody. Therefore, in the present invention, the above mutation may be within CDR. In this case, CDR may contain a deletion, a substitution, an insertion, or an addition of 1 to 3, and preferably 1 or 2 amino acids. For such introduction of a mutation, a phage vector described later can be used. A phage vector can be conveniently used for screening for an antibody containing a mutation that retains the activity of specifically binding to HCV particles or enhances such specific activity, since it enables rapid expression of an introduced antibody in a large amount, and is capable of expressing the antibody molecules in sufficient amounts on the host bacterial cell surfaces.

The term "a fragment thereof" in the present invention refers to a partial region of the above anti-HCV antibody that is a polypeptide chain having activity substantially equivalent to the antigen-specific binding activity of the relevant antibody or a complex thereof. An example thereof is an antibody portion containing at least one antigen binding site, that is, a polypeptide chain having at least one VL and at least one VH or a complex thereof. Specific examples thereof include many sufficiently characterized antibody fragments resulting from cleavage of immunoglobulin with various peptidases. More specific examples thereof include Fab, F(ab')$_2$, and Fab'. Fab is a fragment that is generated by cleaving an IgG molecule with papain at a position closer to the N-terminal side than the position of the disulfide bond in the hinge region, which is composed of a polypeptide consisting of VH and H chain C region (heavy chain constant region: hereinafter, referred to as "CH") 1 adjacent to VH among 3 domains (CH1, CH2, and CH3) composing CH and a light chain. F(ab')$_2$ is a Fab' dimer that is generated by cleaving an IgG molecule with pepsin at a position closer to the C-terminal side than the position of the disulfide bond in the hinge region. Fab' has the H chain that is slightly longer than that of Fab since it contains the hinge region, but has a structure substantially equivalent to that of Fab (see Fundamental Immunology, Paul ed., 3d ed. 1993). Fab' can be obtained by reduction of F(ab')$_2$ under mild conditions to cleave disulfide bond in the hinge region. These antibody fragments contain antigen binding sites, being capable of specifically binding to antigens (that is, HCV particles in the present invention).

The anti-HCV antibody or a fragment thereof of the present invention can be modified. Examples of modification mentioned herein include both functional modification required for the antibody or a fragment thereof of the present invention to have activity of specifically binding to HCV particles (e.g., glycosylation) and labeling required for detection of the antibody or a fragment thereof of the present invention. Examples of labeling of the above antibody include labeling with fluorescent dyes (FITC, rhodamine, Texas Red, Cy3, and Cy5), fluorescent proteins (e.g., PE, APC, and GFP), enzymes (e.g., horseradish peroxidase, alkaline phosphatase, and glucose oxidase), or biotin or (strepto) avidin. Also, glycosylation of the antibody of the present invention may be modified to adjust the affinity of the antibody for a target antigen. Such a modification may be achieved by, for example, changing one or more glycosylated sites within the sequence of an antibody. This is more specifically explained as follows. For example, one or more amino acid substitutions are introduced into an amino acid sequence composing one or more glycosylated sites within FR to remove the glycosylated sites, so that the sites can be deglycosylated. Such deglycosylation is effective for enhancing the affinity of an antibody for an antigen (U.S. Pat. Nos. 5,714, 350 and 6,350,861).

The anti-HCV antibody or a fragment thereof of the present invention preferably has high affinity, such that the dissociation constant between the antibody (or a fragment thereof) and HCV particles is $5.0\,e^{-9}$M or less, preferably $1.0\,e^{-9}$M or less, more preferably $5.0\,e^{-10}$M or less, $1.0\,e^{-10}$M or less, $5.0\,e^{-11}$M or less, $1.0\,e^{-11}$M or less, $5.0\,e^{-12}$M or less, or $1.0\,e^{-12}$M or less. The dissociation constant can be measured using techniques known in the art. For example, dissociation constant may also be measured using rate assessment kit software of a BIAcore system (GE Healthcare Bioscience). In addition, dissociation constant is preferably measured in the presence of 0.3M sodium chloride for precise measurement. Such conditions may be appropriately determined.

The anti-HCV antibody or a fragment thereof of the present invention is an antibody or a fragment thereof derived from an arbitrary organism, and preferably derived from a mammal or a fragment thereof. When the anti-HCV antibody or a fragment thereof of the present invention is administered to a human for the purpose of inhibiting HCV infection, it is desirably a human antibody, or a recombinant antibody synthesized chemically or by a recombination DNA method. This is because the constant region (hereinafter referred to as "C region") of an anti-HCV antibody derived from a non-human organism has immunogenicity in a human body, so that immune reaction is induced against the antibody, and thus the above purpose cannot be achieved.

The above "recombinant antibody" as used herein refers to a chimeric antibody, humanized antibody, or a synthetic antibody, for example.

The term "chimeric antibody" refers to an antibody resulting from substitution of the C region of an antibody with the C region of another antibody. An example thereof is an antibody resulting from substitution of the C region in a mouse monoclonal antibody (P18-9E or P19-7D) having activity of inhibiting HCV infection described later with the C region of a human antibody. This can alleviate immune reaction against the antibody within a human body. A more specific example of a chimeric antibody in the present invention is an antibody wherein VL contains the amino acid sequence shown in SEQ ID NO: 14 or 16 derived from an anti-HCV mouse monoclonal antibody and the L chain C region (light chain constant region: hereinafter, referred to as "CL") contains an amino acid sequence in CL of an arbitrary human antibody, and/or VH contains the amino acid sequence shown in SEQ ID NO: 13 or 15 derived from an anti-HCV mouse monoclonal antibody and CH contains an amino acid sequence in CH of an arbitrary human antibody.

The term "humanized antibody" is also referred to as a reshaped human antibody, such antibody is a mosaic antibody obtained by grafting CDR of an antibody of a non-human mammal (e.g., a mouse) into the CDR of a human antibody, for example. Mainly CDR groups in the V regions are responsible for the antigen-binding specificity of antibodies. Therefore, when a recombinant antibody having binding properties similar to those of a specific antibody is prepared, there is no need to obtain the full-length amino acid sequence of the antibody. Through the use of an existing recombination DNA technique, a mosaic antibody is prepared by substituting the DNA sequence encoding each CDR region derived from the antibody with a DNA sequence encoding a human antibody-derived CDR corresponding thereto, and then causing the expression of the resultants. Thus, a recombinant antibody with properties of such a specific antibody can be obtained through simulation thereof. A general gene recombination technique for preparation of a humanized antibody is also known (European Patent Application Publication No. EP 125023). An example thereof is a method that involves designing a DNA sequence to ligate CDR of a mouse antibody against FR of a human antibody and then synthesizing the DNA sequence by a PCR method using several oligonucleotides as primers so as to have overlap portions at terminal regions of both CDR and FR. In the present invention, CDRs of anti-HCV mouse monoclonal antibodies (P18-9E and P19-7D) were revealed. Hence, a humanized antibody can be prepared by the following method, for example.

The term "synthetic antibody" refers to an antibody or an antibody fragment synthesized chemically or via a recombination DNA method. Examples thereof include a monomeric polypeptide molecule prepared by artificially ligating one or more VLs and one or more VHs of a specific antibody via a linker peptide or the like having an appropriate length and sequence and a polymeric polypeptide thereof. Specific examples of such a polypeptide include single-stranded Fv (scFv: single chain Fragment of variable region) (see Pierce Catalog and Handbook, 1994-1995, Pierce Chemical Co., Rockford, Ill.), a diabody, a triabody, a tetrabody and the like. In an immunoglobulin molecule, VL and VH are generally located on different polypeptide chains (light chain and heavy chain). Single-stranded Fv is a synthetic antibody fragment having a structure in which these V regions existing on the two polypeptide chains are linked via a flexible linker with a sufficient length, and said two V regions are contained in a single polypeptide chain. Both V regions within the single-stranded Fv can form one functional antigen binding site through self assembly thereof. Single-stranded Fv can be obtained by incorporating recombinant DNA encoding the Fv into a phage genome with a known technique, followed by expression thereof. A diabody is a molecule having a structure based on the dimeric structure of single-stranded Fv (Holliger et al., 1993, Proc. Natl. Acad. Sci. U.S.A. 90: 6444-6448). For example, when the above linker has a length shorter than about 12 amino acid residues, two variable sites within single-stranded Fv cannot perform self assembly. However, through the formation of a diabody, specifically, through interaction between the two single-stranded Fvs, the assembly of the VL of one Fv chain with the VH of the other Fv chain becomes possible, so that two functional antigen binding sites can be formed (Marvin et al., 2005, Acta Pharmacol. Sin. 26:649-658). Moreover, through addition of cysteine residues to the C-termini of single-stranded Fvs, disulfide bond between the two Fv chains can be formed, so that a stable diabody can also be formed (Olafsen et al., 2004, Prot. Engr. Des. Sel. 17: 21-27). As described above, a diabody is a divalent antibody fragment. However, the antigen binding sites thereof are not required to bind to the same epitopes and may have bispecificity so that they recognize different epitopes for specific binding. For example, one of the antigen binding sites may be composed of VH that comprises CDRs containing the amino acid sequences shown in SEQ ID NOs: 18, 20, and 22 (corresponding to CDR1, CDR2, and CDR3, respectively, in VH of P18-9E) and VL that comprises CDRs containing the amino acid sequences shown in SEQ ID NOs: 25, 27, and 29 (corresponding to CDR1, CDR2, and CDR3, respectively, in VL of P18-9E), and the other antigen binding site may be composed of VH that comprises CDRs containing the amino acid sequences shown in SEQ ID NOs: 32, 34, and 36 (corresponding to CDR1, CDR2, and CDR3, respectively, in VH of P19-7D) and VL that comprises CDRs containing the amino acid sequences shown in SEQ ID NOs: 39, 41, and 43 (corresponding to CDR1, CDR2, and CDR3, respectively, in VH of P19-7D). A triabody and a tetrabody have a trimeric structure and a tetrameric structure, respectively, based on the single-stranded Fv structure, similarly to a diabody. A triabody and a tetrabody may be a trivalent antibody fragment and a tetravalent antibody fragment, respectively, and may also be multi-specific antibodies. Furthermore, the above term "a fragment thereof" refers to an antibody fragment identified using a phage display library (e.g., see McCafferty et al., 1990, Nature Vol. 348: 552-554) and having antigen binding capacity. In addition, for example, see Kuby, J., Immunology, $3^{rd}$ Ed., W.H. Freeman & Co., New York (1998).

The term "HCV infection" refers to a process during which HCV particles bind to the cell surfaces of host cells, are proliferated in the host cells, and then are released outside the cells. Therefore, the term "inhibiting (inhibition of) HCV infection" as used herein refers to inhibition or suppression of at least one of the above series of steps of HCV infection. Preferably, a pathway for HCV to bind to virus receptors on the surfaces of host cells and/or a pathway for an HCV genome to enter the host cells is inhibited.

1-2. HCV Particles as Antigens

The anti-HCV antibody in the present invention is characterized by reacting with an HCV particle produced from a chimeric HCV genome as an antigen.

The term "HCV particles" refers to HCVs comprising HCV envelope proteins and the HCV genome packaged therein.

The term "chimeric HCV genome" refers to an HCV genome derived from two or more different HCV genomes. For example, the HCV genome is generally composed of RNA consisting of, from the 5'side to the 3' side, the 5' untranslated region, the core protein-coding sequence (hereinafter, referred to as "core sequence"), the E1 protein-coding sequence (hereinafter, referred to as "E1 sequence"), the E2 protein-coding sequence (hereinafter, referred to as "E2 sequence"), the p7 protein-coding sequence (hereinafter, referred to as "p7 sequence"), the NS2 protein-coding sequence (hereinafter, referred to as "NS2 sequence"), the NS3 protein-coding sequence (hereinafter, referred to as "NS3 sequence"), the NS4A protein-coding sequence (hereinafter, referred to as "NS4A sequence"), the NS4B protein-coding sequence (hereinafter, referred to as "NS4B sequence"), the NS5A protein-coding sequence (hereinafter, referred to as "NS5A sequence"), the NS5B protein-coding sequence (hereinafter, referred to as "NS5B sequence"), and the 3' untranslated region. Therefore, the "chimeric HCV genome" is characterized in that each of the above regions composing the HCV genome is composed of regions derived from two or more different HCV strains.

Two or more different HCV strains composing each region in the above chimeric HCV genome are not particularly limited. Examples thereof include the JFH-1 strain (genotype 2a), the J6CF strain (genotype 2a), and the TH strain (genotype 1b). Also, original HCV strains from which regions constituting the chimeric genomes are derived and combinations thereof are not particularly limited. This is specifically explained below. Such a chimeric HCV genome comprises, for example, (i) the 5' untranslated region, the core sequence, the E1 sequence, the E2 sequence, the p7 sequence, and the NS2 sequence, which may be derived from strains other than the JFH-1 strain, and (ii) the NS3 sequence, the NS4A sequence, the NS4B sequence, the NS5A sequence, the NS5B sequence, and the 3'untranslated region, which may be derived from the JFH-1 strain. Alternatively, such a chimeric HCV genome comprises (i) the 5'untranslated region, the core sequence, the E1 sequence, the E2 sequence, and the p7 sequence, which may be derived from strains other than the JFH-1 strain, and (ii) the NS2 sequence, the NS3 sequence, the NS4A sequence, the NS4B sequence, the NS5A sequence, the NS5B sequence, and the 3' untranslated region, which may be derived from the JFH-1 strain.

In one embodiment, such a chimeric HCV genome comprises, from the 5' side to 3' side, (i) the 5' untranslated region, the core sequence, the E1 sequence, the E2 sequence, and the p7 sequence, which are derived from the J6CF strain, and (ii) the NS2 sequence, the NS3 sequence, the NS4A sequence, the NS4B sequence, the NS5A sequence, the NS5B sequence, and the 3' untranslated region, which are derived from the JFH-1 strain. Preferably, such a chimeric HCV genome comprises (i) the 5' untranslated region, the core region, the E1 region, the E2 region, the p7 region, and the sequence encoding 16 amino acid residues from the N-terminal side of the NS2 region, which are derived from the J6CF strain, and (ii) the sequence encoding $17^{th}$ amino acid residue from the N-terminal side and the following amino acid residues of the NS2 region, the NS3 region, the NS4A region, the NS4B region, the NS5A region, the NS5B region, and the 3'untranslated region, which are derived from the JFH-1 strain. Such a chimeric genome has been cloned into J6/JFH-1 consisting of the nucleotide sequence of SEQ ID NO: 2. Furthermore, such a chimeric genome may comprise the 5' untranslated region derived from the JFH-1 strain, the core sequence, the E1 sequence, the E2 sequence, and the p7 sequence, which are derived from the TH strain (Wakita, T. et al., J. Biol. Chem., 269, 14205-14210, 1994, JP Patent Publication (Kokai) No. 2004-179), and the NS2 sequence, the NS3 sequence, the NS4A sequence, the NS4B sequence, the NS5A sequence, the NS5B sequence, and the 3' untranslated region, which are derived from the JFH-1 strain. Preferably, such a chimeric genome may comprise preferably the 5' untranslated region derived from the JFH-1 strain, the core sequence, the E1 sequence, the E2 sequence, the p7 protein, and the sequence encoding 33 amino acid residues from the N-terminal side of the NS2 region, which are derived from the TH strain, the sequence encoding the $34^{th}$ amino acid residue from the N-terminal side and the following amino acid residues of the NS2 region, the NS3 sequence, the NS4A sequence, the NS4B sequence, the NS5A sequence, the NS5B sequence, and the 3' untranslated region, which are derived from the JFH-1 strain.

Also, in one embodiment, HCV particles produced from the chimeric HCV genome as described herein are inactivated by a method described later, so that the HCV particle can also be used as a vaccine. Inoculation of the vaccine to a human according to a method known in the art makes it possible to directly produce the anti-HCV antibody of the present invention in vivo in the inoculated subject.

1-3. Preparation of HCV Particles

Infectious HCV particles to be used as antigens in the present invention can be prepared with a cell culture system. Basic techniques for preparation of infectious HCV particles are described in WO04104198A1, WO06022422A1, WO06096459A2, Wakita, T. et al., Nat. Med. 11: 791-796, 2005, Lindenbach, B D. et al., Science 309: 623-626, 2005, and Pietschmann, T. et al., Proc. Natl. Acad. Sci. USA. 103: 7408-7413, 2006. Preparation of infectious HCV particles is specifically described below.

1-3-1. Chimeric HCV Genome

A chimeric HCV genome as described in the above section, "1-2. HCV particle as antigen," can be used for preparation of HCV particles. For example, a nucleic acid having the nucleotide sequence shown in SEQ ID NO: 2 can be used. Also, a chimeric HCV genome to be used herein may be either RNA or DNA. However, when a nucleic acid is RNA, "thymine (T)" in the above nucleotide sequence is read as "uracil (U)." In this description, the same applies to other nucleotide sequences.

1-3-2. Preparation of Chimeric HCV Genome RNA

HCV particles can be prepared by synthesizing chimeric HCV genome RNA from an expression vector constructed by ligating the cDNA of full-length chimeric HCV genome RNA downstream of a transcription promoter so as to enable expression (e.g., a vector resulting from insertion of a chimeric HCV genome under control of T7 promoter), and then introducing the genomic RNA into host cells. Techniques known in the art may be used for synthesizing such genomic RNA. For example, when the above expression vector is used, genomic RNA can be synthesized by an in vitro RNA synthesis method. Various kits for which such an in vitro RNA synthesis method is employed are commercialized by manufacturers relating to life science (e.g., MEGAscript T7 kit; Ambion). Genomic RNA may be synthesized using such a kit.

1-3-3. Host Cell

Examples of host cells, into which the thus synthesized chimeric HCV genome RNA is introduced, are not particularly limited, as long as these cells allow formation of HCV particles. Examples thereof include cultured cells such as Huh7, HepG2, IMY-N9, HeLa, HEK293, and the like more preferably liver-derived cultured cells such as Huh7, and further preferably derivative strains of Huh7, such as Huh7.5 and Huh7.5.1. The term "derivative strain" in the present invention refers to a cell line that is induced from a cultured cell and differs from its original strain. Also, in Huh7, HepG2, IMY-N9, HeLa, or HEK293 cells, in which the CD81 gene and/or the Claudin1 gene is expressed, can also be used.

1-3-4. Method for Introducing Chimeric HCV Genome RNA into Host Cell

As a method for introducing chimeric HCV genome RNA into the above host cells, any known method can be employed. Examples thereof include calcium phosphate coprecipitation, a DEAE dextran method, lipofection, microinjection, and electroporation. Preferable examples thereof include lipofection and electroporation and an even more preferable example thereof is electroporation.

The capacity of host cells, in which chimeric HCV genome RNA has been introduced, for viral particle production can be evaluated by a technique known in the art. For example, such capacity can be confirmed by ELISA (Enzyme-Linked Immuno Sorbent Assay) method, western blotting, or the like with the use of an antibody reacting with a protein that constitutes HCV particles, such as the core protein, the E1 protein, or the E2 protein released in the culture solution. Also, chimeric HCV genome RNA contained in the HCV particles in the culture solution may be amplified via RT-PCR using specific primers for detection to indirectly detect the presence of HCV particles.

1-3-5. Verification of Infectious Ability of HCV Particles

Whether or not the prepared HCV particles are infectious can be confirmed by a method for evaluation of viral infection, which is known in the art. For example, a supernatant obtained by culturing cells into which chimeric HCV genome RNA has been introduced is further added to new HCV permissive cells (e.g., Huh7 cells), and then culturing cells for appropriate time period (e.g., 48 hours). Subsequently, the cells are sufficiently washed, and then immunostained with an antibody that recognizes an HCV-specific protein such as anti-core antibody to count the number of infected cells. Alternatively, evaluation can be carried out by extracting a protein from the above cells, subjecting the extract to electrophoresis on SDS-polyacrylamide gel, and then detecting the HCV-specific protein via western blotting.

1-3-6. Purification of HCV Particles

The thus obtained HCV particles are preferably purified before use as antigens. HCV particles can be purified by removing cells and/or cell residues from a solution (virus solution) containing infectious HCV particles obtained by culturing the above cells into which the chimeric HCV genome RNA has been introduced, carrying out column chromatography or density-gradient centrifugation or a combination of the two in any order. Cells and residues thereof can be removed by centrifugation and/or filtration, for example. If necessary, a virus solution from which residues have been removed can be concentrated approximately 10- to 100-fold using an ultrafiltration membrane with a molecular weight cut off ranging from 100,000 to 500,000.

Examples of the above column chromatography include gel filtration chromatography, ion exchange chromatography, and affinity chromatography. A preferable example of gel filtration chromatography is chromatography using a cross-linked polymer of allyl dextran and N,N'-methylenebisacrylamide as the gel matrix. A more preferable example thereof is chromatography comprising Sephacryl (registered trademark) S-300, S-400, and S-500. An example of ion-exchange chromatography is a method using Q-Sepharose (registered trademark) as an anion exchange resin and SP Sepharose (registered trademark) as a cation exchange resin. For affinity chromatography, a resin binding heparin, sulfated cellulofine, lectin, and a substrate selected from various dyes bound thereto as a ligand can be used as a support. A preferable example thereof is affinity chromatography using HiTrap Heparin HP (registered trademark), HiTrap Blue HP (registered trademark), HiTrap Benzamidine FF (registered trademark), and sulfated Cellulofine, and a support to which LCA, ConA, RCA-120, and WGA have been bound. More preferably, HCV particles are purified by affinity chromatography using sulfated Cellulofine as a support. With the use of this method, HCV particles can be purified 30-fold or more in terms of the ratio of the HCV RNA copy number to the total protein amount in the solution.

As a solute for the formation of density gradient in density-gradient centrifugation, cesium chloride, sucrose, Nycodenz (registered trademark), and a sugar polymer such as Ficoll (registered trademark) and Percoll (registered trademark) can be used. Sucrose can be further preferably used. As a solvent, preferably, water or a buffer, such as phosphate, Tris, acetate, or glycine buffer, can be used to be used for density-gradient centrifugation. The centrifugal force that is employed upon purification via density-gradient centrifugation preferably ranges from $1\times10^4$ g to $1\times10^9$ g, more preferably ranges from $5\times10^4$ g to $1\times10^7$ g, and most preferably ranges from $5\times10^4$ g to $5\times10^5$ g.

The temperature for purification of the above HCV particles preferably ranges from 0° C. to 40° C., more preferably ranges from 0° C. to 25° C., and most preferably ranges from 0° C. to 10° C.

When purification is carried out via density-gradient centrifugation in combination with column chromatography, preferably, HCV particles are first purified through a plurality of chromatography columns followed by density-gradient centrifugation. More preferably, a fraction containing HCV particles obtained via anion exchange column chromatography followed by affinity chromatography is subjected to purification via density-gradient centrifugation. Most preferably, a fraction containing HCV particles obtained with the use of a Q-Sepharose (registered trademark) column is further purified with the use of a sulfated cellulofine-based column, and the resulting fraction containing HCV particles is then purified via density-gradient centrifugation. During or after the steps of column chromatography and density-gradient centrifugation, dialysis or ultrafiltration may be carried out to substitute a solute of a solution containing HCV particles and/or to concentrate HCV particles.

1-3-7. Inactivation of HCV Particles

Inactivation of HCV particles to be used as antigens is not essential for preparation of the anti-HCV antibody of the present invention, when HCV particles are administered to non-human animals. However, inactivation is preferably carried out in terms of prevention of infection of a surgeon. Also, when an HCV particle produced from the above chimeric HCV genome is administered as a vaccine to a human, inactivation is essential. HCV particles can be inactivated by adding an inactivator such as formalin, β-propiolactone, or glutardialdehyde to a virus solution containing infectious HCV particles, and then sufficiently mixing the resultant (Appaiahgari et al., Vaccine, 22: 3669-3675, 2004). Further, a virus solution containing infectious HCV particles can be irradiated with ultraviolet rays to rapidly eliminate infectivity of HCV. Irradiation with ultraviolet rays is preferred since it realizes virus inactivation with little influence on proteins or the like that constitute HCV. A source of ultraviolet rays used for inactivation can be a commercially available germicidal lamp. In particular, a 15w germicidal lamp can be used, although the source is not limited thereto. Preferably, infectious HCV particles can be inactivated by irradiating a solution containing infectious HCV particles with ultraviolet rays at 20 $mW/cm^2$ at room temperature for at least 5 minutes. Moreover, such an inactivation method is not limited by the purified or unpurified state.

1-4. Preparation of Anti-HCV Antibody 1-4-1. Immunization of Animal

The antibody of the present invention can be obtained by administering HCV particles to animals to induce the antibody via immune reaction. Examples of animals to be used for immunization are not particularly limited, as long as they are non-human animals capable of producing antibody-producing cells with which hybridomas can be prepared. For example, non-human mammals and more specifically mice, rats, hamsters, guinea pigs, rabbits, goats, donkeys, sheep, camels, and horses can be used. In the present invention, examples involving the use of mice are described below.

Four- to 10-week-old mice may be immunized with the HCV particle antigen (immunogen) obtained in the above method. According to circumstances, the step of purification of HCV particles may be altered or omitted, and HCV particle inactivation may be omitted.

An HCV particle as an immunogen is dissolved in a buffer, so as to prepare an immunogen solution. At this time, an adjuvant may be added if necessary for effective immunization. Examples of an adjuvant include Freund's complete adjuvant (hereinafter, referred to as "FCA"), Freund's incomplete adjuvant (hereinafter, referred to as "FIA"), aluminium hydroxide gel, *Hemophilus pertussis* vaccine, Titer Max Gold (Vaxel), GERBU adjuvant (GERBU Biotechnik), and MPL (Monophosphoryl Lipid A)+TDM (synthetic trehalose dicorynomycolate) (Sigma Adjuvant System; Sigma). These adjuvants may be used independently or mixed and then used.

Next, an immunogen solution prepared as described above is administered to a mouse (e.g., the inbred mouse strain Balb/c) for immunization. Examples of a method for administration of such an immunogen solution include, but are not limited to, subcutaneous injection of FIA or FCA, intraperitoneal injection using FIA, and intravenous injection of 0.15 mol/L sodium chloride. A single dose of the immunogen is arbitraraily determined depending on, for example, the type of an animal to be immunized or the route of administration, to be generally about 50 µg to 200 µg per animal. Also, the intervals of immunization are not particularly limited (e.g., intervals of several days to several weeks, and preferably intervals of 1 to 4 weeks). After the primary immunization, boost immunization is preferably carried out 2 to 6 times, and preferably 3 or 4 times. Blood is collected from the venous plexus of the ocular fundus or caudal vein of the immunized mouse after the initial immunization and the antibody titer in the serum is preferably measured by ELISA or the like. Also, the activity of inhibiting HCV infection can also be measured. When the antibody titer reaches a plateau, the immunogen solution is injected intravenously or intraperitoneally to complete the final immunization. Preferably, no adjuvant is used for the final immunization. On days 3 to 10 after the final immunization, preferably on day 4 after the final immunization, blood is collected from the immunized mouse, serum is treated according to a known method (Antibodies: A Laboratory Manual Cold Spring Harbor Laboratory, 1988), and thus a polyclonal antibody can be obtained. In addition, whether or not an immunized animal produces the anti-HCV antibody of the present invention capable of inhibiting HCV infection can be preferably confirmed in advance, specifically, before the final immunization, by the methods according to the above-mentioned "1-3-5. Verification of infectious ability of HCV"and "1-4-6. Selection of anti-HCV antibody (described later)."

1-4-2. Preparation of Hybridoma Cell Producing Anti-HCV Monoclonal Antibody

When an anti-HCV monoclonal antibody is prepared, a hybridoma producing the antibody can be prepared by a method described below, for example.

First, antibody-producing cells are collected from the above-immunized mouse. Examples of antibody-producing cells include spleen cells, lymph node cells, and peripheral blood cells. Spleen cells or local lymph node cells are preferable. Subsequently, cell fusion of antibody-producing cells with myeloma cells is performed, so that a hybridoma producing an anti-HCV monoclonal antibody can be prepared. Myeloma cells to be used for cell fusion are not particularly limited, as long as they are mouse-derived established cells and capable of growing in vitro. For convenient selection of a hybridoma in a step described later, preferable myeloma cells have drug selectivity, so that they cannot survive in an unfused state in selective medium (e.g., HAT medium; that is, Dulbecco's modified MEM (hereinafter, referred to as "DMEM") supplemented with $5 \times 10^{-5}$M 2-mercaptoethanol, 100 units/mL penicillin, 100 µg/mL streptomycin, and 10% fetal calf serum (hereinafter, referred to as "FCS"), $10^{-4}$ M hypoxanthine, $1.5 \times 10^{-5}$ M thymidine, and $4 \times 10^{-7}$ M aminopterin), but they can survive only in a state fused to antibody-producing cells. For example, 8-azaguanine-resistant mouse (BALB/c-derived) myeloma cell lines P3-X63Ag8-U1 (P3-U1), SP2/0-Ag14 (SP2/0), P3-X63-Ag8653 (653), P3-X63-Ag8 (X63), and P3/NS1/1-Ag4-1 (NS1) can be used. These cell lines are available from RIKEN BioResource Center, ATCC (American Type Culture Collection), or ECACC (European Collection of Cell Cultures). Culture and subculture are carried out in accordance with a conventional technique (e.g., Antibodies: A Laboratory Manual Cold Spring Harbor Laboratory, 1988, Selected Methods in Cellular Immunology W.H. Freeman and Company, 1980).

For the above cell fusion of antibody-producing cells and myeloma cells, spleen cells and myeloma cells obtained as described above are washed, antibody-producing cells and myeloma cells are mixed at a ratio ranging from about 1:1 to 20:1 in medium for culturing animal cells, such as serum-free DMEM or RPMI1640 medium, and then fusion reaction is conducted in the presence of a cell fusion accelerator. As a cell fusion accelerator, polyethylene glycol (hereinafter, referred to as "PEG") having an average molecular weight ranging from 1,500 to 4,000 Da can be used at a concentration ranging from about 10% to 80%, for example. In general, PEG with an average molecular weight of 1,500 Da is preferably used. An auxiliary agent such as dimethyl sulfoxide can be used in combination to enhance the fusion efficiency, if necessary. Furthermore, antibody-producing cells can be fused to myeloma cells using a commercially available cell fusion apparatus utilizing electric stimuli (e.g., electroporation) (Nature, 1977, Vol. 266, 550-552).

After cell fusion treatment, cells are washed with medium used for culturing myeloma cells (e.g., DMEM supplemented with $5 \times 10^{-5}$M 2-mercaptoethanol, 100 units/mL penicillin, 100 µg/mL streptomycin, and 10% FCS). A cell suspension is prepared, appropriately diluted with FCS-containing RPMI1640 medium or the like, for example, and then added onto a 96-well plate at about $2 \times 10^6$ cells/well. Selective medium is added to each well, and then cells are cultured continuously while appropriately exchanging selective media. The culture temperature ranges from 20° C. to 40° C. and is preferably about 37° C. When the myeloma cells are of an HGPRT-deficient cell line or thymidine kinase (TK)-deficient cell line, only the hybridomas of antibody-producing cells and myeloma cells can selectively be cultured and grown in the selective medium containing hypoxanthine, aminopterin, and thymidine (HAT medium). As a result, cells that start to grow on about day 10 after the initiation of culture in the selective medium can be selected as hybridoma cells.

1-4-3. Test for Activity of Inhibiting HCV Infection

The presence or the absence of the activity of inhibiting HCV infection of antibodies produced by the above hybridomas can be determined by methods illustrated below and methods using infectious HCV particles, which described later in Examples. For example, first, the above anti-HCV monoclonal antibody-producing hybridoma is cultured, and then a portion of the culture supernatant is collected as an antibody sample. The antibody sample is mixed with the above infectious HCV particles, and then the reaction is conducted at 37° C. for 1 hour (mixed sample). Next, 50 µL of the mixed sample is added to the Huh7 cells cultured on the previous day at 5×10³ cells/well on a 96-well plate, followed by 2.5 hours of culture at 37° C. After culture, the culture solution and the mixed sample are removed, cells are washed with PBS, a fresh medium is added again, and culture is continued. The culture supernatant is removed 48 hours later, cells are washed once with PBS, 100 μL of ISOGEN (Nippon Gene) is added to prepare RNA from the cells, RNA is quantified, and the amount of HCV genomic RNA is then measured. HCV RNA is detected via quantitative RT-PCR by detecting RNA in the 5' untranslated region of HCV RNA according to the method of Takeuchi et al. (Gastroenterology, 116: 636-642, 1999).

Alternatively, the activity of inhibiting HCV infection can be evaluated by the following method. First, the antibody sample is mixed with infectious HCV particles obtained from an anti-HCV monoclonal antibody-producing hybridoma cell line, and the mixture is subjected to a reaction at 37° C. for 1 hour (mixed sample). Subsequently, 50 μL of the mixed sample is added to the Huh7 cells cultured on the previous day at 1×10⁴ cells/well on a 96-well plate, and then cells are cultured at 37° C. for 2.5 hours. After culture, the culture solution and the mixed sample are removed, cells are washed with PBS, a fresh medium is added again, and culture is continued. The culture solution is removed 72 hours later, the plate is introduced into ice-cold methanol to fix cells. Thereafter, methanol is removed via air drying, and cells are permeabilized with the use of Block Ace (registered trademark) (Dainippon Pharmaceutical Co., Ltd.) containing 0.3% Triton (registered trademark)-X 100 (GE Healthcare). The number of HCV-infected cells is counted under a fluorescent microscope using a clone 2H9 anti-HCV-core antibody (see Nat. Med., 2005, 11: pp. 791-6) and goat anti-mouse IgG-Alexa488 (Molecular Probes), and the antibody samples in the wells in which HCV infection is inhibited can be selected as an anti-HCV monoclonal antibody having activity of inhibiting HCV infection.

Alternatively, a test can be conducted for the activity of inhibiting HCV infection with the use of infectious HCV-like particles (hereinafter, referred to as "HCVpp") that are prepared by causing the display of functional HCV envelope proteins on retrovirus particles instead of infectious HCV particles. A green fluorescent protein (GFP) marker gene or a luciferase gene is packaged within HCVpp, making it possible to rapidly measure with high reliability infection mediated by HCV envelope proteins (Bartosch, B. et al. J. Exp. Med. 197: 633-642, 2003). Specifically, HCVpp having envelope proteins of genotype 2a can be obtained as follows, for example. A pcDNA J6dC-E2 vector is constructed by cloning a nucleic acid that encodes the $132^{nd}$ to the $750^{th}$ amino acid residues (corresponding to a part of the core protein, the E1 protein, and the E2 protein) of the protein (NCBI Protein Accession No. AAF01178.1) of the J6CF strain (an HCV strain of genotype 2a) into pcDNA3.1. A Gag-Pol 5349 expression vector is constructed by cloning genes encoding gag and pol of a mouse leukemia virus into the vector. A Luc126 retrovirus vector is constructed by cloning a luciferase gene into the vector. The vectors are transfected into HEK293T cells (ATCC CRL-1573) using FuGENE6 (Roche: catalog No. 11814443001). After transfection, a culture solution containing HCVpp is collected and then filtered with a 0.45-μm membrane filter, so that HCVpp having envelope proteins of genotype 2a can be obtained.

For preparation of HCVpp having envelope proteins of genotype 1a, a pcDNA H77dC-E2 vector can be used instead of the above pcDNA J6dC-E. The pcDNA H77dC-E2 vector is constructed by cloning a nucleic acid that encodes the $132^{nd}$ to the $746^{th}$ amino acid residues (corresponding to a part of the core protein, the E1 protein, and the E2 protein) of a protein (NCBI Protein accession No. AAB67036.1) of the H77 strain, which is an HCV strain of genotype 1a, into pcDNA3.1.

For preparation of HCVpp having envelope proteins of genotype 1b, a pcDNA THdC-E2 vector can be used instead of the above pcDNA J6dC-E. The pcDNA THdC-E2 vector is constructed by cloning a nucleic acid that encodes the $132^{nd}$ to the $747^{th}$ amino acid residues (corresponding to a part of the core protein, the E1 protein, and the E2 protein) of a protein of the TH strain, which is an HCV strain of genotype 1b, (Wakita, T. et al., J. Biol. Chem., 269, 14205-14210, 1994) into pcDNA3.1.

For example, HCVpp is mixed with the antibody sample obtained from an anti-HCV monoclonal antibody-producing hybridoma cell line, and then the mixture is allowed to react at 37° C. for about 30 minutes. The antibody sample is diluted with DMEM (DMEM containing 10% FCS, 1% MEM non-essential amino acid solution, 10 mM HEPES-Tris (pH 7.3), and 1 mM sodium pyruvate). The above mixture of HCVpp and the antibody sample is added to Huh7.5.1 cells cultured for 1 day on a 96-well plate at 1×10⁴ cells/well, followed by about 3 hours of culture at 37° C. After culture, the sample is removed, cells are washed once with PBS, fresh medium is added, and then culture is continued. After about 72 hours, the culture solution is removed. Cells are washed about 4 times with PBS, 25 μL/well serum-free DMEM and 25 μL/well lysis buffer (e.g., Steady-Glo (Promega: catalog No. E2520) can be used) are added, and then cells are lysed. (When a kit is used, cell lysis is basically performed according to instructions included therewith.) The cell lysis solution (40 μl/well) is transferred to a white 96-well plate (e.g., Sumitomo Bakelite Co., Ltd.: catalog No. MS-8496W), and then luminescence intensity is measured using an apparatus with which fluorescence can be measured (e.g., ARVO X4 (PerkinElmer)). Luminescence intensity (%) obtained after mixing with DMEM is regarded as representing 100% infection. Thus infection (%) after mixing with an antibody sample can be found. Therefore, an antibody sample that results in a decrease in infection (%) (that is, when the addition thereof results in low luminescence intensity) can be determined to be an anti-HCV monoclonal antibody having activity of inhibiting HCV infection.

In addition, the antibody-producing hybridoma of the present invention is not particularly limited, as long as it is a hybridoma that is selected by the above method. A specific example of such a hybridoma is a hybridoma cell line producing "P18-9E" or "P19-7D" monoclonal antibody having activity of inhibiting HCV infection of the present invention (described later).

1-4-4. Preparation of Anti-HCV Antibody

The hybridomas selected above are conditioned to serum-free medium, such as Hybridoma-SFM (Invitrogen), and the cultured supernatant can be designated as an anti-HCV antibody sample (anti-HCV monoclonal antibody sample). Culture can be conducted with the use of a flask, petri dish, spinner culture bottle, roller bottle, or high-density culture flask (CELLine, Becton, Dickinson and Company).

When monoclonal antibodies are prepared from animals, the anti-HCV monoclonal antibody-producing hybridoma cells selected above are intraperitoneally injected into pristane-treated 8- to 10-week-old mice, nude mice, or SCID mice (0.5 mL of 2,6,10,14-tetramethylpentadecane (pristane) is administered intraperitoneally and mice are grown for 2 weeks) at 2×10⁷ to 5×10⁶ cells/mouse. Hybridomas experience ascites tumor formation within 10 to 21 days. Ascites fluid is sampled from the mice or the like to prepare anti-HCV monoclonal antibody samples. The obtained antibody samples are centrifuged to remove cells or disrupted cells, the samples are subjected to salting-out with 40% to 50% saturated ammonium sulfate, caprylic acid precipitation, DEAE-Sepharose column, Protein-A column, Protein-G column, HiTrap IgM Purification HP-column (GE Healthcare), mannan binding protein-column (Pierce), or gel filtration column, and such techniques are carried out alone or in adequate combination to recover IgG or IgM fractions. Thus, purified anti-HCV monoclonal antibodies can be obtained. The purified monoclonal antibody subclasses are determined with the use of, for example a mouse monoclonal antibody typing kit (Pierce). The classes of the antibodies having activity of inhibiting HCV infection of the present invention are not particularly limited. Such an antibody class is preferably IgG or IgM and IgM antibodies are more preferable.

1-4-5. Preparation of Anti-HCV Humanized Antibody

For anti-HCV humanized antibodies, FRs of human antibodies with which CDRs can form good antigen-binding sites are selected. According to need, amino acids in FRs in the antibody V regions may be substituted, so that the complementarity determining regions (CDRs) of the reshaped human antibodies form adequate antigen-binding sites (Sato, K., et al., Cancer Res. 53: 851-856, 1993).

When humanized anti-HCV antibodies of the present invention are prepared, for example, mRNA is extracted from anti-HCV monoclonal antibody-producing hybridomas, so as to synthesize cDNA encoding VH and VL. The thus synthesized cDNA is inserted into a phage or plasmid vector to construct a cDNA library. Recombinant phages or plasmids having cDNA encoding VH and recombinant phages or plasmids having cDNA encoding VL are separately isolated from the resulting library with the use of the C or V region of the mouse antibody as a probe. The whole nucleotide sequences of VH and VL of the target antibody on the recombinant phage or plasmid are determined, and the whole amino acid sequences of VH and VL are deduced based on the nucleotide sequences.

Alternatively, cDNA encoding VH and VL can be cloned via PCR. cDNAs of hybridomas prepared in the above-described manner are used as templates, the templates are amplified using a plurality of primers designed based on the amino acid sequences conserved in the relevant genes, and the cDNA fragments are cloned into cloning vectors. Thus, cDNA encoding VH and VL can be obtained.

cDNA encoding VH and VL of the anti-HCV antibody may be inserted into a region upstream of the gene encoding CH and CL of the human antibody to construct cDNA encoding a human anti-HCV monoclonal antibody. In CH, Cγ1, Cγ2, Cγ3, and Cγ4 can be used, and in CL, Cκ and Cλ can be used. In order to improve stability of the antibody or production thereof, the C region may be modified.

When mammalian cells are used as host cells, the gene of interest can be expressed using an expression vector containing a promoter that can express the gene of interest in mammalian cells, the antibody gene to be expressed, and poly A signal operably linked to a site downstream of the 3' end. Examples of promoters that can be used herein include virus promoters/enhancers, such as human cytomegalovirus, retrovirus, polyoma virus, adenovirus, and simian virus 40 (SV40) and promoters/enhancers derived from mammalian cells, such as the elongation factor 1α (EF1α).

When *E. coli* is used as a host, the gene of interest can be expressed with the use of an expression vector in which a promoter that can express the gene of interest in *E. coli* cells, a signal sequence for antibody secretion, and the antibody gene to be expressed are operably linked. Examples of promoters include lacZ promoter, araB promoter, Trp promoter, and T7 promoter.

When insect cells are used as host cells, the gene of interest can be expressed with the use of an expression vector containing a promoter that can express the gene of interest in insect cells, the antibody gene to be expressed, and poly A signal operably linked to a site downstream of the 3' end. Examples of promoters that can be used herein include polyhedrin promoter and baculovirus OpNMPV-derived immediate-early OpIE2 promoter.

Host cells containing the above expression vector for expression of an anti-HCV humanized antibody of the present invention are cultured under appropriate conditions according to a conventional technique, so that the antibody is produced in the culture solution supernatant or within the host cells. Specifically, for example, when cultured cells of a mammal are used as host cells, the host cells are seeded in DMEM at $1\times10^5$ cells/mL, and then cultured with a 5% $CO_2$ incubator at 37° C., so that a culture solution supernatant containing the antibody can be obtained. Also, for example, when *Escherichia coli* is used as a host cell, the host cells are seeded and cultured in medium such as LB medium, which is generally used for culturing *Escherichia coli*, so as to induce protein expression. Thus, the antibody of interest can be produced in the culture solution supernatant or within the host cells.

In addition, an anti-HCV humanized antibody of interest can be purified and recovered from a culture solution supernatant or a disrupted cell solution through selection for the C region using a protein A column, a protein G column, an anti-immunoglobulin antibody affinity column, or the like.

1-4-6. Selection of Anti-HCV Antibody

For selection of the anti-HCV antibody of the present invention, HCV proteins are immobilized (i.e., solid-phased) on a support, the antibody sample is added, and then reaction is allowed to proceed for a period of time under conditions sufficient for the formation of an antibody/antigen complex. Next, for detection of the thus formed complex, a secondary antibody; that is, an antibody that has an enzyme, dye, or radioisotope as a signal and that recognizes the antibody sample is brought into contact with the resultant, so as to form a second mixture. The second mixture is allowed to react for a period of time under conditions sufficient for the formation of the antibody/antigen complex. Thus, the presence of the antibody that recognizes the HCV protein is detected with the aid of the signal of the enzyme, dye, or radioisotope.

As HCV proteins to be immobilized on a support, HCV particles may be used. Alternatively, proteins expressed in *E. coli*, yeast, mammalian cells, insect cells, or the like with the use of cDNA consisting of the core sequence, the E1 sequence, the E2 sequence, the p7 sequence, the NS2 sequence, the NS3 sequence, the NS4A sequence, the NS4B sequence, the NS5A sequence, or the NS5B sequence of the HCV genome may be used. Further, such proteins may be chemically synthesized and used. The length of the amino acid residues composing a protein to be used for immobilization is not limited, and such length is 3 or more amino acid residues and more preferably 8 or more amino acid residues.

Expression of the E1 protein and the E2 protein that are envelope proteins of the JFH-1 strain or the J6CF strain in mammalian cells is as described below, for example. The E1 protein of the JFH-1 strain or the J6CF strain (JFH1 strain: NCBI Protein Accession No. BAB32872, J6CF strain: NCBI Protein Accession No. AAF01178.1) starts from the $192^{nd}$ amino acid residue and ends at the $383^{rd}$ amino acid residue, when the initiator methionine of the full-length amino acid sequence of the protein of the JFH-1 strain is regarded as the $1^{st}$ amino acid residue. The portion ranging from the $353^{rd}$ to the $383^{rd}$ amino acid residues of the E1 protein is considered to be a transmembrane domain (also referred to as "C-terminal hydrophobic domain") (Cocquerel, L. et al., J. Virol. 74: 3623-3633, 2000).

The E2 protein of the JFH-1 strain or the J6CF strain starts from the $384^{th}$ amino acid residue and ends at the $750^{th}$ amino acid residue of the above amino acid sequence. The portion ranging from the $722^{nd}$ to the $750^{th}$ amino acid residues of the E2 protein is considered to be a transmembrane domain (Cocquerel, L. et al., J. Virol. 74: 3623-3633, 2000).

When proteins are secreted after the expression in the culture supernatant of mammalian cells, it is necessary for such proteins to have signal peptides, but it is not necessary for them to have transmembrane domains.

Accordingly, the E1 or E2 protein containing no transmembrane domain comprises the above $192^{nd}$ to the $352^{nd}$ amino acid residues and the above $384^{th}$ to the $721^{st}$ amino acid residues, respectively. Shift of an amino acid location is not problematic, provided that the amino acids are qualitatively equivalent to each other. A sequence ranging from the $192^{nd}$ to the $352^{nd}$ amino acid residues of the E1 protein of the JFH-1 strain, and a sequence ranging from the $384^{th}$ to the $720^{th}$ amino acid residues (and preferably the sequence ranging from the $384^{th}$ to the $714^{th}$ amino acid residues) of the E2 protein of the JFH-1 strain can be used as proteins that do not contain any transmembrane domain. Also, a sequence ranging from the $192^{nd}$ to the $352^{nd}$ amino acid residues of the E1 protein of the J6CF strain, and a sequence ranging from the $384^{th}$ to the $720^{th}$ amino acid residues of the E2 protein of the J6CF strain can be used as proteins that do not comprise a transmembrane domain. When such amino acid residue numbers are applied to amino acid sequences of other HCV strains, sequences may be designated with the amino acid residue numbers corresponding in alignment with the amino acid sequence of the relevant full-length JFH-1 protein.

A nucleic acid that encodes a protein not containing any transmembrane domain of the E1 or E2 protein can be synthesized via PCR using cDNA of the JFH-1 strain as a template based on the nucleic acid sequence (NCBI Nucleotide Accession No. AB047639) of the JFH-1 strain given in GenBank, or such nucleic acid can be fully synthesized.

The corresponding E1 and E2 protein regions of an HCV strain other than the JFH-1 strain can be easily determined by aligning the sequences, so that the lengths of matched portions (of the sequences) become the longest when compared with the sequence of the JFH-1 strain, while taking substitution or deletion of the sequence of the HCV strain into consideration. Such analysis can be carried out using genetic information processing software (e.g., GENETYX, Software Development Co., Ltd.).

When the E1 or E2 protein containing no transmembrane domain is secreted after expression in a mammalian cell, a nucleic acid encoding the protein is ligated to a site downstream of a nucleic acid that encodes a signal peptide in such a manner that reading frames of codons are correctly aligned (i.e., in-frame), a stop codon is added to the 3' end, and the resultant is then inserted into an expression vector. A signal peptide is mainly composed of hydrophobic amino acids comprising 15 to 30 amino acid residues located at the N terminus of the secretory protein and is involved in the mechanisms of protein transport through the cell membrane.

A signal peptide that can be used for protein secretion after expression in a mammalian cell may be a signal peptide of a secretory protein. Examples of vectors having signal peptides include a vector having a signal peptide sequence of mouse GM-CSF (JP Patent Publication (kokai) No. 63-276490 A (1988)), a pSecTag/FRT/V5-His vector (Invitrogen) having a signal peptide sequence of the IgG κ strand, a p3×FLAG-CMV13 vector (Sigma) having a signal peptide sequence of preprotrypsin, a pFUSE-Fc2 vector (InvivoGen) having a signal peptide sequence of IL-2, and a pTriEx-7 vector (Novagen) having a signal peptide sequence of IgM.

When a protein is expressed, such a protein is expressed as a fusion protein of a target protein and a label protein, and the fusion protein can be detected or purified with the use of an antibody reacting with the label protein or a molecule that specifically binds thereto. Such label proteins are also referred to as "tags." Label proteins are not limited, and examples thereof include FLAG peptide (also referred to as flag peptide or Flag peptide), 3×FLAG peptide (also referred to as 3×FLAG peptide, 3× Flag peptide, or 3× flag peptide), HA peptide, 3×HA peptide, myc peptide, 6×His peptide, GST polypeptide, MBP polypeptide, PDZ domain polypeptide, alkaline phosphatase, immunoglobulin, and avidin. Such peptides or polypeptides are generally fused to the N- or C-terminus of the target proteins, but such peptides or polypeptides can be inserted into the target proteins according to need. A vector having a fusion polypeptide of preprotrypsin signal peptide and 3×FLAG peptide is available as the p3×FLAG-CMV-9 vector from Sigma.

1-4-7. Analysis of Antibody Epitope

A preferred example of the antibody having activity of inhibiting HCV infection according to the present invention can recognize as an epitope the conformation of the complex of the E1 protein and the E2 protein of HCV, and of preferably the J6CF strain. Specifically, a preferred example of the antibody according to the present invention can recognize as an epitope the whole or a portion of the tertiary structure of the complex of the E1 protein and the E2 protein. The E1 protein and the E2 protein are envelope proteins involved in binding with receptors (HCV receptors) on the surfaces of host cells. HCV infects host cells via the HCV receptors. CD81 is identified as one of the HCV receptors, which has been reported to be one of essential factors for HCV infection (Akazawa et al., J. Virol. 81: 5036-5045, 2007). Therefore, HCV maintaining its ability to infect cells is thought to retain the conformation of the complex (of the E1 protein and the E2 protein) capable of binding to CD81.

The anti-HCV antibody of the present invention recognizes as an epitope the whole or a portion of the conformation of the complex of the E1 protein and the E2 protein in HCV, and binds thereto. Binding of the anti-HCV antibody of the present invention to the complex of the E1 protein and the E2 protein inhibits the binding of the E1 protein and the E2 protein of infectious HCV to CD81 on host cells. As a result, HCV is thought to lose its infectious ability. Therefore, the anti-HCV antibody of the present invention is capable of binding to various infectious HCVs and thus is capable of inhibiting HCV infection.

HCV is known to tend to undergo mutation. A diversity-carrying HCV aggregate that proliferates while undergoing mutation is referred to as "quasispecies." A hypervariable region (hereinafter, referred to as "HVR") that frequently undergo amino acid mutation is located at the N-terminus of the E2 protein of HCV. It has been demonstrated that known antibodies having activity of inhibiting HCV infection recognize a peptide of such a region that often undergoes mutation as an epitope (Farci et al., Proc. Natl. Acad. Sci. USA. 93: 15394-15399, 1996; Shimizu et al., J. Virol. 68: 1494-1500, 1994; Zhang et al., Proc. Natl. Acad. Sci. USA. 104: 8449-8454, 2007). However, it has been reported that an antibody that recognizes HVR as an epitope loses the effects due to HCV mutation (Farci et al., Proc. Natl. Acad. Sci. USA. 91: 7792-7796, 1994; Weiner et al., Proc. Natl. Acad. Sci. USA. 89: 3468-3472, 1992; Kato et al., J. Virol. 67: 3923-3930, 1993). Therefore, an epitope for the anti-HCV antibody is preferably an epitope other than HVR.

The anti-HCV antibody of the present invention recognizes as an epitope the conformation of the complex of the E1 protein and the E2 protein. Since the anti-HCV antibody of the present invention differs from a conventional anti-HCV antibody having activity of inhibiting HCV infection, which recognizes only HVR as an epitope, the anti-HCV antibody of the present invention can be expected to keep its effects of inhibiting infection due to quasispecies of HCV.

For analysis of an epitope of the antibody of the present invention produced by a hybridoma cell line selected by the above method, enzyme immunoassay (EIA), western blotting, dot blotting, or the like using HCV proteins can be employed. Through analysis of such an epitope as primary screening for an anti-HCV monoclonal antibody, an anti-HCV monoclonal antibody targeting a specific HCV protein can be efficiently screened for.

2. Inhibitory Agent for HCV Infection

Another embodiment of the present invention is an inhibitory agent for HCV infection.

The term "inhibitory agent for HCV infection" in the present invention refers to a substance comprising the above anti-HCV antibody of the present invention as an active ingredient and being capable of inhibiting at least one function required for the process of HCV to infect host cells. The inhibitory agent for HCV infection of the present invention can be used independently as a medicament or an active ingredient of a pharmaceutical composition, or preferably used as a medicament for treating or preventing hepatitis C. Furthermore, the inhibitory agent can also be used as a research tool for elucidation of the HCV infection mechanism.

2-1. Pharmaceutical Composition

The inhibitory agent for HCV infection of the present invention can be used for a pharmaceutical composition. The pharmaceutical composition of the present invention can comprise pharmaceutically acceptable carriers in addition to the anti-HCV antibody of the present invention as a medicament.

The term "pharmaceutically acceptable carriers" refers to a solvent and/or an additive that can be generally used in the technical field of formulation.

Examples of such pharmaceutically acceptable solvents include water and pharmaceutically acceptable organic solvents (e.g., ethanol, propylene glycol, ethoxy-isostearyl alcohol, polyoxy-isostearyl alcohol, and polyoxyethylene sorbitan fatty acid esters). These solvents are desirably sterilized and preferably adjusted to be isotonic to blood as necessary.

Also, examples of pharmaceutically acceptable additives include collagen, polyvinyl alcohol, polyvinyl pyrrolidone, carboxyvinyl polymer, carboxymethylcellulose sodium, sodium polyacrylate, sodium alginate, water-soluble dextran, carboxymethyl starch sodium, pectin, methylcellulose, ethylcellulose, xanthan gum, gum Arabic, casein, agar, polyethylene glycol, diglycerine, glycerine, propylene glycol, vaseline, paraffin, stearyl alcohol, stearic acid, human serum albumin (HSA), mannitol, sorbitol, lactose, and a surfactant, which is acceptable as a pharmaceutical additive.

The pharmaceutical composition of the present invention can further contain, an excipient, a binder, a disintegrator, a filler, an emulsifier, a fluid agent for addition and regulation, a lubricant, a taste and flavor corrigent, a solubilizing agent (solubilizer), a suspension, a diluent, a surfactant, a stabilizer, an absorption promotor, an extending agent, a wetting agent, a moisturizing agent (e.g., glycerin and starch), an adsorbent, a disintegration-suppressing agent, a coating agent, a colorant, a preservative, an antioxidant, aroma chemicals, a flavor agent, a sweetening agent, and a buffering agent, as necessary.

The above solvents and/or additives can be used independently or in appropriate combinations according to the dosage form of the pharmaceutical composition of the present invention to be used herein. For example, when the pharmaceutical composition of the present invention is used as a preparation for injection, a purified anti-HCV antibody is dissolved in a solvent (e.g., saline, buffer, and dextrose solution), an adsorption-preventing agent (e.g., Tween80, Tween20, gelatin, and human serum albumin) is added to the solution, and thus the resultant can be used. Alternatively, the pharmaceutical composition of the present invention may be freeze-dried so as to realize a dosage form such that the pharmaceutical composition is dissolved and reshaped before use. For example, an excipient (e.g., sugar alcohol or saccharides, such as mannitol and dextrose) can be used for freeze drying.

The pharmaceutical composition of the present invention can be formulated according to a conventional technique. Regarding formulation, see Remington's Pharmaceutical Science, latest edition, Mark Publishing Company, Easton, U.S.A., for example.

The pharmaceutical composition of the present invention can also be used in combination with an existing antiviral agent, such as interferon and ribavirin.

2-2. Method for Administering Pharmaceutical Composition

The pharmaceutical composition containing the inhibitory agent for HCV infection of the present invention is preferably administered in a unit dosage form. The pharmaceutical composition can be administered via peroral administration, interstitial administration (e.g., subcutaneous administration, intramuscular administration, and intravenous administration), local administration (e.g., transdermal administration), or transrectal administration. Therefore, dosage forms of the inhibitory agent for HCV infection are preferably appropriate for the routes of administration. For example, in the case of interstitial administration, injection that is performed via bloodstream is preferred, and thus the dosage form in such a case is liquid.

In the case of injection, injection sites are not particularly limited. Examples of injection include intravenous, intraarterial, intrahepatic, intramuscular, intra-articular, intramedullary, intraspinal, intraventricular, transdermal, subcutaneous, intradermal, intraperitoneal, intranasal, intraintestinal, and sublingual injections. A preferable example thereof is intravascular injection such as intravenous injection or intraarterial injection. This is because the pharmaceutical composition of the present invention can be immediately spread throughout the body via bloodstream and intravascular injection has relatively low invasiveness, causing little burden on subjects. Alternatively, intrahepatic or hepatoportal injection may be performed. This is because the inhibitory agent for HCV infection can be caused to act directly on sites where HCV is localized.

When the above inhibitory agent for HCV infection is administered, a single dosage unit thereof preferably contains effective dose by which the activity of inhibiting HCV infection can be exhibited. The term "effective dose" as used herein refers to an amount required for the active ingredient to exhibit its functions; that is, in the present invention, an amount of the inhibitory agent, which is required for the agent to inhibit HCV infection, but causes almost no or never causes harmful adverse reaction on a subject to which the inhibitory agent is administered. The effective dose can be varied depending on various conditions such as the information of a subject, formulation, and the route of administration. Examples of the "information of a subject" include the progression degree or the severity of the disease, general health, age, body weight, gender, dietary life, drug sensitivity, the presence or the absence of a medicament to be used in combination, and tolerance to treatment. The final dosage and effective dose of the above inhibitory agent for HCV infection are determined by doctors according to the information and the like of individual subjects. When administration of a large dose of the above inhibitory agent for HCV infection is required in order to obtain the effects of inhibiting HCV infection, the agent may be administered in divided doses so as to alleviate the burden on a subject.

A specific example of the dosage is as follows. When the inhibitory agent is administered to a human adult male (body weight: 60 kg) who is at the early phase of the onset of hepatitis C and does not need a combined use of another medicament, the effective dose per day of the inhibitory agent for HCV infection generally ranges from 1 mg to 2000 mg, preferably ranges from 1 mg to 1000 mg, and more preferably ranges from 1 mg to 500 mg. The dose less than or higher than the above ranges may also be administered depending on the state of a subject, the route of administration, or the like.

When the inhibitory agent for HCV infection of the present invention is administered to a subject, the effective dosage of the antibody of the present invention, which is the active ingredient, per administration is selected from within the range of 0.001 mg to 1000 mg per kg body weight. Alternatively, the effective dosage can be selected from within the range of 0.01 mg to 100000 mg per body of subject, but is not limited thereto. Also, the inhibitory agent may be administered either before or after the patient develops clinical symptoms of the disease.

The antibody having activity of inhibiting HCV infection of the present invention can be effective agasint any hepatitis C. For example, the antibody is effective against chronic hepatitis or fulminant hepatitis, and particularly effective against hepatitis C caused by HCV of genotype 2a or 1b.

3. Method for Detecting HCV

Further embodiments of the present invention are a method for detecting HCV and a reagent for detecting HCV, which is used for the method. According to the present invention, HCV particles in a sample can be detected by an immunological detection method using the anti-HCV antibody of the present invention.

The term "sample" as used herein refers to various samples that can comprise HCV particles or the envelope proteins thereof. Examples thereof include cultured cells, cultured cell-disrupted solutions, culture solution supernatants, and human samples. Examples of a human sample include: tissue collected from a human (e.g., postoperative tissue); and various human-derived biological samples such as body fluids (e.g., blood, serum, blood plasma, urine, spinal fluid, saliva, lymph fluid, and seminal fluid). Preferable examples thereof include blood, serum, blood plasma, and urine. Also samples in the present invention may be not only liquid samples, but also solid samples. For example, donor organs resulting from organ transplantation, tissue section samples, or the like can be used.

"Immunological detection method" of the present invention can be performed by a known immunological detection method using a labeled antibody, such as ELISA, EIA, fluorescence immunoassay, radioimmunoassay, or luminescence immunoassay, or, a surface plasmon resonance method (SPR method) or Quarts Crystal Microbalance measurement (QCM). Such an immunological detection method using a labeled antibody is preferably applied.

ELISA is also referred to as enzyme-linked immunosorbent assay, which involves detecting an antigen-antibody reaction with the use of an enzyme-labeled antibody or antigen and the action of the enzyme based on the color optical density or fluorescence intensity, so as to quantitatively determine a target antigen contained in a trace amount in a sample. Specifically, the method involves immobilizing the anti-HCV antibody or the HCV particles of the present invention onto a solid-phase support, and then enzymatically detecting an immunological reaction between the antibody or the like and HCV. Regarding ELISA, see known methods (Ed., Japanese Society of Laboratory Medicine, "Clinical Pathology, Extra Edition, Feature, No. 53, Immunoassay for Clinical Examination—Techniques and Applications-," The Clinical Pathology Press, 1983; Ed., Eiji Ishikawa et al., "Enzyme Immunoassay," Third Edition, IGAKU-SHOIN, 1987; Ed., Tsunehiro Kitagawa, "Protein Nucleic Acid Enzyme, Separate Volume, No. 31 Enzyme Immunoassay," KYORITSU SHUPPAN CO., LTD, 1987; Ed., Minoru Irie, "Radioimmunoassay," Kodansha Scientific Ltd., 1974; and Ed., Minoru Irie, "Radioimmunoassay 2,"Kodansha Scientific Ltd., 1979). As the above solid-phase support, an insoluble support in the form of beads, microplates, test tubes, sticks, or test pieces made of material such as polystyrene, polycarbonate, polyvinyl toluene, polypropylene, polyethylene, polyvinyl chloride, nylon, polymethacrylate, latex, gelatin, agarose, cellulose, sepharose, glass, metal, ceramics, or magnetic material can be used herein. The anti-HCV antibody or HCV particles of the present invention can be immobilized via binding to a solid-phase support by a known method such as a physical adsorption method, a chemical binding method, or a combination thereof.

As labeling substances for labeling the anti-HCV antibody: peroxidase (POD), alkaline phosphatase, β-galactosidase, urease, catalase, glucose oxidase, lactate dehydrogenase, amylase, a biotin-avidin complex, or the like can be used in the case of ELISA; fluorescein isothiocyanate, tetramethylrhodamine isothiocyanate, substituted rhodamine isothiocyanate, dichlorotriazine isothiocyanate, Alexa480, AlexaFluor488, or the like can be used in the case of fluorescence immunoassay; and tritium ($^3$H), iodine 125($^{125}$I), iodine 131 ($^{131}$I), or the like can be used in the case of radioimmunoassay. However, the examples are not limited to them. Also, in the case of luminescence immunoassay, an NADH-FMNH$_2$-luciferase system, a luminol-hydrogen peroxide-POD system, an acridinium ester system, a dioxetane compound system, or the like can be used. Regarding a method for binding a labeled antigen to an antibody, a known method such as a glutaraldehyde method, a maleimide method, a pyridyl disulfide method, or a periodic acid method can be used in the case of ELISA; and a known method such as a chloramine T method, or Bolton-Hunter method can be employed in the case of radioimmunoassay.

Also, the immunoassay of the present invention can be performed by measuring the generation of immune complex agglutinates resulting from immunonephelometry, latex agglutination reaction, latex turbidimetry, hemagglutination reaction or particle agglutination reaction through an optical method based on transmitted light or scattered light, or through a visual measurement method. In this case, phosphate buffer, glycine buffer, tris buffer, Good's buffer, or the like can be used as a solvent and further a reaction accelerator such as PEG or a non-specific reaction inhibitor may be contained.

A specific example in which the method for detecting HCV of the present invention is applied to ELISA is briefly explained below. First, the anti-HCV antibody of the present invention is immobilized on an insoluble support. In addition, not only 1 type, but also a plurality of types of antibody may be immobilized, as long as they can specifically recognize HCV particles. Next, a sample that can contain HCV particles is caused to act on the surfaces of immobilized antibodies, so that complexes of immobilized antibodies and HCV particles are formed on the surface of the support. Subsequently, the support is sufficiently washed with a washing solution, so as to remove unbound substances in the sample other than HCV particles. Furthermore, other anti-HCV-labeled antibodies specifically recognizing HCV particles are prepared. The labeled antibodies are caused to act on a support to which complexes of immobilized antibodies and HCV particles have been bound. After sufficient washing using a washing solution, HCV particles existing in the sample can be detected via detection using the label.

Also, labeled antibodies and a sample containing HCV particles are mixed in advance to form antigen-antibody complexes, so that the complexes can be caused to act on immobilized antibodies. When antibodies to be immobilized are labeled with biotin, biotinylated and immobilized antibodies, a sample containing HCV particles, and antibodies labeled with a label other than biotin are all mixed together, so as to form antigen-antibody complexes and to cause avidin to act on the solid-phased support. Thus, antigen-antibody complexes can be detected via labeling other than biotinylation.

Test strips for immunochromatography can also be used for the immunoassay of the present invention. A test strip for immunochromatography is composed of a sample receiving part comprising a material that easily absorbs a sample, a reagent part containing a diagnostic product of the present invention, a development part where a reaction product from the sample and the diagnostic product develops, a labeling part where the reaction product that has developed is colored, and a display part to which the colored reaction product develops, for example. For example, a commercially available diagnostic of pregnancy has a form similar to such a test strip. The principle of the measurement method is as described below. First, a sample is added to the sample-receiving part, and then the sample-receiving part absorbs the sample and then causes the sample to reach the reagent part. Subsequently, HCV in the sample and the above anti-HCV antibody conduct an antigen-antibody reaction at the reagent part, and then the reaction complex migrates in the development part to reach the labeling part. At the labeling part, a reaction takes place between the above reaction complex and a labeled secondary antibody. When the product resulting from the reaction with the labeled secondary antibody develops and reaches the display part, color development is observed. The above test strip for immunochromatography has extremely low invasiveness, providing no pain or risk due to the use of the reagent to users. Hence, the test strip can be used for monitoring in the home. Furthermore, the results can be precisely examined and/or treated (e.g., surgical excision) at the level of each medical institution, resulting in prevention of metastases and/or recurrences. Such a test strip is also advantageous in that it can be produced in large amounts at low cost.

According to the embodiments of the present invention, HCV particles and/or the envelope proteins thereof in a sample can be detected. Therefore, HCV infection via a donor's blood or organ can be prevented.

4. Kit for Detecting HCV

Another embodiment of the present invention is a kit for detecting HCV according to "3. Method for detecting HCV" above, which contains the anti-HCV antibody of the present invention. The kit for detecting HCV of the present invention can contain a labeled secondary antibody, a substrate required for detection of the label, a positive control or a negative control, a buffer to be used for dilution or washing of a sample, and/or instructions.

EXAMPLES

Hereafter, the present invention is described in greater detail with reference to the examples. It should be noted that these examples are provided for illustrative purposes and the technical scope of the present invention is not limited to these examples.

Example 1

Preparation of J6/JFH-1-HCV Particles cDNA (genomic cDNA) was obtained through reverse transcription of the total region of genomic RNA of the HCV JFH-1 strain (genotype 2a) isolated from a fulminant hepatitis patient. The thus obtained cDNA was cloned into a site downstream of a T7 RNA promoter sequence of a pUC19 plasmid. The obtained plasmid DNA (pJFH-1) was prepared according to the method described in Wakita, T. et al., Nat. Med., 11 (2005) p. 791-796 and International Patent Publication WO 2004/104198. The nucleotide sequence of genomic cDNA derived from the JFH-1 strain, which was inserted in pJFH-1, is as shown in SEQ ID NO: 1. The pJFH-1 was digested with EcoR I, and then partially digested with Bcl I. Thus, a plasmid DNA fragment was prepared by excising a fragment (about 2840 bp) ranging from the EcoR I site to the first Bcl I site, and then the plasmid DNA fragment was purified.

Meanwhile, HCV genomic cDNA derived from the J6CF strain (GenBank Accession No. AF177036, Yanagi, M., et al., Virology 262: 250-263 (1999)) was cloned into a site downstream of a T7 RNA promoter sequence of a pUC19 plasmid. The thus obtained plasmid DNA (pJ6CF) was prepared according to the method described in International Patent Publication WO 2006/022422. The pJ6CF was partially digested with EcoR I and Bcl I, the thus obtained about 2840-bp fragment was purified, and then the fragment was ligated to the pJFH-1 plasmid DNA fragment prepared by excision of the above EcoR I-Bcl I fragment, so that a plasmid DNA (pJ6/JFH-1) was obtained. DNA (SEQ ID NO: 2) cloned in the pJ6/JFH-1 is chimeric HCV genome cDNA in which the 5' untranslated region, the core sequence, the E1 sequence, the E2 sequence, and the p7 sequence, a sequence encoding the region ranging from the N-terminus to the $16^{th}$ amino acid residue of the NS2 protein derived from the genomic cDNA of the J6CF strain, and a sequence encoding the region ranging from the $17^{th}$ amino acid residue to the C-terminus of the NS2 protein, the NS3 sequence, the NS4A sequence, the NS4B sequence, the NS5A sequence, the NS5B sequence, and the 3' untranslated region derived from the genomic cDNA of the JFH-1 strain are linked in this order.

The thus prepared pJ6/JFH-1 was cleaved with Xba I, and then Mung Bean Nuclease 20 U (total amount of reaction solution: 50 μL) was added thereto, followed by 30 minutes of incubation at 30° C. Thus, the Xba I-cleaved end was blunt-ended. Phenol chloroform extraction and ethanol precipitation were performed, so that an Xba I-cleaved fragment, from which 4 bases (CTAG) at the cohesive end had been removed, was obtained. RNA was synthesized using the thus cleaved plasmid as a template and a MEGAscript T7 kit (Ambion) (see WO 2006/022422). The thus synthesized HCV genomic RNAs were each used for introduction into cells, as described below.

Huh7 cells ($3 \times 10^6$ cells) and 5 μg of each HCV RNA were suspended in a Cytomix solution (120 mM KCl, 0.15 mM $CaCl_2$, 10 mM $K_2HPO_4$/$KH_2PO_4$, 25 mM Hepes, 2 mM EGTA, 5 mM $MgCl_2$, 20 mM ATP, 50 mM glutathione (400 μL)) and then the suspension was transferred to a 4-mm cuvette. HCV RNA was electroporated into Huh7 cells using a Gene Pulser (BioRad) at 260 V and 950 μF. Thereafter, host cells for introduction of HCV genomic RNA were seeded in a 10 cm² dish, and then subcultured. During subculture, HCV core protein contained in culture supernatants was quantitatively determined using an HCV antigen ELISA test kit (Ortho Clinical Diagnostics), and thus production of HCV particles was confirmed. Culture supernatants in which the amounts of the core protein were high and the activity of producing HCV particles was high were selected and then stored as virus stocks.

The above obtained J6/JFH-1 virus stocks ($4 \times 10^4$ ffu/ml) were added in an amount of about 100 μL each to Huh7 cells cultured with 10% FCS-DMEM medium (containing 1% MEM nonessential amino acid solution (Invitrogen), 10 mM HEPES-Tris (pH 7.3), and 1 mM sodium pyruvate) in a 10-cm dish, so that Huh7 cells were infected with HCV virus.

The cells were adequately subcultured to prevent cells from becoming confluent, and culture expansion was carried out in 225 cm² flasks from one flask to 4 flasks and then 12 flasks. Subsequently, cells were detached from 8 of such 225-cm² flasks, and seeded in two 5-layer Cellstacks (registered trademark) (Corning), and a medium was added thereto in an amount of 650 mL/cellstack. The cells obtained from the remaining 4 flasks were seeded in 12 flasks and thus virus production was effectively continued.

On the day following subculture, the media were discarded and 650 mL of 2% FCS-DMEM (containing 1% MEM nonessential amino acid solution (Invitrogen), 10 mM HEPES-Tris (pH 7.3), 1 mM sodium pyruvate) was added. The media were recovered 3 days after medium exchange, passed through a 0.45-μm filter, and the resultants were stored in a deep freezer. Also, 650 mL of the above 2% FCS-DMEM was added to the Cellstacks after the culture supernatants had been recovered, and culture was continued. A similar procedure was repeated 2 days after medium exchange and the culture supernatants were recovered. A similar procedure was then repeated one more time. The culture supernatants recovered herein were used in Example 2 below.

As described above, cells, into which chimeric HCV genome RNA synthesized from pJ6/JFH-1 had been introduced, produced infectious HCV particles and the supernatant contained the thus produced infectious HCV particles mixed therein.

Example 2

Purification of J6/JFH-1 HCV Particles

Viral particles produced in Example 1 were purified using the following 3-stage process.
(1) Concentration and Diafiltration
With the use of Hollow Fiber Cartridge (GE Healthcare: 500 kDa cut-off, Model No. UFP-500-C-8A, hereinafter, referred to as "Hollow Fiber"), the culture supernatant containing the HCV particles obtained in Example 1 above was concentrated 60-fold.

(2) Density-Gradient Ultracentrifugation
To the Ultra-clear 25×89 mm centrifuge tube ((Beckman Coulter, Inc., Catalog No. 344058), 3 mL of TNE buffer (10 mM Tris-HCl (pH 7.4), 150 mM NaCl, 1 mM EDTA) containing cold 60% sucrose was added, and 7 mL of TNE buffer containing 20% sucrose was overlaid thereon. Further, 25 ml of the sample was overlaid onto the TNE buffer containing 20% sucrose. Ultracentrifugation was carried out using a SW-28 (Beckman Coulter) at 28,000 rpm for 4 hours at 4° C.

The bottom of the tube was perforated using the 25G injection needle (Terumo) and 12 fractions (1 mL each) were obtained. The specific gravity of the solution of each fraction was measured, so that the formation of sucrose density gradient was confirmed. The fractions with the $3^{rd}$, the $4^{th}$, and the $5^{th}$ highest specific gravity were recovered in descending order of their specific gravity, and then used for concentration and buffer exchange.
(3) Concentration and Buffer Exchange The elution fraction was subjected to buffer exchange and concentration using Amicon Ultra-15 Centrifugal Filter Units (molecular weight to be eliminated: 100 kDa, Millipore) and TNE buffer. The thus-obtained concentrate was used as a virus solution containing infectious HCV particles in the immunization step described below.

Example 3

Inactivation of HCV

HCV in the virus solution obtained in Example 2 above was inactivated via ultraviolet irradiation. As a source of ultraviolet rays, GL-15 (Toshiba) was used. The solution containing purified HCV particles having an infectious titer of $1 \times 10^6$ ffu/mL was introduced into a silicon-coated polyethylene Eppendorf tube (Assist Co., Ltd,), the tube was placed at a distance from the source of ultraviolet rays, so that the ultraviolet rays would be applied at the intensity of 20 mW/cm², and UV-C was applied for 5 minutes.

After ultraviolet irradiation, HCV particles were serially diluted 50-fold, 250-fold, 1.250-fold, 6.250-fold, 31.250-fold, 156.250-fold, and 781.250-fold in DMEM.

On the previous day, the Huh7 cells were seeded on a 96-well poly-L-lysine-coated plate (Corning 96 Well Clear Flat Bottom Poly-L-Lysine Coated Microplate, Corning) at $1 \times 10^4$ cells/well, the serially-diluted virus particles were seeded thereonto, and culture was conducted at 37° C. for 72 hours.

After the culture supernatant was removed, the plate was soaked in ice-cold methanol to fix the cells. Thereafter, methanol was removed via air drying, and cells were permeabilized with the use of Block Ace (registered trademark) (Dainippon Pharmaceutical Co., Ltd.) containing 0.3% Triton (registered trademark)-X 100 (GE Healthcare). HCV-infected cells were detected using the clone 2H9 anti-HCV-core antibody (Wakita, T. et al., Nat. Med. 11:791-796, 2005) and goat anti-mouse IgG-Alexa488 (Molecular Probes), and the number of HCV-infected cells was counted under a fluorescent microscope (IX-70; Olympus). The infectious titer of the ultraviolet-irradiated HCV was confirmed to be the same or below the detection limit. Inactivated J6/JFH-1-HCV particles, for which complete disappearance of infectivity had been demonstrated, were used for administration to mice in the Examples below.

Example 4

Immunization of Mice with Inactivated HCV Particles

An adjuvant for animals, MPL+TDM (Sigma: Sigma Adjuvant System, Catalog No. 56322) was used as an adjuvant. To 100 μl of a solution containing inactivated J6/JFH-1-HCV particles (equivalent to 2 μmol of the HCV core protein) described in Example 3, the equivalent amount of MPL+TDM was added to generate an emulsion. Generation of an emulsion was confirmed by preparing an adequate amount of water in a beaker, adding a drop of the relevant mixture on the liquid surface, and observing that the liquid would not disperse. Balb/c mice (7-week-old, females) were etherized, and the emulsion containing inactivated J6/JFH-1-HCV particles thus prepared was intraperitoneally administered thereto to immunize the mice.

Two weeks later, to 100 μL of a solution containing J6/JFH-1-HCV particles (equivalent to 2 pmol of the HCV core protein), the equivalent amount of MPL+TDM was added to generate an emulsion, and then mice were further immunized with the emulsion via intraperitoneal administration as described above. The emulsion was further administered intraperitoneally to mice 4 weeks later and 6 weeks later for further immunization.

Example 5

Measurement of Activity of Inhibiting HCV Infection in Blood Serum Derived from Mouse Immunized with Inactivated HCV Particles (1) Preparation of Infectious HCV-Like Particles (HCVpp)

HCVpp was prepared according to the method of Bartosch et al. (document: Bartosch, B. et al. (2003) J. Exp. Med., 197, 633-642). This method involves introducing 3 types of expression vector (a vector for expression of retrovirus Gag-pol, a vector for expression of HCV envelope proteins, and a retrovirus packaging vector for expression of a reporter gene) into animal cells for expression, packaging the reporter gene, and thus preparing a pseudo virus expressing the HCV envelope proteins on the viral surface.

pcDNA J6dC-E2 was used for preparing HCVpp having envelope proteins of genotype 2a. The plasmid is an expression vector constructed by cloning a nucleic acid encoding the $132^{nd}$ to the $750^{th}$ amino acid residues (a part of the core protein, the E1 protein, and the E2 protein) of the protein of the J6CF strain that is an HCV strain of genotype 2a (NCBI Protein Accession No. AAF01178.1) into pcDNA3.1.

Gag-Pol 5349 was used as an expression vector constructed by cloning the genes encoding gag and pol of a mouse leukemia virus thereinto. Luc126 was used as a retrovirus packaging vector constructed by cloning a luciferase gene thereinto.

293T cells were subcultured in 10% FCS-DMEM (containing 1% MEM nonessential amino acid solution (Invitrogen), 10 mM HEPES (pH 7.3), 1 mM sodium pyruvate, 100 units/ml penicillin, 100 μg/ml streptomycin (Gibco: Catalog No. 15140-122)) (hereinafter, referred to as "DMEM-10F"). Collagen-coated flasks (IWAKI: Catalog Nos. 4100-010 and 4160-010) were used for culture. 293T cells were seeded in collagen-coated 10-cm dishes (IWAKI: Catalog No. 4020-010) so that the concentration would be $2.5 \times 10^6$ cells/dish, and then cells were cultured overnight. Opti-MEM (Gibco: Catalog No. 11058), FuGENE6, and 3 types of construct (HCV envelope protein expression vectors pcDNA J6dC-E2, Gag-Pol 5349, and Luc126) were mixed in amounts below. Specifically, 500 μA of Opti-MEM, 21.6 of FuGENE6, 1 μg of pcDNA J6dC-E2, 3.1 μg of Gag-Pol 5349, and 3.1 μg of Luc126 were mixed (or mixed at the same mixing ratio), and then incubated at room temperature for 15 minutes. Each medium for 293T cells was exchanged with Opti-MEM (7.5 mL), DNA complex was added thereto, and then incubation was performed at 37° C. and 5% $CO_2$ for 6 hours. After completion of reaction, cells were washed once with PBS, DMEM-10F (8 mL) was added, and then incubation was performed at 37° C. and 5% $CO_2$ for 48 hours. After completion of culture, supernatants were recovered, and then filtered with a 0.45-μm filter, so that an HCVpp solution was obtained. The HCVpp solution was dispensed 1 mL each and then stored at −80° C.

The thus obtained infectious HCV-like particles having structural proteins of the J6CF strain of genotype 2a are referred to as "J6CF HCVpp."

(2) Measurement of Activity of Inhibiting Hcv Infection

Normal mouse serum before administration of HCV particles, and 200 μL of serum from blood collected on day 49 after primary immunization of a mouse with inactivated HCV particles (J6/JFH-1-HCV particles) as described in Example 4 were separately applied to 1 mL of a protein G sepharose column (GE Healthcare). After the columns were washed with PBS, the samples were eluted with 0.1 M glycine buffer (pH 3.0) in amounts of 1 mL/fraction. Immediately after elution, 1 M Tris-HCl (pH 9.5) was added to return the pH to netural. The activity of inhibiting HCV infection of the fraction was measured for the peak fraction of the eluted protein as an IgG fraction. Specifically, the IgG fraction sample was diluted with DMEM (DMEM containing 10% FCS (invitrogen), 1% MEM nonessential amino acid solution (Invitrogen), 10 mM HEPES-Tris (pH 7.3), 1 mM sodium pyruvate) so that the final IgG concentration would be 10, 30, 100, and 200 μg/mL. Then the dilutions were separately added to the J6CF HCVpp solution obtained via the process of "(1) Preparation of infectious HCV-like particles (HCVpp)" in the Examples. Incubation was performed at 37° C. for 30 minutes. Media of Huh7.5.1 cells (cultured on the previous day on 96-well plates at $1 \times 10^4$ cells/well) were discarded, IgG fraction samples were added, and then incubation was performed. The resulting virus solution was added at 50 μL/well and then incubation was performed at 37° C. for 3 hours. After the virus solution was discarded, washing was performed once with PBS at 100 μL/well, 200 μL/well medium was added and then incubation was performed at 37° C. for 72 hours. After medium was discarded, 25 μL/well DMEM (no serum had been added) and 25 μL/well Steady-Glo (Promega: Catalog No. E2520) were added, and then cells were lysed according to the instructions included therewith. The cell lysis solution (40 μL/well) was transferred to a white 96-well plate (Sumitomo Bakelite Co., Ltd.: Catalog No. MS-8496W) and then luminescence intensity was measured using ARVO X4 (PerkinElmer).

The results are shown in FIG. 1. The vertical axis in FIG. 1 indicates luciferase activity represented by luminescence intensity and the numerical values indicated by the horizontal axis are concentrations (μg/mL) of IgG mixed with the J6CF HCVpp solution. Also, "Control" indicates a positive control to which no antibody was added, and "Normal mouse mIgG" indicates a control antibody. The value obtained when the J6CF HCVpp solution had been mixed with DMEM was shown as a control indicating 100% infection. The lower the luminescence intensity shows the higher the activity of inhibiting infection. The IgG fraction derived from the serum of a mouse to which J6/JFH-1-HCV particles had been administered was observed to exhibit the activity of inhibiting HCV infection in a dose-dependent manner.

Example 6

Preparation of Hybridoma

A mouse myeloma cell line SP2/0 (obtained from ECACC) was cultured in DMEM (Invitrogen) containing $5 \times 10^{-5}$ M 2-mercaptoethanol, 100 units/mL penicillin, 100 μg/mL streptomycin, and 10% FCS (Invitrogen), so that SP2/0 cells in the logarithmic growth phase were obtained. The cells were washed 3 times with serum-free DMEM.

Next, spleen cells were extracted from a mouse to which HCV particles (J6/JFH-1-HCV particles) had been administered in Example 4, and then washed 3 times with serum-free DMEM. SP2/0 cells and mouse spleen cells were added to a 50-mL centrifugal tube at a ratio of 1:5, followed by 10 minutes of centrifugation at 1,000 rpm. The supernatant was completely aspirated off, and the bottom of the tube was tapped with fingers to loosen the cell pellet. 1 mL of 50% PEG-1500 solution (Roche) heated at 37° C. was added to the cells for 1 minute, and the reaction was allowed to continue at 37° C. for 1 minute. Subsequently, 1 mL of serum-free DMEM was gradually added for 1 minute, and 1 mL of serum-free DMEM was gradually added again for 1 minute. In the end, 7 mL of serum-free DMEM was added for 3 minutes to dilute the PEG solution. The cells in the diluent were centrifuged at 1,000 rpm for 10 minutes, 50 mL of HT medium (DMEM containing $5\times10^{-5}$M 2-mercaptoethanol, 100 units/mL penicillin, 100 μg/mL streptomycin, 10% FCS, $10^{-4}$M hypoxanthine, and $1.5\times10^{-5}$M thymidine) was added thereto, and the cell pellet was loosened via pipetting. The cells were transferred to two 75-cm$^2$ flasks and cultured at 37° C. in a 5% $CO_2$ incubator overnight.

The cells were centrifuged at 1,000 rpm for 10 minutes and recovered. The cell pellet was loosened via tapping and suspended in 10 mL of DMEM. The cell suspension was added to and thoroughly mixed in 90 mL of methylcellulose HAT selective medium (Stem Cell Technology), the resultant was added to 10-cm dishes in amounts of 10 mL per dish, and culture was conducted at 37° C. in a 5% $CO_2$ incubator.

After the culture for 10 to 14 days, hybridoma colonies, each of which was considered to have grown from a single cell, were suctioned with a pipette chip, and introduced into each well of a 96-well plate, to which 200 μl of HT medium containing 10% hybridoma growth factors (Bio Veris) had been added, and culture was then conducted.

Example 7

Screening of Hybridomas Producing HCV-Infenction-Inhibiting Antibody

When the hybridomas prepared in Example 6 had sufficiently proliferated, the culture supernatants were recovered, and screening was carried out as follows.

Screening was carried out by immobilizing the E1 and E2 proteins on a plate, evaluating whether or not the antibodies in the hybridoma supernatant would bind to the proteins via EIA, and evaluating whether or not the antibodies in the hybridoma supernatant would be able to inhibit HCV infection (described in Example 8).

(1) Preparation of E1 Protein and E2 Protein Derived from the J6CF Strain

The E1 and E2 proteins of the J6CF strain were prepared as follows. With the use of genomic cDNA derived from the J6CF strain of genotype 2a (GenBank Accession Number AF177036) as a template, a gene encoding the E1 protein lacking a transmembrane region, which is equivalent to a region ranging from the $192^{nd}$ to the $352^{nd}$ amino acid residues when the initiator methionine at the N terminus of the full-length protein sequence of J6CF (i.e., the continuous protein sequence encoded by the genome sequence of the J6CF strain: the amino acid sequence under GenBank Accession Number AF177036) was regarded as the $1^{st}$ amino acid residue, was amplified via PCR using the Advantage GC2 PCR kit (Takara Bio) with J6E1dTM-s (SEQ ID NO: 3: CACAAGCTTGCCGAAGTGAAGAACATCAGT) and J6E1dTM-as (SEQ ID NO: 4: GCTCTAGATTAATGAGC-CCCGCTAATGATGTC). The amplified DNA fragment was cloned into pCR-TOPO (Invitrogen), and 3 clones were subjected to nucleotide sequence analysis. A clone containing an insert having a correct nucleotide sequence was designated as pTOPO-J6E1dTM.

pTOPO-J6E1dTM was digested with Hind III and Xba I and a gel containing the resultant DNA fragment of approximately 500 bp (the E1 fragment) was excised. The DNA fragment was purified from the gel using GeneElute (SIGMA). Similarly, p3×FLAG-CMV-9 (SIGMA) was digested with Hind III and Xba I, the resultant was electrophoresed on 1% agarose gel, a gel containing a fragment of approximately 6,400 bp was excised, and the DNA fragment was purified from the gel using GeneElute (SIGMA). The purified DNA fragments were ligated to each other using T4 ligase (Takara Bio), thereby obtaining a CMV-3× FLAGJ6E1dTM animal cell expression vector into which the E1 fragment of the J6CF strain had been incorporated.

Subsequently, a gene encoding the E2 protein lacking a transmembrane region, which is equivalent to a region ranging from the $384^{th}$ to the $720^{th}$ amino acid residues when the initiator methionine at the N terminus of the full-length protein sequence of the J6CF strain was regarded as the $1^{st}$ amino acid residue, was amplified via PCR using the Advantage GC2 PCR kit (Takara Bio) with J6E2dTM-s (SEQ ID NO: 5: CACAAGCTTCGCACCCATACTGTTGGGG) and J6E2dTM-as (SEQ ID NO: 6: GCTCTAGATTACCATCG-GACGATGTATTTTGT). The amplified DNA fragment was cloned into pCR-TOPO (Invitrogen), and 3 clones were subjected to nucleotide sequence analysis. A clone containing an insert having a correct nucleotide sequence was designated as pTOP0-J6E2dTM.

Subsequently, DNA obtained by digesting p3×FLAG-CMV-9 (SIGMA) with Hind III and Xba I was ligated to the DNA fragment of approximately 1,000 bp excised from pTOP0-J6E2dTM with Hind III and Xba I with the aid of T4 DNA ligase for cyclization. The resulting vector was designated as CMV-3×FLAGJ6E2dTM.

CMV-3×FLAGJ6E1dTM or CMV-3×FLAGJ6E2dTM was introduced into the COS1 cells derived from monkey kidney cells (Accession Number RCB0143, obtained from Riken Cell Bank) as follows to express the E1 or E2 proteins therein.

The COS1 cells were cultured in DMEM (Invitrogen) containing 10% FCS (Invitrogen), 100 U/mL penicillin, and 100 μg/mL streptomycin sulfate. The COS1 cells were seeded in a 150-cm$^2$ culture flask (Corning Coaster) at a split ratio of 1:2 on the previous day of gene introduction, and the cells were cultured at 37° C. in a 5% $CO_2$ incubator overnight.

Separately, DEAE dextran (Pharmacia) and chloroquine (SIGMA) were added to DMEM (Invitrogen) to final concentrations of 400 μg/ml and 100 μM, respectively, 500 μL (50 μg) of the expression vector (CMV-3×FLAGJ6E1dTM or CMV-3×FLAGJ6E2dTM) was added at 0.1 μg/μL to 13 mL of said solution, and culture was then conducted (the solution was designated as a DEAE dextran-DNA mixture). Subsequently, the supernatant of the cultured COS1 cells was aspirated off, and 10 mL of PBS(−) (Nissui) was added thereto and the cells were washed once. After PBS(−) was aspirated off, 13 mL of the DEAE dextran-DNA mixture was added thereto per 150-cm$^2$ flask, and incubation was then carried out at 37° C. in the presence of 5% $CO_2$ for 4 hours.

4 hours later, the DEAE dextran-DNA mixture was aspirated off, and the cells were washed once with 10 mL of PBS. CHO-SFM medium (Invitrogen) was added at 50 mL per flask, and culture was conducted at 37° C. in the presence of 5% $CO_2$. After 4 days, the culture supernatant was collected in a 50-mL centrifuge tube (Corning Coaster). The collected supernatant was centrifuged at 6,000 rpm (with the use of a HITACHI RPR9-2 rotor) for 30 minutes at 4° C. and filtered through a 0.2-μm filter (Whatman).

The culture supernatant was purified with the use of anti-FLAG M2 agarose (SIGMA) as follows. To 500 mL of the culture supernatant, 1 mL of anti-FLAG M2 agarose was added, and the reaction was allowed to proceed at 4° C. (in a low-temperature chamber) while undergoing agitation in a spinner bottle. After 2 hours, a mixture of the supernatant and anti-FLAG M2 agarose was transferred to the Econo-Column (BIO-RAD), and flow-through fractions were collected. Subsequently, the column was washed twice with 10 mL of TBS (50 mM Tris-HCl, 150 mM NaCl, pH 7.4). Six fractions (1 mL of each fraction) were eluted with the use of 0.1 M glycine-HCl (pH 3.5). Immediately after elution, 1M Tris-HCl (pH 9.5) was added for neutralization. The fractions (20 μL each) were subjected to SDS-polyacrylamide gel electrophoresis under reductive conditions and stained with Coomassie brilliant blue. As a result, the E1 protein or E2 protein derived from the J6CF strain was confirmed to be purified.

(2) Preparation of Plate with E1 Protein and E2 Protein Immobilized Thereon

The E1 and E2 proteins derived from the J6CF strain were each diluted with PBS to 1 μg/mL. The mixed protein solution (50 μA) of the E1 and E2 proteins was added to each well of the immunoplate (NUNC), the plate was allowed to stand at 4° C. overnight, and the proteins were immobilized on the plate. The protein solution was removed, 150 μL of Block Ace (Dainippon Pharmaceutical Co., Ltd.) was added to each well, and the plate was subjected to blocking at room temperature for 4 hours.

These plates were used for screening for the anti-HCV antibody in the culture supernatants of hybridomas, as described below.

(3) Screening of Culture Supernatant of Hybridoma Prepared Using J6/JFH-1-HCV Particle as an Antigen The plate prepared in (2) above upon which the E1 and E2 proteins derived from the J6CF strain had been immobilized was washed 4 times with PBS containing 0.1% Tween 20 (SIGMA), 50 μl, of each hybridoma supernatant sample obtained in Example 6 was added to each well, and the reaction was allowed to proceed at room temperature for 1 hour while the plate was shaken with a plate mixer for reaction. After the reaction, the plate was washed 4 times with PBS containing 0.1% Tween 20 (SIGMA), 50 μl of the HRP-labeled anti-mouse IgG antibody (SIGMA), which had been diluted 10,000-fold with PBS containing 0.1% Tween 20, was added to each well, and the reaction was allowed to proceed at room temperature for 1 hour while the plate was shaken. After the reaction, the plate was washed 4 times with PBS containing 0.1% Tween 20 (SIGMA), color was developed using a color development kit for peroxidase (Sumitomo Bakelite Co., Ltd.), the absorbance at 450 nm was measured using Multi-Scan (Titer-Tech), and positive clones were selected.

Example 8

Evaluation of the Activity of Inhibiting HCV Infection

A hybridoma supernatant was added to the J6CF HCVpp solution obtained via the process of "(1) Preparation of infectious HCV-like particles (HCVpp)" in Example 5 and then incubation was performed at 37° C. for 30 minutes. After the removal of the medium from Huh7.5.1 cells cultured on the previous day on a 96-well plate at $1 \times 10^4$ cells/well, the virus solution incubated after addition of the hybridoma supernatant was added at 50 μL/well, and then incubation was performed at 37° C. for 3 hours. After the virus solution was discarded, the plate was washed once with 100 μL/well of PBS, a medium was added at 200 μL/well, and then incubation was performed again at 37° C. for 72 hours. The medium was discarded, 25 μL/well of DMEM (serum-free) and 25 μL/well of Steady-Glo (Promega: Catalog No. E2520) were added, and thus cells were lysed according to instructions included therewith. The cell lysis solution was transferred at 40 μL/well to a white 96-well plate (Sumitomo Bakelite Co., Ltd.: Catalog No. MS-8496W) and then luminescence intensity was measured using ARVO X4 (PerkinElmer). Luminescence intensity when the above test was simultaneously conducted with a virus solution prepared by mixing the J6CF HCVpp solution with DMEM (in an amount equivalent to the hybridoma supernatant) was regarded as representing 100% infection. Therefore, luminescence intensity after mixing with a hybridoma supernatant was expressed with percentages (%), and thus infection (%) was found.

Two types of samples with low infection (%) were selected as hybridoma cell line producing monoclonal antibodies having the activity of inhibiting HCV infection. These cell lines were cloned with limiting dilution, so that the P18-9E hybridoma cell line producing the P18-9E monoclonal antibody and the P19-7D hybridoma cell line producing the P19-7D monoclonal antibody were obtained.

The P18-9E hybridoma cell line (Accession No: FERM BP-11263) and the P19-7D hybridoma cell line (Accession No: FERM BP-11264) selected in the Examples were deposited at the International Patent Organism Depositary of the National Institute of Advanced Industrial Science and Technology (Central 6, 1-1-1 Higashi, Tsukuba, Ibaraki, 305-8566, Japan) as of 15 Oct. 2009.

These hybridoma cell lines can be appropriately cultured at 37° C. using medium prepared by adding 1 mM sodium pyruvate, 55 μM 2-mercaptoethanol, and 10% FCS to DMEM.

Example 9

Analysis of HCV Infection-Inhibiting Monoclonal Antibody

Properties of HCV infection-inhibiting monoclonal antibodies produced from the hybridoma cell lines obtained in Example 8 were analyzed as follows. In addition, a monoclonal antibody produced from the P18-9E hybridoma cell line (Accession No: FERM BP-11263) was designated as "P18-9E monoclonal antibody," and a monoclonal antibody produced from the P19-7D hybridoma cell line (Accession No.: FERM BP-11264) was designated as "P19-7D monoclonal antibody."

(1) Antibody Subclass

Mouse antibody subclass was analyzed using the culture supernatants of hybridomas and a Mouse MonoAB ID KIT (Invitrogen). The result of analyzing the isotype of the P18-9E monoclonal antibody demonstrated that the isotype was IgG2b since the H chain was revealed to be γ2b and the L chain was revealed to be κ. The result of analyzing the isotype of the P19-7D monoclonal antibody demonstrated that the isotype was IgG1 since the H chain was revealed to be γ1 and the L chain was revealed to be κ.

(2) Purification

Hybridomas were cultured in Hybridoma SFM serum free medium (Invitrogen) until confluent. The culture solution was then collected in a centrifugation tube and then centrifugation was performed at 1500 rpm for 5 minutes. The culture supernatant was added to Prosep-G (Millipore) and then washed with 20 bed volumes of PBS. Subsequently, 6 fractions were eluted with 1 bed volume of 0.1 M glycine-HCl (pH 3.0). Immediately after elution, 1 M Tris-HCl (pH 9.5) was added for neutralization. The absorbance at 280 nm of each fraction was measured using NanoDrop (NanoDrop Technologies, ND-1000). Fractions (OD280 nm>0.1) containing the proteins were collected. Buffer exchange with PBS was performed while concentrating using Amicon Ultra 50 K (Millipore), and then filtration was performed with a 0.22-μm filter. The concentrated sample (20 μl) was subjected to SDS-polyacrylamide gel electrophoresis under reductive conditions and non-reductive conditions, and then stained with Coomassie brilliant blue, so that the protein was confirmed to be IgG. The absorbance at 280 nm of the sample was measured, and then the amount of the antibody contained in the solution (10 mg/mL IgG=13.7 OD (based on OD)) was calculated.

(3) The Activity of Inhibiting HCV Infection of Purified Monoclonal Antibody

A. Activity of Inhibiting HCV Infection Against Infectious HCV-Like Particles (J6CF HCVpp)

The purified P18-9E monoclonal antibody or the purified P19-7D monoclonal antibody was added to the J6CF HCVpp solution obtained via the process of "(1) Preparation of infectious HCV-like particles (HCVpp)" in Example 5 and then incubation was performed at 37° C. for 30 minutes. The purified P18-9E monoclonal antibody and the purified P19-7D monoclonal antibody were diluted with PBS so that the final concentration would be 100 μg/ml and 300 μg/ml, respectively, and then used.

Huh7.5.1 cells were subcultured in 10% FCS-DMEM (containing 1% MEM nonessential amino acid solution (Invitrogen), 10 mM HEPES (pH 7.3), 1 mM sodium pyruvate, 100 units/ml penicillin, and 100 μg/mL streptomycin (Gibco: Catalog No. 15140-122)).

After medium was discarded from Huh7.5.1 cells cultured on the previous day on a 96-well plate at $1 \times 10^4$ cells/well, the virus solution to which a purified monoclonal antibody had been added and then incubated was added at 50 μL/well. Incubation was performed at 37° C. for 3 hours. After the virus solution was discarded, washing was performed once with 100 μL/well of PBS, 200 μL/well medium was added, and then incubation was performed at 37° C. for 72 hours. After the medium was discarded, 25 μL/well of DMEM (serum-free) and 25 μL/well of Steady-Glo (Promega: Catalog No. E2520) were added and then cells were lysed according to instructions included therewith. The cell lysis solution was transferred at 40 μL/well to a white 96-well plate (Sumitomo Bakelite Co., Ltd.: Catalog No. MS-8496W), and then luminescence intensity was measured using ARVO X4 (PerkinElmer). The luminescence intensity when the above test was simultaneously conducted with a virus solution prepared by mixing the J6CF HCVpp solution with PBS (in an amount equivalent to the diluted purified monoclonal antibody) was regarded as representing 100% infection. Luminescence intensity after mixing with the purified monoclonal antibody was expressed with percentages (%), and thus infection (%) was found.

Figure 2:
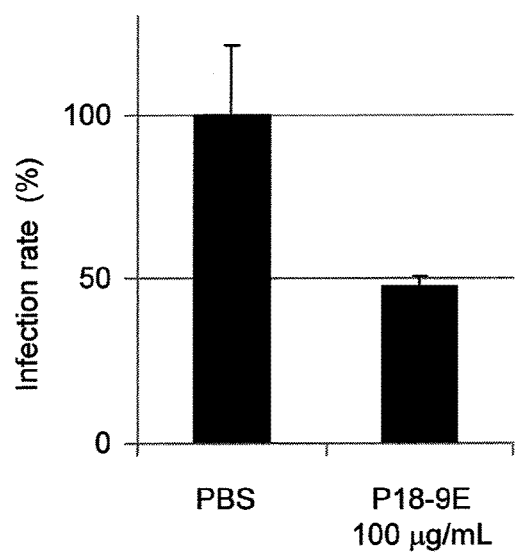
FIG. 2 shows the activity of inhibiting HCV infection of the P18-9E monoclonal antibody against J6CF infectious HCV-like particles.

FIG. 2 shows the activity of inhibiting HCV infection exhibited by the P18-9E monoclonal antibody. In FIG. 2, the vertical axis indicates infection (%), "PBS" along the horizontal axis indicates the result of a positive control to which no antibody was added, and "P18-9E 100 μg/mL" indicates the final concentration of the P18-9E monoclonal antibody mixed with the J6CF HCVpp solution. As shown in FIG. 2, the purified P18-9E monoclonal antibody inhibited infection with J6CF HCVpp.

Figure 3:
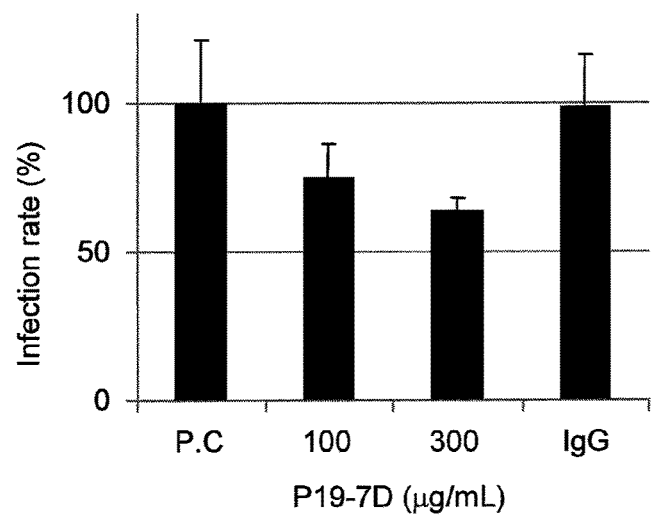
FIG. 3 shows the activity of inhibiting HCV infection of the P19-7D monoclonal antibody against J6CF infectious HCV-like particles.

FIG. 3 shows the activity of inhibiting HCV infection exhibited by the P19-7D monoclonal antibody. In FIG. 3, the vertical axis indicates infection (%), "P19-7D 100 μg/mL, 300 μg/mL" along the horizontal axis indicate the final concentrations of the P19-7D monoclonal antibody mixed with the J6CF HCVpp solution. Also, "P.C" indicates the result of a positive control to which no antibody was added, "IgG" indicates the result for the mouse IgG (300 μg/mL) as a control antibody. As shown in FIG. 3, the purified P19-7D monoclonal antibody inhibited infection with J6CF HCVpp.

B. Activity of Inhibiting HCV Infection Against Infectious HCV Particles (J6/JFH1 HCVcc)

The J6/JFH1-HCV particle solution (concentrate of the culture supernatant containing HCV particles) (hereinafter, referred to as "J6/JFH1 HCVcc") obtained via the process of (1) of Example 2 above was used as an HCVcc virus solution.

Huh7.5.1 cells were subcultured in 10% FCS-DMEM (containing 1% MEM nonessential amino acid solution (Invitrogen), 10 mM HEPES (pH 7.3), 1 mM sodium pyruvate, 100 units/mL penicillin, 100 μg/mL streptomycin (Gibco: Catalog No. 15140-122)). Huh7.5.1 cells were seeded on a 96-well plate (poly-D-lysin-coated) at $1 \times 10^4$ cells/well, and then cultured overnight. The J6/JFH1 HCVcc solution was mixed with the purified P18-9E monoclonal antibody and then incubated at room temperature for 30 minutes. At this time, the P18-9E monoclonal antibody was diluted with PBS to 20 μg/mL, 60 μg/mL, or 200 μg/mL and then used (the final concentration of the antibody in a mixture was 10 μg/mL, 30 μg/mL, or 100 μg/mL). After medium for cells was discarded, the virus solution incubated after addition of the antibody was added at 50 μL/well, and then incubation was performed at 37° C. for 3 hours. After the virus solution was discarded, washing was performed once with 100 μL/well of PBS, DMEM was added at 200 μL/well, and then incubation was performed at 37° C. for 72 hours. After removal of the culture supernatant, the plate was soaked in ice-cold methanol, so as to fix the cells. Thereafter, methanol was removed via air drying, a PBS solution containing 3% $H_2O_2$ was added at 100 μL/well, and then incubation was performed at room temperature for 5 minutes. After washing twice with 150 μL/well of PBS, Block Ace (registered trademark) (Dainippon Pharmaceutical Co., Ltd.) containing 0.3% Triton (registered trademark)-X 100 (GE Healthcare) was added at 100 μL/well, and then blocking was performed at room temperature for 1 hour. After washing twice with 150 μl/well of PBS, HRP-labeled anti-HCV-core antibody (Ortho Clinical Diagnostics) diluted 100-fold was added at 50 μL/well for reaction to proceed for 1 hour. Subsequently, the plate was washed 4 times with 150 μL/well of PBS, and then QuantaBlu (registered trademark) (PIERCE) reaction solution was added at 50 μL/well. The solution was allowed to stand at room temperature for 30 minutes, QuantaBlu stop solution was added at 50 μL/well to stop the reaction. The solution was transferred at 20 μl/well to a black 384-well plate (Corning: Catalog No. 3676). Fluorescence intensity was measured using ARVO X4 (PerkinElmer). The fluorescence intensity when the above test was simultaneously conducted with a virus solution prepared by mixing the J6/JFH1 HCVcc solution with PBS (in an amount equivalent to the diluted purified monoclonal antibody) was regarded as representing 100% infection. Fluorescence intensity after mixing with the purified monoclonal antibody was expressed with percentages (%), and thus infection (%) was found.

Figure 4:
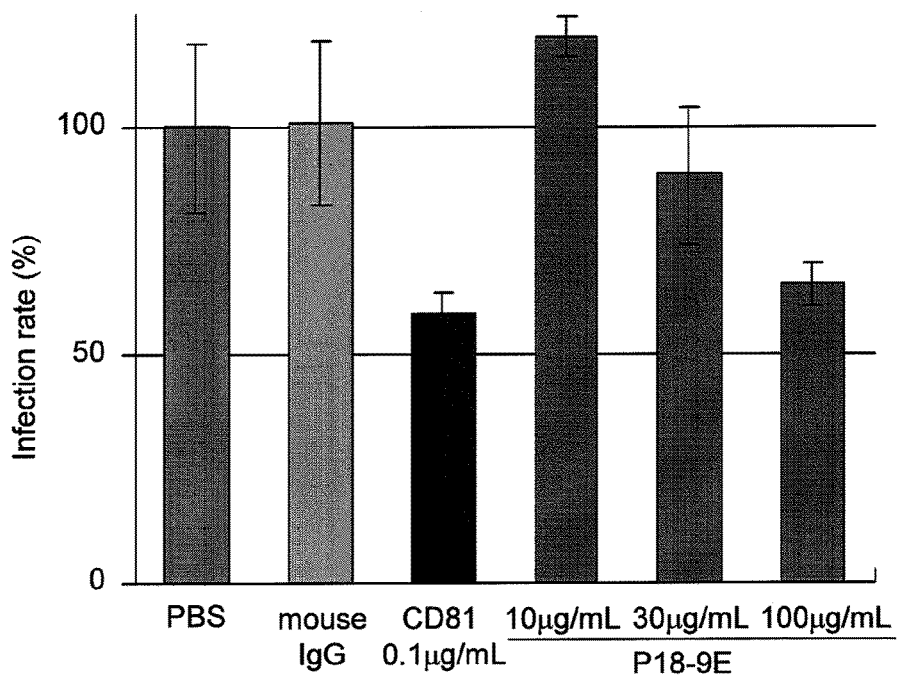
FIG. 4 shows the activity of inhibiting HCV infection of the P18-9E monoclonal antibody against J6/JFH1 infectious HCV particles.

The results are shown in FIG. 4. In FIG. 4, the vertical axis indicates infection (%), "P18-9E 10 µg/mL, 30 µg/mL, 100 µg/mL" along the horizontal axis indicate the final concentrations of the P18-9E monoclonal antibody mixed with the J6/JFH1 HCVcc solution. Also, "PBS" indicates the result of a positive control to which no antibody was added, "mouse IgG" indicates the result for a negative control antibody, "CD81 0.1 µg/mL" indicates the result for a positive control antibody. As shown in FIG. 4, the purified P18-9E monoclonal antibody inhibited infection with J6/JFH1 HCVcc.

These results demonstrated that the P18-9E and the P19-7D monoclonal antibodies are neutralizing antibodies having activity of inhibiting HCV infection.

(4) Analysis of Epitope of Monoclonal Antibody

Regarding the $1^{st}$ to the $162^{nd}$ amino acid residues (SEQ ID NO: 7) of the E1 protein in the J6CF strain and the $1^{st}$ to the $337^{th}$ amino acid residues (SEQ ID NO: 8) of the E2 protein in the J6CF strain, peptides consisting of amino acid sequences designed by shifting amino acid residues three by three from the N terminus of 10 continuous amino acids were synthesized. The N terminus of each peptide was biotinylated, and the C terminus of the same was glycine amide (the peptides were synthesized by JPT on consignment).

The synthesized peptides were dissolved in DMSO and then dissolved in PBS at 0.01 nmol/µL. 50 µL of the peptide solution was added to each well of the streptavidin-coated plate (Nunc) and the reaction was allowed to proceed at room temperature for 1 hour. Subsequently, the peptide solution was discarded, Blocking One (Nacalai Tesque) was added at 200 µL/well, and the plate was allowed to stand at room temperature for 5 hours. The Blocking One solution was discarded, the plate was washed 4 times with PBS (150 µL/well, pH 7.2) containing 0.05% Tween 20, the monoclonal antibody diluted to 1 µg/mL with PBS (pH 7.2) containing 0.05% Tween 20 was added at 50 µL/well, and the reaction was allowed to proceed at room temperature for 1 hour. Subsequently, the antibody solution was discarded, the plate was washed 5 times with 150 µL/well of PBS (pH 7.2) containing 0.05% Tween 20, the HRP-labeled anti-mouse IgG goat antibody (GE Healthcare) diluted 5.000-fold with PBS containing 0.05% Tween 20 was added at 50 and the reaction was allowed to proceed at room temperature for 1 hour. After the reaction, the antibody solution was discarded, and the plate was washed 5 times with 150 µL/well of PBS (pH 7.2) containing 0.05% Tween 20. Subsequently, antibodies bound to peptides were detected using a color development kit for HPR (Sumitomo Bakelite Co., Ltd.) and a spectrophotometer (OD 450 nm).

As a result, the purified P18-9E monoclonal antibody and the purified P19-7D monoclonal antibody did not react with any peptide. The result suggested that the P18-9E monoclonal antibody and the P19-7D monoclonal antibody are antibodies recognizing conformational epitopes.

(5) Cloning of DNA Encoding V Region of Monoclonal Antibody

DNA encoding a V region of the mouse monoclonal antibody against HCV particles was cloned as follows.

Total RNA was prepared from the hybridoma cell line using PureLink Micro-to-Midi (Invitrogen) in accordance with the method described in manuals included therewith. Specifically, $2 \times 10^6$ cells of the P18-9E hybridoma cell line and $2 \times 10^6$ cells of the P19-7D hybridoma cell line were each suspended in 0.5 mL of RNA lysis solution, and the cells were passed through a syringe with a 18 gauge needle several times for homogenization. The resulting homogenate was centrifuged, 70% ethanol was added to the same amount of the resulting supernatant, and the mixture was applied on an RNA spin cartridge. The cartridge was thoroughly washed with the addition of a washing solution and RNA was eluted with RNase-free water.

With the use of IgG-µ-type H-chain- and IgG-κ-type L-chain-specific 3' primers of Mouse Ig-Primer Set (Novagen), single-stranded cDNA was synthesized from total RNA. Specifically, to 3 µg of each RNA, 2 pmol of the g-type H-chain-specific 3' primer or the κ-type L-chain-specific 3' primer, and then 1 µl of a 10 mM dNTPs solution were added. Moreover, distilled water was added so that the final volume would be 13 µL, annealing was performed at 65° C. for 10 minutes, and then the solution was left to stand on ice. To the solution, 1 µL of 0.1 M DTT, 1 µL, of RNA OUT, 4 µL of 5×RT buffer included with SuperScriptIII (Invitrogen), and 1 µL of reverse transcriptase SuperScriptII (Invitrogen) were added for reaction to proceed at 50° C. for 60 minutes and then 70° C. for 15 minutes. After stored at 4° C., the solution was directly used for the next step, polymerase chain reaction (PCR). PCR was performed using a Mouse Ig-Primer Set as a primer set for PCR according to the conditions as in manuals included therewith. PCR was performed using GeneAmp (registered trademark) PCR System 9700 (Applied Biosystems) and Advantage GC2 DNA polymerase kit (TAKARA). Specifically, for amplification of H chains, PCR was performed using a primer (hybridizing to the leader sequence of mouse µ-type H-chain) ranging from MuIgVH5'-A to MuIgVH5'-F and a MuIgGVH3'-1 primer (hybridizing to mouse µ-type CH) included with the kit. For amplification of L chains, PCR was performed using a primer (hybridizing to the leader sequence of mouse κ-type L-chain) ranging from MuIgκVL5'-A to MuIgκVL5'-F and a MuIgκVL3'-1 primer (hybridizing to mouse x-type CL) included with the kit. To 1-4 µL of the above-prepared reaction mixture resulting from single-stranded cDNA synthesis, 10 µL of 5×PCR buffer included with the Advantage GC2 DNA polymerase kit, 5 µL of GC Melt, 5 µL of 2 mM dNTPs solution, 1 µL, of Advantage GC2 DNA polymerase mix, 2-5 pmol of MuIgκVL 5' primer, and 2 pmol of MuIgκVL3'-1 primer were added. Distilled water was further added so that the final volume would be 50 µL. 50 µL of the PCR solution was incubated at 94° C. for 3 minutes and then performed a thermal cycle at 94° C. for 1 minute, 60° C. for 1 minute, and 72° C. for 2 minutes, in that order. This thermal cycle was repeated 40 times and the reaction mixture was further incubated at 72° C. for 6 minutes.

For cloning of a DNA fragment amplified by the PCR method as described above, a TOPO TA Cloning kit (Invitrogen) was used. The pCR-TOPO vector included with the kit, the DNA fragment, and a salt solution included with the kit were added, the mixture was allowed to stand at room temperature for 5 minutes, and a part of the reaction solution was added to competent cells of E. Coli DH5α (TAKARA). The E. Coli competent cells were placed on ice for 30 minutes, subsequently heated at 42° C. for 45 seconds, and placed again on ice for 2 minutes. SOC medium (room temperature) was added thereto, the cells were cultured at 37° C. for 1 hour and seeded on an agar medium, and then cultured at 37° C. overnight. Plasmid DNA was prepared from the resulting transformant, and the nucleotide sequence of the cloned DNA was determined in accordance with a conventional technique.

(6) Analysis of Nucleic Acid Sequence of cDNA Encoding V Region of Monoclonal Antibody The nucleotide sequences of which were determined in (5) above and then DNAs (cDNAs encoding VH and VL, respectively, of the mouse monoclonal antibody) cloned in the plasmids were analyzed as follows.

Regarding the H chains of the P18-9E monoclonal antibody, 6 clones resulting from cloning of the PCR product amplified with the use of the MuIgVH5'-B 5' primer were analyzed. As a result, 1 out of the 6 clones was observed to have a substitution at one position in the nucleotide sequence, but the 5 clones had the same V region nucleotide sequences. DNA samples from which the 5 clones had been obtained were selected, and then the nucleotide sequence of the H-chain cDNA of the P18-9E monoclonal antibody was determined (SEQ ID NO: 9).

Regarding the L chains of the P18-9E monoclonal antibody, 3 clones resulting from cloning of the PCR product amplified with the use of the MuIgκVL5'-F 5' primer were analyzed. As a result, 1 out of the 3 clones was observed to have substitutions at two positions in the nucleotide sequence, but the 2 clones had the same V region nucleotide sequences. Bases at the 2 substitution positions in the 2 clones were selected, and then the nucleotide sequence of the L-chain cDNA of the P18-9E monoclonal antibody was determined (SEQ ID NO: 10).

Regarding the H chains of the P19-7D monoclonal antibody, the nucleotide sequences obtained from 6 clones resulting from cloning of the product amplified with the use of the MuIgVH5'-C 5' primer were analyzed. As a result, 1 out of the 6 clones was observed to have substitutions at 3 positions in the nucleotide sequence, but the remaining 5 clones had the same bases at the 3 positions. Bases at the 3 substitution positions in the 5 clones were selected, and then the nucleotide sequence of the H-chain cDNA of the P19-7D monoclonal antibody was determined (SEQ ID NO: 11).

Regarding the L chains of the P19-7D monoclonal antibody, 4 clones resulting from cloning of the PCR product amplified with the use of the MuIgκVL5'-G 5' primer were analyzed. As a result, 1 out of the 4 clones was observed to have substitutions at 2 positions in nucleotide sequence of the V region, but the 3 clones had the same nucleotide sequences. Bases at the 2 positions in the 3 clones were selected, and then the nucleotide sequence of the L-chain cDNA of the P19-7D monoclonal antibody was determined (SEQ ID NO: 12).

Figure 5:
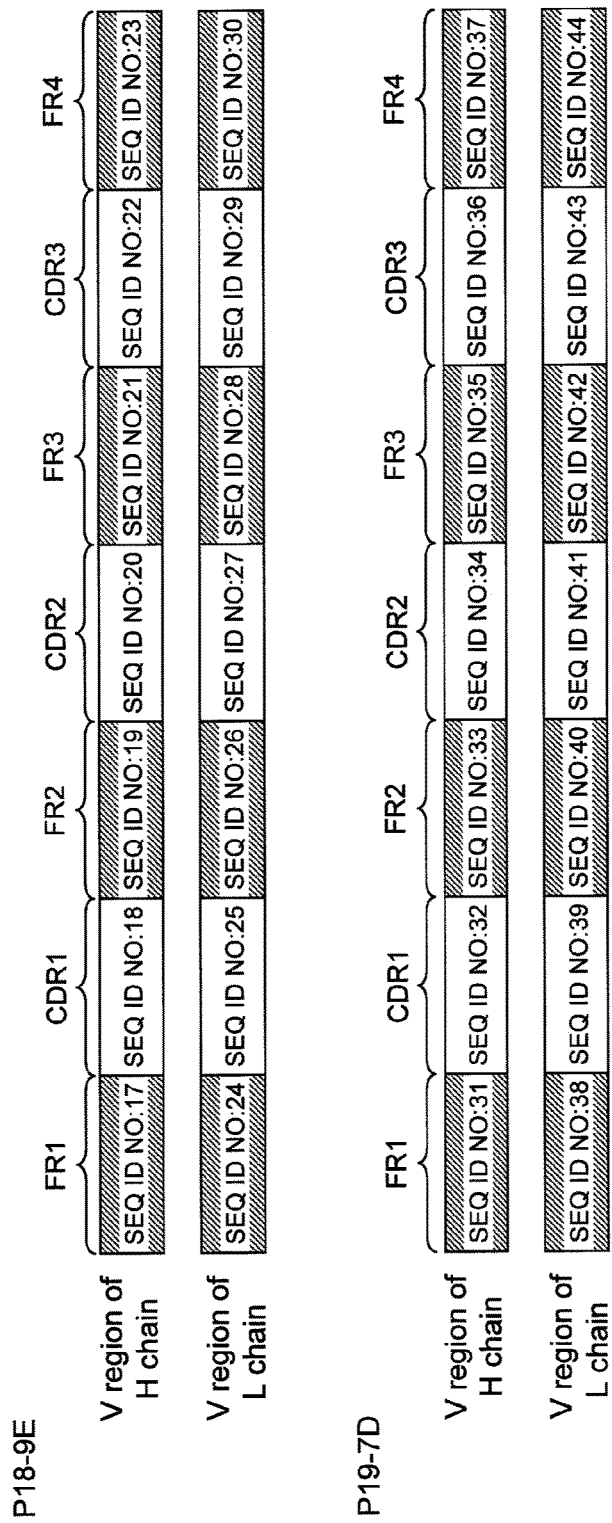
FIG. 5 shows SEQ ID NOs of the amino acid sequences of complementarity determining regions (CDRs) and framework regions (FRs) in the heavy chain and light chain variable regions of the P18-9E monoclonal antibody and the P19-7D monoclonal antibody.

Also, through a search of a database for encoded amino acid sequences deduced from the nucleic acid sequences, amino acid sequences ranging from FR1 to FR4 (J region) of V-regions in H-chain and L-chain of the P18-9E monoclonal antibody and the P19-7D monoclonal antibody were deduced (SEQ ID NOs: 13-16). Further, CDR1 to CDR3 deduced from the amino acid sequences are shown in FIG. 5.

The amino acid sequence of FR1 of the VH of the P18-9E monoclonal antibody is DAQGQMQQSGPELVKPGAS-VKLSCKTTDFTFN (SEQ ID NO: 17), the amino acid sequence of CDR1 of the same is RNYIS (SEQ ID NO: 18), the amino acid sequence of FR2 of the same is WLRQK-PGQSLEWIA (SEQ ID NO: 19), the amino acid sequence of CDR2 of the same is WIYAGTGGTKYNQKFTG (SEQ ID NO: 20), the amino acid sequence of FR3 of the same is KAQMTVDTSSHTAYMQFSNLTTEDSAVYYCAR (SEQ ID NO: 21), the amino acid sequence of CDR3 of the same is YLFDGYYIPLFDY (SEQ ID NO: 22), and the amino acid sequence of FR4 of the same (also referred to as J region, J segment, or J chain) is WGQGTTLTVS (SEQ ID NO: 23).

The amino acid sequence of FR1 of the VL of the P18-9E monoclonal antibody is AQCDVQITQSPSYLAASPGETIS-INC (SEQ ID NO: 24), the amino acid sequence of CDR1 of the same is RANKSIDKYLA (SEQ ID NO: 25), the amino acid sequence of FR2 of the same is WYQEKPGKTNKLLIY (SEQ ID NO: 26), the amino acid sequence of CDR2 of the same is SGSTLQS (SEQ ID NO: 27), the amino acid sequence of FR3 of the same is GVPSKFSGSGSGTD-FTLTISSLEPEDFAMYYC (SEQ ID NO: 28), the amino acid sequence of CDR3 of the same is QQHNEYPLT (SEQ ID NO: 29), and the amino acid sequence of the FR4 (J region) of the same is FGAGTKLDLRR (SEQ ID NO: 30).

The amino acid sequence of FR1 of the VH of the P19-7D monoclonal antibody is LSQPSQSLSITCTVSGFSLT (SEQ ID NO: 31), the amino acid sequence of CDR1 of the same is TYGVH (SEQ ID NO: 32), the amino acid sequence of FR2 of the same is WVRQSPGKGLEWLG (SEQ ID NO: 33), the amino acid sequence of CDR2 of the same is VIWRGGST-DYNAAFLS (SEQ ID NO: 34), the amino acid sequence of FR3 of the same is RLSITKDNSKSQVFFKMNSLQPDD-TAIYYCAKN (SEQ ID NO: 35), the amino acid sequence of CDR3 of the same is SWDGAY (SEQ ID NO: 36), and the amino acid sequence of FR4 (J region) of the same is WGQGTLVTVS (SEQ ID NO: 37).

The amino acid sequence of FR1 of the VL of the P19-7D monoclonal antibody is SSSDVVMTQTPLSLPVSLGDQA-SISC (SEQ ID NO: 38), the amino acid sequence of CDR1 of the same is RSSQSLLHSNGNTYLH (SEQ ID NO: 39), the amino acid sequence of FR2 of the same is WYLQKPGQSP-KLLIY (SEQ ID NO: 40), the amino acid sequence of CDR2 of the same is KVSNRFS (SEQ ID NO: 41), the amino acid sequence of FR3 of the same is GVPDRFSGSGSGTD-FTLKISRVEAEDLGLYFC (SEQ ID NO: 42), the amino acid sequence of CDR3 of the same is SQNTHFPWT (SEQ ID NO: 43), and the amino acid sequence of FR4 (J region) of the same is FGGGTELEISR (SEQ ID NO: 44).

The nucleotide sequences and the amino acid sequences of V regions in H-chain and L-chain playing a role in recognition of conformational epitopes by the P18-9E and the P19-7D monoclonal antibodies were revealed.

(7) Analysis of Properties of P18-9E Monoclonal Antibody and P19-7D Monoclonal Antibody Using HCV-Like Particles (HCV-VLP)

A. Examination of Reactivity of (HCV-VLP) Monoclonal Antibody Against HCV-Like Particles (HCV-VLP) Using Enzyme Immunoassay (EIA)

(a) Preparation of HCV-Like Particles (HCV-VLP)

HCV-like particles (HCV-VLP) are empty particles containing no viral genome. Empty particles (HCV-VLP) expressing the HCV E1 protein and E2 protein on the surfaces can be prepared from 293T cells caused to express the HCV E1 protein and E2 protein using a MembranePro (registered trademark) Reagent (Invitrogen).

293T cells were cultured in a medium prepared by adding 50 mL of FCS (GIBCO) and 5 mL of PenStrep (Invitrogen) to 500 mL of DMEM (Invitrogen). $1.2 \times 10^7$ cells of 293T were seeded in a 225 $cm^2$ collagen-coated flask (IWAKI), and then cultured for a whole day at 37° C. and 5% $CO_2$.

Four mL of Opti-MEM I (GIBCO) and 216 μL of Lipofectamine 2000 (Invitrogen) were mixed. After 5 minutes of incubation at room temperature, 4 mL of Opti-MEM I (GIBCO), 10.8 μg of pcDNA J6dC-E2 (expression plasmid for the E1 protein and the E2 protein of the HCV J6CF strain described in Example 5) and 32.4 μl of MembranePro (registered trademark) Reagent (Invitrogen) were further mixed and then added, and then the solution was incuvated at room temperature for 20 minutes. The solution was added drowise to the culture solution of 293T cells cultured for a whole day, and then the cells were incuvated at 37° C. and 5% $CO_2$ for 18 hours. Subsequently, the culture solution was removed, the medium was exchanged with 35 mL of a fresh medium (from which PenStrep had been removed) and then cells were cultured for further 48 hours. The culture supernatant was collected in a 50-mL centrifugation tube, and then centrifugation was performed at 4° C. and 2,000×g for 10 minutes. The supernatant was transferred to a new 50-mL centrifugation tube (2 mL was left without transfer thereof), and then 7 mL of MembranePro Precipitation Mix (Invitrogen) was added. The resultant was mixed by inversion for several times, and then left to stand for a whole day or longer at 4° C. Thereafter, centrifugation was performed at 4° C. and 5,500×g for 5 minutes, and then the supernatant was removed using a pipette. MembranePro Precipitation Mix was diluted 6-fold with 1×PBS(−), 5 mL of the resulting solution was added to the pellet, centrifugation was further performed at 4° C. and 5,500×g for 5 minutes, and then the supernatant was removed using a pipette. 500 µL of PBS(−) was added to the pellet for suspension, the suspension was dispensed, and then the resultants were stored at −80° C. until use. The resultants were designated as "HCV-VLP."

(b) Preparation of E1 Protein and E2 Protein (Recombinant Proteins) Derived from the J6CF Strain E1 protein and E2 protein derived from the J6CF strain (recombinant proteins) were separately prepared by the method described in (1) of Example 7.

(c) Enzyme Immunoassay (EIA)

To a 96-well plate (Nunc), a mixture of the E1 protein and the E2 protein which are recombinant proteins (50 ng each) was diluted with PBS(−) and then added at 50 µl/well for immobilization. Similarly, HCV-VLP prepared in "a. Preparation of HCV-like particles (HCV-VLP)" was added at 500 ng/well, and then the solution was incubated for a whole day at 4° C. for immobilization. The antigen solution was decanted off, Blocking One (Nacalai Tesque) diluted 5-fold with milliQwater was added at 200 µL/well, and then the solution was incubated at room temperature for 1 hour, so that blocking was performed. The blocking solution was decanted off and the resultant was washed twice with 0.05% (v/v) Tween 20 (Sigma)-containing PBS(−) (hereinafter, referred to as "washing solution"). A monoclonal antibody solution (P18-9E or P19-7D) diluted with a washing solution was added at 50 µL/well. To negative control wells, a washing solution alone was added at 50 µL/well. After about 1.5 hours of incubation at room temperature, washing was performed 3 times with a washing solution. Next, an HRP-labeled anti-mouse IgG antibody (Amersham) diluted 3.000-fold with a washing solution was added at 50 µL/well. After 1 hour of incubation at room temperature, the resultant was washed 4 times with a washing solution. A color development solution was prepared according to instructions included with a color development kit for peroxidase (Sumiron) and then added at 50 µL/well. After 15 minutes of incubation at room temperature, a reaction stop solution included with the kit was added at 50 µL/well. Subsequently, absorbance at 450 nm was measured using a microplate reader (Model 680, Bio-Rad). The absorbance of the negative control well was subtracted from the absorbance of each well, and the thus obtained value was designated as representing the reaction of each solution.

In this experiment, the 8D10-3 monoclonal antibody (WO2010/038789) was used as a control antibody. The 8D10-3 monoclonal antibody was obtained by immunizing a BALB/c mouse with a recombinant E2 protein, which has a linear epitope of the E2 protein.

Figure 6:
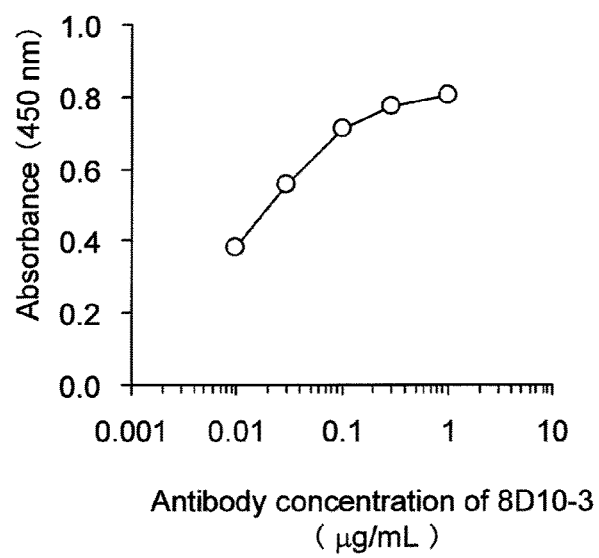
FIG. 6 shows the result of enzyme immunoassay (EIA) for the 8D10-3 monoclonal antibody using plates on which the recombinant E1 and E2 proteins were immobilized.
Figure 7:
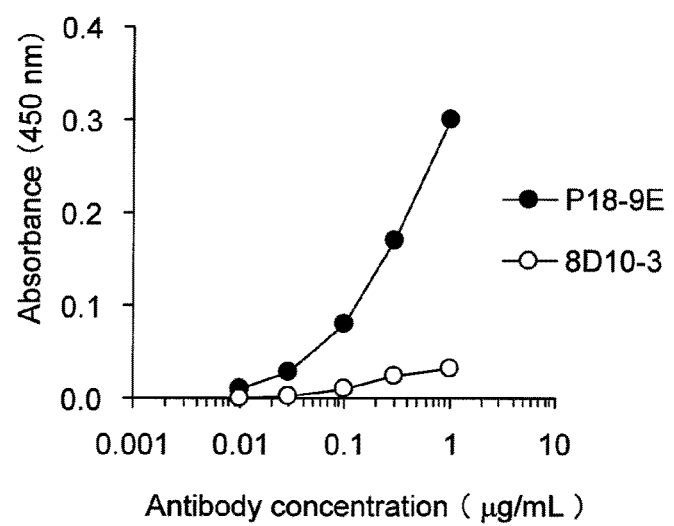
FIG. 7 shows the result of EIA for the 8D10-3 monoclonal antibody and the P18-9E monoclonal antibody using plates on which HCV-like particles (HCV-VLP) were immobilized.
Figure 8:
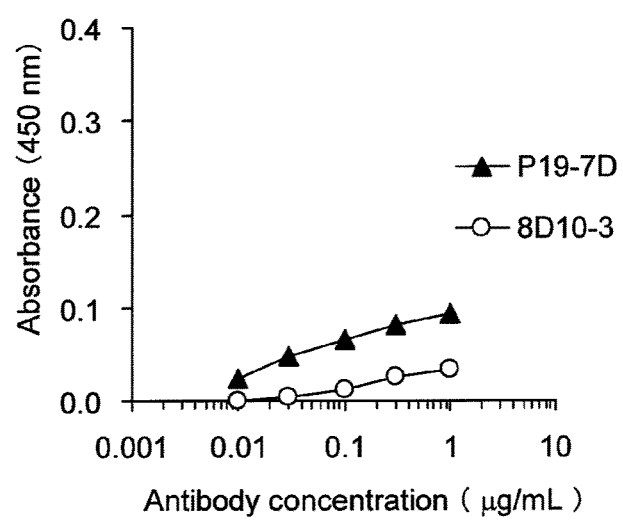
FIG. 8 shows the result of EIA for the 8D10-3 monoclonal antibody and the P19-7D monoclonal antibody using plates on which HCV-like particles (HCV-VLP) were immobilized.

The results are shown in FIG. 6 to FIG. 8. FIG. 6 shows the results of EIA for the 8D10-3 monoclonal antibody with the use of a plate on which a mixture of a recombinant E1 protein and a recombinant E2 protein had been immobilized. FIG. 7 shows the results of EIA for the 8D10-3 monoclonal antibody and the P18-9E monoclonal antibody with the use of plates on which HCV-like particles (HCV-VLP) were immobilized. FIG. 8 shows the results of EIA for the 8D10-3 monoclonal antibody and the P19-7D monoclonal antibody with the use of plates on which HCV-like particles (HCV-VLP) were immobilized. Vertical axes in the figures indicate the values of absorbance at 450 nm and the horizontal axes in the same indicate the concentrations (ug/mL) of the monoclonal antibodies.

As a result, the 8D10-3 monoclonal antibody reacted with the mixture of recombinant proteins, the E1 protein and the E2 protein (FIG. 6). On the other hand, the reaction of the 8D10-3 monoclonal antibody against HCV-VLP was found to be weaker than that of the P18-9E monoclonal antibody against HCV-VLP (FIG. 7). Similarly, the reaction of the 8D10-3 monoclonal antibody against HCV-VLP was weaker than that of the P19-7D monoclonal antibody against HCV-VLP (FIG. 8).

Whereas the 8D10-3 monoclonal antibody recognising a linear epitope of the E2 protein had weak ability to recognize the envelope structure on the HCV-VLP surface, the P18-9E monoclonal antibody and the P19-7D monoclonal antibody were suggested to be highly reactive to HCV-VLP and recognize the envelope conformation of a complex of the E1 protein and the E2 protein on the surfaces of HCV particles.

B. Examination of Reactivity of Monoclonal Antibody Against HCV-Like Particles (HCV-VLP) Using Biacore (a) Immobilization of Protein A/G Among sensor chips for surface plasmon resonance measuring apparatus Biacore S51 (GE), Series S sensor chip CM-5 (GE) was mounted on Biacore S51, HBS-EP (GE), which is assay buffer diluted 1-fold with ultrapure water, was allowed to run over the chip at a flow rate of 30 µL/min. The internal temperature was set at 25° C. EDC (N-ethyl-N'-(3-dimethylaminopropyl) carbodiimide hydrorochloride) and NHS(N-hydroxysuccinimide) in an amine coupling kit (GE) were prepared to be 100 mM and 400 mM, respectively. Protein A/G (50 µg/mL, Pierce) was prepared with Acetate 4.0 (GE). With the use of the thus prepared EDC and NHS, and an ethanolamine solution in the same kit, protein A/G was immobilized by amine coupling. A series of immobilization procedures were performed at a flow rate of 10 µL/min, and the time for addition of protein A/G was determined to be 10 minutes. Therefore, protein A/G was immobilized in almost equivalent amounts into both spots 1 and 2 of the same flow cell.

(b) Capture of Antibody

The purified P18-9E monoclonal antibody and mouse IgG (Sigma) adjusted at 20 µg/mL with HBS-EP were allowed to run over the above chip at a flow rate of 10 µL/min for 8 minutes. With the use of affinity of Protein A/G and the Fc site of each antibody, the P18-9E monoclonal antibody was captured in spot 1 and the mouse IgG was captured in spot 2 on the chip.

(c) Association and Dissociation of VLP

HCV-VLP adjusted at 30, 100, or 300 µg/mL with HBS-EP was allowed to run over the chip at a flow rate of 10 µL/min for 3 minutes. Binding reaction of VLP was monitored by real-time measurement of surface plasmon resonance, HBS-EP was allowed to run for 10 minutes and then dissociation reaction was measured.

(d) Analysis

S51 Evaluation was used for analysis. Measured values were expressed with RU (Resonance Unit; that is the unit of resonance response). Correction was carried out by subtracting a value representing the reaction of HCV-VLP against mouse IgG (regarded as a value representing non-specific adsorption) from a value representing the reaction of HCV-VLP against the P18-9E monoclonal antibody.

(e) Result

As a result, a VLP-concentration-dependent manner and antigen-antibody reaction-like gentle association and dissociation to the P18-9E monoclonal antibody were observed. The result also suggested that the P18-9E monoclonal antibody binds to HCV-VLP and recognizes envelope conformation formed by the complex of the E1 protein and the E2 protein on the surfaces of HCV particles.

Industrial Applicability

The antibody of the present invention having activity of inhibiting HCV infection can be used as a medicament for treatment and prevention of HCV infection.

Sequence Listing Free Text

SEQ ID NO: 1 discloses the HCV genome cDNA sequence cloned into pJFH-1.
SEQ ID NO: 2 discloses the chimeric HCV genome cDNA sequence cloned into pJ6/JFH-1.
SEQ ID NO: 3 discloses the sequence of the primer (J6E1dTM-s).
SEQ ID NO: 4 discloses the sequence of the primer (J6E1dTM-as).
SEQ ID NO: 5 discloses the sequence of the primer (J6E2dTM-s).
SEQ ID NO: 6 discloses the sequence of the primer (J6E2dTM-as).
SEQ ID NO: 7 discloses the sequence of the $1^{st}$ to the $162^{nd}$ amino acid residues of the E1 protein of the J6CF strain.
SEQ ID NO: 8 discloses the sequence of the $1^{st}$ to the $337^{th}$ amino acid residues of the E2 protein of the J6CF strain.
SEQ ID NO: 9 discloses the nucleotide sequence of the gene encoding VH of the P18-9E monoclonal antibody.
SEQ ID NO: 10 discloses the nucleotide sequence of the gene encoding VL of the P18-9E monoclonal antibody.
SEQ ID NO: 11 discloses the nucleotide sequence of the gene encoding VH of the P19-7D monoclonal antibody.
SEQ ID NO: 12 discloses the nucleotide sequence of the gene encoding VL of the P19-7D monoclonal antibody.
SEQ ID NO: 13 discloses the amino acid sequence of VH of the P18-9E monoclonal antibody.
SEQ ID NO: 14 discloses the amino acid sequence of VL of the P18-9E monoclonal antibody.
SEQ ID NO: 15 discloses the amino acid sequence of VH of the P19-7D monoclonal antibody.
SEQ ID NO: 16 discloses the amino acid sequence of VL of the P19-7D monoclonal antibody.
SEQ ID NO: 17 discloses the amino acid sequence of FR1 in VH of the P18-9E monoclonal antibody.
SEQ ID NO: 18 discloses the amino acid sequence of CDR1 in VH of the P18-9E monoclonal antibody.
SEQ ID NO: 19 discloses the amino acid sequence of FR2 in VH of the P18-9E monoclonal antibody.
SEQ ID NO: 20 discloses the amino acid sequence of CDR2 in VH of the P18-9E monoclonal antibody.
SEQ ID NO: 21 discloses the amino acid sequence of FR3 in VH of the P18-9E monoclonal antibody.
SEQ ID NO: 22 discloses the amino acid sequence of CDR3 in VH of the P18-9E monoclonal antibody.
SEQ ID NO: 23 discloses the amino acid sequence of FR4 (J region) in VH of the P18-9E monoclonal antibody.
SEQ ID NO: 24 discloses the amino acid sequence of FR1 in VL of the P18-9E monoclonal antibody.
SEQ ID NO: 25 discloses the amino acid sequence of CDR1 in VL of the P18-9E monoclonal antibody.
SEQ ID NO: 26 discloses the amino acid sequence of FR2 in VL of the P18-9E monoclonal antibody.
SEQ ID NO: 27 discloses the amino acid sequence of CDR2 in VL of the P18-9E monoclonal antibody.
SEQ ID NO: 28 discloses the amino acid sequence of FR3 in VL of the P18-9E monoclonal antibody.
SEQ ID NO: 29 discloses the amino acid sequence of CDR3 in VL of the P18-9E monoclonal antibody.
SEQ ID NO: 30 discloses the amino acid sequence of FR4 (J region) in VL of the P18-9E monoclonal antibody.
SEQ ID NO: 31 discloses the amino acid sequence of FR1 in VH of the P19-7D monoclonal antibody.
SEQ ID NO: 32 discloses the amino acid sequence of CDR1 in VH of the P19-7D monoclonal antibody.
SEQ ID NO: 33 discloses the amino acid sequence of FR2 in VH of the P19-7D monoclonal antibody.
SEQ ID NO: 34 discloses the amino acid sequence of CDR2 in VH of the P19-7D monoclonal antibody.
SEQ ID NO: 35 discloses the amino acid sequence of FR3 in VH of the P19-7D monoclonal antibody.
SEQ ID NO: 36 discloses the amino acid sequence of CDR3 in VH of the P19-7D monoclonal antibody.
SEQ ID NO: 37 discloses the amino acid sequence of FR4 (J region) in VH of the P19-7D monoclonal antibody.
SEQ ID NO: 38 discloses the amino acid sequence of FR1 in VL of the P19-7D monoclonal antibody.
SEQ ID NO: 39 discloses the amino acid sequence of CDR1 in VL of the P19-7D monoclonal antibody.
SEQ ID NO: 40 discloses the amino acid sequence of FR2 in VL of the P19-7D monoclonal antibody.
SEQ ID NO: 41 discloses the amino acid sequence of CDR2 in VL of the P19-7D monoclonal antibody.
SEQ ID NO: 42 discloses the amino acid sequence of FR3 in VL of the P19-7D monoclonal antibody.
SEQ ID NO: 43 discloses the amino acid sequence of CDR3 in VL of the P19-7D monoclonal antibody.
SEQ ID NO: 44 discloses the amino acid sequence of FR4 (J region) in VL of the P19-7D monoclonal antibody.

All publications, patents, and patent applications cited herein are incorporated herein by reference in their entirety.

The invention claimed is:

1. An isolated anti-hepatitis C virus antibody, wherein a heavy chain variable region contains a complementarity determining region 1 ($CDR1_H$), a complementarity determining region 2 ($CDR2_H$), and a complementarity determining region 3 ($CDR3_H$) comprising respectively the amino acid sequences shown in SEQ ID NOs: 18, 20, and 22 in the sequence listing and a light chain variable region contains a complementarity determining region 1 ($CDR1_L$), a complementarity determining region 2 ($CDR2_L$), and a complementarity determining region 3 ($CDR3_L$) comprising respectively the amino acid sequences shown in SEQ ID NOs: 25, 27, and 29 in the sequence listing.

2. The isolated anti-hepatitis C virus antibody according to claim 1, which is produced by the hybridoma cell line under Accession No. FERM BP-11263.

3. The isolated anti-hepatitis C virus antibody according to claim 1, which is a humanized antibody.

4. A hybridoma cell line, the Accession No. of which is PERM BP-11263.

5. An inhibitory agent for infection with hepatitis C virus, which contains the isolated anti-hepatitis C virus antibody according to claim 1 as an active ingredient.

* * * * *